United States Patent
Maresca, Jr.

(10) Patent No.: US 10,345,270 B1
(45) Date of Patent: Jul. 9, 2019

(54) MEASUREMENT-BASED, IN-SERVICE METHOD FOR DETERMINING THE TIME TO THE NEXT INTERNAL INSPECTION OF AN AST

(71) Applicant: Vista Precision Solutions, Inc., Richland, WA (US)

(72) Inventor: Joseph W. Maresca, Jr., Sunnyvale, CA (US)

(73) Assignee: Vista Precision Solutions, Inc., Richland, WA (US)

( * ) Notice: Subject to any disclaimer, the term of this patent is extended or adjusted under 35 U.S.C. 154(b) by 128 days.

(21) Appl. No.: 15/490,688

(22) Filed: Apr. 18, 2017

Related U.S. Application Data

(60) Provisional application No. 62/324,099, filed on Apr. 18, 2016.

(51) Int. Cl.

| | | |
|---|---|---|
| G06F 11/30 | (2006.01) | |
| G01N 29/14 | (2006.01) | |
| G01B 17/02 | (2006.01) | |
| G01N 29/07 | (2006.01) | |
| G01N 29/04 | (2006.01) | |
| B65D 90/50 | (2019.01) | |

(Continued)

(52) U.S. Cl.
CPC ............ *G01N 29/14* (2013.01); *B65D 90/50* (2013.01); *G01B 17/02* (2013.01); *G01B 21/18* (2013.01); *G01N 29/043* (2013.01); *G01N 29/07* (2013.01); *G01M 3/00* (2013.01); *G01N 2291/0258* (2013.01); *G01N 2291/0289* (2013.01); *G01N 2291/02854* (2013.01)

(58) Field of Classification Search
CPC ..................................................... G01N 29/14
See application file for complete search history.

(56) References Cited

U.S. PATENT DOCUMENTS

| | | |
|---|---|---|
| 4,418,574 A | 12/1983 | Flournoy |
| 4,918,989 A | 4/1990 | Desrulles et al. |
| 5,231,866 A | 8/1993 | Peacock |

(Continued)

*Primary Examiner* — Phuong Huynh
(74) *Attorney, Agent, or Firm* — Pillsbury Winthrop Shaw Pittman LLP

(57) ABSTRACT

Methods for quantitatively determining the time (TNI) between (1) the application of this method and (2) the time at which an out-of-service internal inspection of a steel, field-erected, aboveground storage tank (AST) containing a petroleum product or water should be performed. These methods combine in-service measurements of the thickness, integrity, and corrosion rate of the tank bottom with an empirical corrosion rate cumulative frequency distribution (CFD) for the tank of interest to develop a Bayesian tank bottom survival probability distribution to determine TNI. During this entire TNI time period, the risk of tank bottom failure is less than at the time these methods were applied. If available, the results of a previous out-of-service API 653 internal inspection are also used. These methods are applied to a single tank and can be applied at any time during the service life of a tank to check or update the internal inspection interval that was previously determined that is based on the condition of the tank bottom. These methods focus on refined petroleum applications, but they can be applied to a wide range of liquid products providing the maximum corrosion rate CFD of the tank bottom can be determined.

17 Claims, 107 Drawing Sheets

(51) Int. Cl.
*G01B 21/18* (2006.01)
*G01M 3/00* (2006.01)

(56) References Cited

U.S. PATENT DOCUMENTS

| | | |
|---|---|---|
| 5,499,540 A | 3/1996 | Whaley |
| 5,634,378 A | 6/1997 | Burkhardt, Jr. |
| 5,854,557 A | 12/1998 | Tiefnig |
| 7,143,635 B1 | 12/2006 | Major |
| 9,228,932 B1 | 1/2016 | Maresca, Jr. et al. |
| 9,766,175 B1 | 9/2017 | Maresca, Jr. et al. |
| 2002/0043973 A1 | 4/2002 | Amini et al. |
| 2005/0011278 A1* | 1/2005 | Brown .................. G01F 1/666 73/861.18 |
| 2006/0010995 A1 | 1/2006 | Silverman |
| 2006/0169022 A1 | 8/2006 | Sato et al. |
| 2006/0283251 A1 | 12/2006 | Hunaidl et al. |
| 2007/0212404 A1 | 9/2007 | Kim et al. |
| 2010/0212404 A1* | 8/2010 | Wolford .............. G01M 3/3263 73/45.5 |
| 2011/0185814 A1 | 8/2011 | Piccolo |
| 2016/0123864 A1 | 5/2016 | Maresca, Jr. et al. |

\* cited by examiner

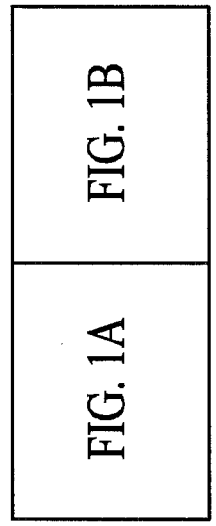

| FIG. 11A | FIG. 11B | FIG. 11C | FIG. 11D | FIG. 11E | FIG. 11F |

FIG. 11

| FIG. 43A | FIG. 43B |
| --- | --- |
| FIG. 43C | FIG. 43D |
| FIG. 43E | FIG. 43F |
| FIG. 43G | FIG. 43H |
| FIG. 43I | FIG. 43J |

FIG. 43

Yellow highlighted areas require an input to be entered in column D

Input parameters (1) What is the date of the application of this standard by month and year (mm,yyy): $t_{0\text{-age}}$: _____ years (2) Determine the age of the tank in years, $t_0$, since the time of the completion of the last out-of-service API 653 internal inspection or the date when a new or refurbished tank was brought back into service: $t_0$ = _____ year (3) The mean or median measurement of the tank bottom thickness, $T_{0\,\text{min}}$, in inches, determined in step 3 of this standard at $t_0$: $T_{0\,\text{min}}$ = _____ inches (circle one: mean or median)

(4) What is the date of the completion of the last out-of-service API 653 internal inspection or the date when a new tank was brought back into service by month and year (mm, yyy)? $t_{P\,\text{age}}$ : = _____ years (5) Determine the age of the tank in years, $t_P$, at the time of the completion of the last out-of-service API 653 internal inspection, or the date when a new or refurbished tank was brought back into service: (either a previous API 653 internal inspection or when the tank was new): $t_P$ = _____ years (6) The mean or median thickness of the tank bottom, $T_{P\,\text{min}}$, in inches, determined from tank bottom thickness measurements made at the last out-of-service API 653 internal inspection after maintenance and/or repairs, or re- (7) The minimum allowable thickness, $T_{MAT}$, (typically 0.05 or 0.10 inches): $T_{MAT}$ = _____ inches (8) What is $y_1 = t_0 - t_P$, $y_1 = t_0 - t_P$ = _____ years Step 2 - leak detection integrity test?

(1) Was a leak detection integrity test performed? (Yes or no)

(2) What was the result of the leak detection integrity test (pass, fail)

(3) This standard method can be considered for use only if the tank of interest passes the leak detection integrity test:

FIG. 43A

Enter only the yellow highlighted areas

Date of applicate of this standard:  Month = 3       Year = 2016 t_0 =  20.0  years

T_0 min =  0.2388  in.

Date of the previous out-of-service API 653 Internal
Inspection:  Month = 3       Year = 1996 t_P =  0.0  years

T_0 min =  0.250  in.
T_MAT =  0.10  in.
y_1 = t_0 - t_P =  20.0  years

Was a leak detection integrity test performed? (Yes or N0)  Yes

Leak detection integrity test result (Pass or Fail) =  Pass

Yes: Standard can be considered for use

FIG. 43B

Yes: Standard can be considered for use

Step 3 - API 653 external inspection, in-service measurements of bottom thickness, and in-service measurements of average bottom thickness and corrosion rate in the tank of interest API 653 external inspection (1) Was an in service API 653 external inspection performed? (Yes or no)?
(2) Does the results of the API 653 external inspection prohibit the use of this ASTM standard method? (Yes or no)?
(3) Will the results of the API 653 external inspection be used in this ASTM standard method? (Yes or no)?
(4) If an in-service API 653 external inspection was performed, enter the month, if available, and the year (mm,yyyy): t_Ext API 653 age: _____ year
(5) Was the in-service API 653 external inspection performed within 2 months of the application of this standard?

Yes: Standard can be considered for use

What is $T_{min}$ and $CR_{max}$ for the tank of interest do to external or bottom side pitting?

(1) $T_{AVE}$ from Step 3: _____ inches
(2) $CR_{AVE} = T_{AVE} / (t_0 - t_P)$ from Step 3: _____ mpy
(3) $CR_{Ratio}$ from Step 3: _____
(4) Was $T_{pitting}$ from Step 3 (a) measured directly or (b) computed from $T_{Avg}$ )

(5) $CR_{max}$ Due to external pitting from step 3: _____ mpy
(6) $T_{min\ ext}$ from Step 3: _____ inches

FIG. 43C

Was and API 653 external inspection performed? (Yes or no) — Yes does the API 653 external inspection prohibit use of this standard? (Yes or no) — no will the results of the API 653 external inspection be used in this standard? (Yes or no) — Yes Date of the API 653 external inspection: Month = 3  Year = 2016 was the in-service API 653 external inspection performed within 2 months of the application of this standard? — Yes: Standard can be considered $T_{avg}$ = 0.239 inches
$CR_{avg}$ = 0.560 mpy
$CR_{ratio}$ = 8.0

Was $T_{pitting}$ (a) measured directly or (b) computed from $T_{avg}$ in Step 3 — b $CR_{max\ pitting}$ = 4.480 mpy
$T_{min\ ext}$ = 0.160 inches

FIG. 43D (7) $CR_{max\,sum}$ from Step 3: _____ inches (8) $T_{min\,sum}$ from Step 3: _____ inches (9) Is $CR_{max}$ computed just from external or maximum corrosion or both the sum of internal and external? (External, Both) _____

(10) $CR_{max}$ To use for only AECAT _____ mpy

(11) $T_{min}$ to use for only AECAT _____ inches

Step 4 - Determine $F_X(x)$ to Use (1) What is the survival possibility based on the corrosion thickness of the tank bottom? $S_y(y=t0) = (T_0 - T_{MAT}) / (T_P - T_{MAT})$: _____

(2) Determine $\gamma$, $\beta$ and $\eta$ for this survival probability using $CR_{max}$ following appendix 11. Plots will be generated by the worksheet.

(1) $\gamma$ =

(2) $\beta$ =

(3) $\eta$ =

(4) Mean $F_X(x)$ =

(5) StDev $F_X(x)$ =

(6) COV $F_X(x)$ =

(7) Mean $S_Y(y)$ =

(8) StDev $S_Y(y)$ =

(9) COV $S_Y(y)$ =

FIG. 43E

| | | |
|---|---:|---|
| $CR_{max\ ext+int}$ = | 6.272 | mpy |
| $T_{min\ ext+int}$ = | 0.125 | inches |
| CR assume external/maximum or both? | External | |
| $CR_{max}$ to use for only AECAT = | 4.48 | mpy |
| $T_{min}$ to use for only AECAT = | 0.160 | inches |
| Survival probability based on tank bottom corrosion = | 0.403 | |

Determine $\gamma$, $\beta$ and $\eta$ for this survival probability using $CR_{max}$ following appendix 11. Plots will be generated by the worksheet.

| | | |
|---|---:|---|
| $\gamma$ = | -1.00 | |
| $\beta$ = | 5.80 | |
| $\eta$ = | 4.50 | |
| Mean FX(x) = | 3.17 | mpy |
| StDev FX(x) = | 0.83 | mpy |
| COV FX(x) = | 0.26 | mpy |
| Mean SY(y) = | 18.94 | years |
| StDev SY(y) = | 4.97 | years |
| COV SY(y) = | 0.26 | years |

FIG. 43F

Steps 5,6,7 - Generate $F_Y(y)$, $S_Y(y/t0)$ as graphs in the Excel worksheet

Step 8 - Computation of TNI-ER (1) What is $t_0 - t_{P?}$ $t_0 - t_{P?}$ = _____ years (2) What is y equal to at the implementation of this standard $(y_1 = t_0 - t_P)$?

(3) What is the survival probability, $S_Y(y_1 = t_0 - t_P)$?

(4) What is the survival age region? (A, B, C, D) Note: Look on the $S_Y(y)$ and $S_Y(y/t0)$ graphs?

(5) $S_Y(y_2 = t_N / y_1 = (t_0 - t_P)) / = [S_Y(y_1 = t_0 - t_P)]^2$ (6) What is the $y_2 = t_N - t_0$? Look up the inverse in the Excel sheet.

(7) What is TNI-ER in years $(y_2 - y_1)$?

(7a) What is TNI-ER in years $(y_2 - y_1)$ determined from equivalent risk plot?

Step 9 - Additional measurements of the entire tank bottom (1) Were additional measurements made as described in Step 9: _____ (yes or no)

TNI-α CANNOT be determined or used and TNI is based only on TNI-ER

Output Results (1) TNI: _____ years
(2) TNI-ER: _____ years
(3) TNI- : _____ years

FIG. 43G $t\_0 - t\_P =$     20.0    years
$y = t\_0 - t\_P =$     20.0    years
$SY(y = (t\_0 - tP)) =$     0.400
Survival Age Region =    B
$SY(y = tN / y = (t0 - tP))/ = [SY(y = t0 - tP))^\wedge 2 =$     0.160    years
$y2 = t\_N - t\_0 =$     25.900    years
$TNI\text{-}ER = y\_2 - y\_1 =$     5.9    years
$TNI\text{-}ER = y\_2 - y\_1 =$     6.1    years Were additional measurements of the entire tank bottom made?    No.
TNI-$\alpha$ CANNOT be determined or used and TNI is based only on TNI-ER

Output Results
TNI =     6.1    years
TNI-ER =     6.1    years
TNI-$\alpha$ =     Determination    years

FIG. 43H

(4) TNI is greater than 10 years, TNI is set equal to 10 years and is re-assessed in 10 years by repeating this standard.
(5) $T_{min}$ for TNI-ER _____ inches
(6) $CR_{max}$ for TNI-ER _____ mpy
(7) $T_{min}$ for TNI-$\alpha$ _____ inches
(8) $CR_{max}$ for TNI-$\alpha$ _____ mpy

*Recommendation (circle (a), (b), or (c))*
(a) this ASTM standard method recommends that an out of service API 653 internal inspection be performed.
(b) this ASTM standard method recommends that an in-service API 653 external inspection be performed before the results of this standard be reported.

_____   _____   _____
Signature                 Name                      Date

Graphs of $F_X(x)$, $F_Y(y)$, $S_Y(y)$, and $S_Y(y/t_0)$
(1) Corrosion rate Weibull distributed CDF with ($\gamma$, $\beta$ and $\eta$): $F_X(x)$
(2) Tank failure Weibull distributed CDF with ($\gamma$, $\beta$ and $\eta$): $F_X(x)$
(3) Tank survival Weibull distributed CDF with ($\gamma$, $\beta$ and $\eta$): $F_X(x)$
(4) Bayesian update of $S_Y(y)$ Weibull distributed CDF with ($\gamma$, $\beta$ and $\eta$): $S_Y(y/t_0)$

FIG. 43I

| | | |
|---|---|---|
| TNI to use if TNI above is > 10 years = | 6.1 | years |
| T_min = | 0.16 | inches |
| CR_max = | 4.48 | mpy |
| T_min = | | inches |
| CR_max = | | mpy |

FIG. 43J

| FIG. 44A | FIG. 44B |
| --- | --- |
| FIG. 44C | FIG. 44D |
| FIG. 44E | FIG. 44F |
| FIG. 44G | FIG. 44H |
| FIG. 44I | FIG. 44J |
| FIG. 44K | FIG. 44L |
| FIG. 44M | |

FIG. 44

Yellow highlighted areas require an input to be entered in column D

Input parameters (1) What is the date of the application of this standard by month and year (mm,yyy): $t_{0\,age}$ : _____ years (2) Determine the age of the tank in years, $t_0$, since the time of the completion of the last out-of-service API 653 internal inspection or the date when a new or refurbished tank was brought back into service: $t_0$ = _____ year (3) The mean or median measurement of the tank bottom thickness, $T_{0\,min}$, in inches, determined in step 3 of this standard at $t_0$; $T_{0\,min}$ = _____ inches (circle one: mean or median)

(4) What is the date of the completion of the last out-of-service API 653 internal inspection or the date when a new tank was brought back into service by month and year (mm, yyy)? $t_{P\,age}$ = _____ years (5) Determine the age of the tank in years, $t_P$, at the time of the completion of the last out-of-service API 653 internal inspection, or the date when a new or refurbished tank was brought back into service: (either a previous API 653 internal inspection or when the tank was new): $t_P$ = _____ years (6) The mean or median thickness of the tank bottom, $T_{P\,min}$, in inches; determined from tank bottom thickness measurements made at the last out-of-service API 653 internal inspection after maintenance and/or repairs, or re-measurements made at the last out-of-service API 653 internal inspection after maintenance and/or repairs, or re- (7) The minimum allowable thickness, $T_{MAT}$, (typically 0.05 or 0.10 inches); $T_{MAT}$ = _____ inches (8) What is $y_1 = t_0 - t_P$, $y_1 = t_0 - t_P$ = _____ years Step 2 - leak detection integrity test?
(1) Was a leak detection integrity test performed? (Yes or no)
(2) What was the result of the leak detection integrity test (pass, fail)
(3) This standard method can be considered for use only if the tank of interest passes the leak detection integrity test:

FIG. 44A

Enter only the yellow highlighted areas.

Date of applicate of this standard:   Month = 3    Year = 2016 t_0 =   20.0   years

T_0 min =   0.2388   in.

Date of the previous out-of-service API 653 Internal
Inspection:   Month = 3    Year = 1996 t_P =   0.0   years

T_0 min =   0.250   in.
T_MAT =   0.10   in.
y_1 = t_0 - t_P =   20.0   years

Was a leak detection integrity test performed? (Yes or NO)   Yes
Leak detection integrity test result (Pass or Fail) =   Pass Yes: Standard can be considered for use

FIG. 44B

Yes: Standard can be considered for use

Step 3 - API 653 external inspection, in-service measurements of bottom thickness, and in-service measurements of average bottom thickness and corrosion rate in the tank of interest
API 653 external inspection (1) Was an in service API 653 external inspection performed? (Yes or no)?
(2) Does the results of the API 653 external inspection prohibit the use of this ASTM standard method? (Yes or no)?
(3) Will the results of the API 653 external inspection be used in this ASTM standard method? (Yes or no)?
(4) If an in-service API 653 external inspection was performed, enter the month, if available, and the year (mm,yyyy):
t_Ext API 653 age: _____ year
(5) Was the in-service API 653 external inspection performed within 2 months of the application of this standard?

Yes: Standard can be considered for use

What is $T_{min}$ and $CR_{max}$ for the tank of interest do to external or bottom side pitting?

(1) $T_{AVE}$ from Step 3: _____ inches
(2) $CR_{AVE} = T_{AVE} / (t_0 - t_P)$ from Step 3: _____ mpy
(3) $CR_{Ratio}$ from Step 3: _____
(4) Was $T_{pitting}$ from Step 3 (a) measured directly or (b) computed from $T_{Avg}$ )

(5) $CR_{max}$ Due to external pitting from step 3: _____ mpy
(6) $T_{min\ ext}$ from Step 3: _____ inches

FIG. 44C

Was and API 653 external inspection performed? (Yes or no)    Yes
does the API 653 external inspection prohibit use of this
standard? (Yes or no)    no
will the results of the API 653 external inspection be used
in this standard? (Yes or no)    Yes Date of the API 653 external inspection:    Month = 3    Year = 2016
was the in-service API 653 external inspection performed
within 2 months of the application of this standard?    Yes: Standard can be considered $T_{avg}$ =    0.239    inches
$CR_{avg}$ =    0.560    mpy
$CR_{ratio}$ =    8.0

Was $T_{pitting}$ (a) measured directly or (b) computed from    b
$T_{avg}$ in Step 3

$CR_{max\ pitting}$ =    4.480    mpy
$T_{min\ ext}$ =    0.160    inches

FIG. 44D (7) $CR_{max\,sum}$ from Step 3: _____ inches (8) $T_{min\,sum}$ from Step 3: _____ inches (9) Is $CR_{max}$ computed just from external or maximum corrosion or both the sum of internal and external? (External, Both) _____

(10) $CR_{max}$ To use for only AECAT _____ mpy

(11) $T_{min}$ to use for only AECAT _____ inches

Step 4 - Determine $F_x(x)$ to Use (1) What is the survival possibility based on the corrosion thickness of the tank bottom? $S_y(y=t0) = (T_0 - T_{MAT})/(T_P - T_{MAT})$: _____

(2) Determine $\gamma$, $\beta$ and $\eta$ for this survival probability using $CR_{max}$ following appendix 11. Plots will be generated by the worksheet.

(1) $\gamma$ =
(2) $\beta$ =
(3) $\eta$ =
(4) Mean $F_x(x)$ =
(5) StDev $F_x(x)$ =
(6) COV $F_x(x)$ =
(7) Mean $S_y(y)$ =
(8) StDev $S_y(y)$ =
(9) COV $S_y(y)$ =

FIG. 44E

| | | |
|---|---:|---|
| $CR_{max\ ext + int}$ = | 6.272 | mpy |
| $T_{min\ ext + int}$ = | 0.125 | inches |
| CR assume external/maximum or both? | External | |
| $CR_{max}$ to use for only AECAT = | 4.48 | mpy |
| $T_{min}$ to use for only AECAT = | 0.160 | inches |
| Survival probability based on tank bottom corrosion = | 0.403 | |

Determine $\gamma$, $\beta$ and $\eta$ for this survival probability using $CR_{max}$ following appendix 11. Plots will be generated by the worksheet.

| | | |
|---|---:|---|
| $\gamma$ = | -1.00 | |
| $\beta$ = | 5.80 | |
| $\eta$ = | 4.50 | |
| Mean FX(x) = | 3.17 | mpy |
| StDev FX(x) = | 0.83 | mpy |
| COV FX(x) = | 0.26 | mpy |
| Mean SY(y) = | 18.94 | years |
| StDev SY(y) = | 4.97 | years |
| COV SY(y) = | 0.26 | years |

FIG. 44F

Steps 5,6,7 - Generate $F_y(y)$, $S_y(y/t0)$ as graphs in the Excel worksheet

Step 8 - Computation of TNI-ER
(1) What is $t_0 - t_{P?}$ $t_0 - t_{P?}$ = _____ years
(2) What is y equal to at the implementation of this standard ($y_1 = t_0 - t_P$)?
(3) What is the survival probability, $S_Y(y_1 = t_0 - t_P)$?
(4) What is the survival age region? (A, B, C, D) Note: Look on the $S_Y(y)$ and $S_Y(y/t0)$ graphs?
(5) $S_Y(y_2 = t_N/y_1 = (t_0 - t_P))/ = [S_Y(y_1 = t_0 - t_P)]^2$
(6) What is the $y_2 = t_N - t_0$? Look up the inverse in the Excel sheet.
(7) What is TNI-ER in years ($y_2 - y_1$)?
(7a) What is TNI-ER in years ($y_2 - y_1$) determined from equivalent risk plot?

Step 9 - Additional measurements of the entire tank bottom (1) Were additional measurements made as described in Step 9: _____ (yes or no)

TNI-α Can be determined and used if survival age region is B (1) If Yes, methods were used: (EWnter all that apply beneath the letter: (a) AECAT; (b) previous out-of-service API 653 internal inspection; (c) both (a) and (b); and (d) robotic inspection.

Steps 10 and 11: Results of additional measurements made in Step 10, including determination of TNI-α

FIG. 44G $t\_0 - t\_P =$     20.0    years $y = t\_0 - t\_P =$     20.0    years $SY(y = (t\_0 - tP)) =$     0.400

Survival Age Region =     B $SY(y = tN / y = (t0 - tP))/ = [SY(y = t0 - tP)]^{\wedge}2 =$     0.160

$y2 = t\_N - t\_0 =$     25.900    years

TNI-ER = $y\_2 - y\_1 =$     5.9    years

TNI-ER = $y\_2 - y\_1 =$     6.1    years

Were additional measurements of the entire tank bottom made?    Yes

TNI-α Can be determined and used if survival age region is B (a) - AECAT    (b) - prev API 653    (c) - both Yes    No    No

FIG. 44H

Enter the information for an AECAT test

Steps 9 - 11 for AECAT (a) AECAT (1) Was an AECAT test performed and it is it available for use with this standard? (Yes or no)
(2) Does the results of the AECAT test prohibit the use of this measurement option? (Yes or no)
(3) Will the results of the AECAT test be used as a measurement option? (Yes or no)
(4) AECAT (measurement date: Enter the month, if available and the year: _____ (mm,yyyy))
(5) Was the AECAT test performed within 2 months of the application of this standard? (Yes or no)
(6) AECAT test results grade: _____ (A or B)
(7) AECAT test result: _____ (pass or fail)
(8) $CR_{external\ pitting}$ mpy
(9) If AECAT test result is a pass with no prev API fix 53, enter $CR_{external\ pitting}$ : _____ mpy
(10) If AECAT test result is a pass, generate $T_{min}$ : _____ inches
(11) If AECAT test result is a fail, enter $CR_{max}$ = 1.4 * $CR_{external\ pitting}$ : _____ mpy
(12) If AECAT test result is a fail, generate $T_{min}$ : _____ inches
(13) $CR_{max}$ to use = d*$CR_{max\ pitting}$ for no previous out-of-service API 653 internal inspection: _____ inches
(14) $T_{min}$ to use = d*$CR_{max\ pitting}$ for no previous out-of-service API 653 internal inspection: _____ inches
(15) TNI-$\alpha$ = ($T_{min}$ - $T_{MAT}$) / $CR_{max}$ for survival region A or B using the "sim of the internal and external corrosion rates"
(16) TNI-$\alpha$ can be used to determine TNI for survival age regions A and B:

FIG. 44I

This option for determining TNI-$\alpha$ cannot be used, because no previous out-of-service API 653 internal inspection exists or is suitable for use This option for determining TNI-$\alpha$ for both an AECAT test and a previous out-of-service API 653 internal inspection cannot be used Output results
(1) TNI: _____ years
(2) TNI-ER: _____ years
(3) TNI-$\alpha$ : _____ years
(4) TNI is greater than 10 years, TNI is set equal to 10 years and is re-assessed in 10 years by repeating this standard.
(5) $T_{min}$ for TNI-ER _____ inches
(6) $CR_{max}$ for TNI-ER _____ mpy
(7) $T_{min}$ for TNI-$\alpha$ _____ inches
(8) $CR_{max}$ for TNI-$\alpha$ _____ mpy

FIG. 44K

Will a previous out-of-service API 653 internal inspection be part of the additional measurements in Step 9?    This option for determining TNI-α cannot be used, because no previous out-of-service API 653

Will both an AECAT test and a previous out-of-service API 653 internal inspection be part of the additional measurements in Step 9?    This option for determining TNI-α for both an AECAT test and a previous out-of-service API 653 internal inspection cannot be used Output Results

| | | |
|---|---|---|
| TNI = | 13.5 | years |
| TNI-ER = | 8.1 | years |
| TNI-α = | 13.5 | years |
| TNI to use if TNI above is > 10 years = | 10.0 | years |
| T_min = | 0.16 | inches |
| CR_max = | 4.48 | mpy |
| T_min = | 0.16 | inches |
| CR_max = | 4.48 | mpy |

FIG. 44L

*Recommendation (circle (a), (b), or (c))*
(a) this ASTM standard method recommends that an out of service API 653 internal inspection be performed.
(b) this ASTM standard method recommends that an in-service API 653 external inspection be performed before the results of this standard be reported.

_____     _____     _____
Signature                        Name                            Date Graphs of $F_X(x)$, $F_Y(y)$, $S_Y(y)$, and $S_Y(y/t_0)$
(1) Corrosion rate Weibull distributed CDF with ($\gamma$, $\beta$ and $\eta$ ): $F_X(x)$
(2) Tank failure Weibull distributed CDF with ($\gamma$, $\beta$ and $\eta$ ): $F_X(x)$
(3) Tank survival Weibull distributed CDF with ($\gamma$, $\beta$ and $\eta$ ): $F_X(x)$
(4) Bayesian update of $S_Y(y)$ Weibull distributed CDF with ($\gamma$, $\beta$ and $\eta$ ): $S_Y(y/t_0)$

FIG. 44M

| FIG. 45A | FIG. 45B |
| FIG. 45C | FIG. 45D |
| FIG. 45E | FIG. 45F |
| FIG. 45G | FIG. 45H |
| FIG. 45I | FIG. 45J |
| FIG. 45K | FIG. 45L |
| FIG. 45M | FIG. 45N |
| FIG. 45O | |

FIG. 45

Yellow highlighted areas require an input to be entered in column D

Input parameters (1) What is the date of the application of this standard by month and year (mm,yyy): $t_{0,age}$ = _____ years (2) Determine the age of the tank in years, $t_0$, since the time of the completion of the last out-of-service API 653 internal inspection or the date when a new or refurbished tank was brought back into service: $t_0$ = _____ year (3) The mean or median measurement of the tank bottom thickness, $T_{0\,min}$, in inches, determined in step 3 of this standard at $t_0$: $T_{0\,min}$ = _____ inches (circle one: mean or median)

(4) What is the date of the completion of the last out-of-service API 653 internal inspection or the date when a new tank was brought back into service by month and year (mm, yyy)? $t_{P\,age}$ = _____ years (5) Determine the age of the tank in years, $t_P$, at the time of the completion of the last out-of-service API 653 internal inspection, or the date when a new or refurbished tank was brought back into service: (either a previous API 653 internal inspection or when the tank was new): $t_P$ = _____ years (6) The mean or median thickness of the tank bottom, $T_{P\,min}$, in inches, determined from tank bottom thickness measurements made at the last out-of-service API 653 internal inspection after maintenance and/or repairs, or re- (7) The minimum allowable thickness, $T_{MAT}$, (typically 0.05 or 0.10 inches): $T_{MAT}$ = _____ inches (8) What is $y_1 = t_0 - t_{P?}$ $y_1 = t_0 - t_P$ = _____ years Step 2 - leak detection integrity test?

(1) Was a leak detection integrity test performed? (Yes or no)

(2) What was the result of the leak detection integrity test (pass, fail)

(3) This standard method can be considered for use only if the tank of interest passes the leak detection integrity test:

FIG. 45A

Enter only the yellow highlighted areas

Date of applicate of this standard:    Month = 3    Year = 2016 t_0 = 20.0 years

T_0 min = 0.2388 in.

Date of the previous out-of-service API 653 Internal
Inspection:    Month = 3    Year = 1996 t_P = 0.0 years

T_0 min = 0.250 in.
T_MAT = 0.10 in.
y_1 = t_0 - t_P = 20.0 years

Was a leak detection integrity test performed? (Yes or No)    Yes

Leak detection integrity test result (Pass or Fail) =    Pass

Yes: Standard can be considered for use

FIG. 45B

Yes: Standard can be considered for use

Step 3 - API 653 external inspection, in-service measurements of bottom thickness, and in-service measurements of average bottom thickness and corrosion rate in the tank of interest API 653 external inspection (1) Was an in service API 653 external inspection performed? (Yes or no)?
(2) Does the results of the API 653 external inspection prohibit the use of this ASTM standard method? (Yes or no)?
(3) Will the results of the API 653 external inspection be used in this ASTM standard method? (Yes or no)?
(4) If an in-service API 653 external inspection was performed, enter the month, if available, and the year (mm,yyyy): t_Ext API 653 age: _____ year
(5) Was the in-service API 653 external inspection performed within 2 months of the application of this standard?

Yes: Standard can be considered for use

What is $T_{min}$ and $CR_{max}$ for the tank of interest do to external or bottom side pitting?

(1) $T_{AVE}$ from Step 3: _____ inches
(2) $CR_{AVE} = T_{AVE} / (t_0 - t_P)$ from Step 3: _____ mpy
(3) $CR_{Ratio}$ from Step 3:
(4) Was $T_{pitting}$ from Step 3 (a) measured directly or (b) computed from $T_{Avg}$)
(5) $CR_{max}$ Due to external pitting from step 3: _____ mpy
(6) $T_{min\,ext}$ from Step 3: _____ inches

FIG. 45C

Was and API 653 external inspection performed? (Yes or no)    Yes does the API 653 external inspection prohibit use of this
standard? (Yes or no)    no will the results of the API 653 external inspection be used
in this standard? (Yes or no)    Yes Date of the API 653 external inspection:    Month =    3    Year =    2016 was the in-service API 653 external inspection performed
within 2 months of the application of this standard?    Yes: Standard can be considered $T_{avg}$ =    0.239    inches
$CR_{avg}$ =    0.560    mpy
$CR_{ratio}$ =    8.0

Was $T_{pitting}$ (a) measured directly or (b) computed from    b
$T_{avg}$ in Step 3

$CR_{max\ pitting}$ =    4.480    mpy
$T_{min\ ext}$ =    0.160    inches

FIG. 45D (7) $CR_{max\ sum}$ from Step 3: _____ inches (8) $T_{min\ sum}$ from Step 3: _____ inches (9) Is $CR_{max}$ computed just from external or maximum corrosion or both the sum of internal and external? (External, Both)

(10) $CR_{max}$ To use for only AECAT _____ mpy

(11) $T_{min}$ to use for only AECAT _____ inches

Step 4 - Determine $F_x(x)$ to Use (1) What is the survival possibility based on the corrosion thickness of the tank bottom? $S_y(y=t0) = (T_0 - T_{MAT})/(T_P - T_{MAT})$: _____

(2) Determine $\gamma$, $\beta$ and $\eta$ for this survival probability using $CR_{max}$ following appendix 11. Plots will be generated by the worksheet.

(1) $\gamma$ =
(2) $\beta$ =
(3) $\eta$ =
(4) Mean $F_x(x)$ =
(5) StDev $F_x(x)$ =
(6) COV $F_x(x)$ =
(7) Mean $S_Y(y)$ =
(8) StDev $S_Y(y)$ =
(9) COV $S_Y(y)$ =

FIG. 45E $CR_{max\ ext + int}$ = 6.272 mpy
$T_{min\ ext + int}$ = 0.125 inches

CR assume external/maximum or both? External $CR_{max}$ to use for only AECAT = 4.48 mpy
$T_{min}$ to use for only AECAT = 0.160 inches 0.403

Survival probability based on tank bottom corrosion =
Determine $\gamma$, $\beta$ and $\eta$ for this survival probability using
$CR_{max}$ following appendix 11. Plots will be generated by
the worksheet.

$\gamma$ = -1.00
$\beta$ = 5.80
$\eta$ = 4.50

Mean FX(x) = 3.17 mpy
StDev FX(x) = 0.83 mpy
COV FX(x) = 0.26 mpy
Mean SY(y) = 18.94 years
StDev SY(y) = 4.97 years
COV SY(y) = 0.26 years

FIG. 45F

Steps 5,6,7 - Generate $F_Y(y)$, $S_Y(y/t0)$ as graphs in the Excel worksheet

Step 8 - Computation of TNI-ER (1) What is $t_0 - t_{P?}$ $t_0 - t_{P?} = $ _____ years (2) What is y equal to at the implementation of this standard $(y_1 = t_0 - t_P)$?

(3) What is the survival probability, $S_Y(y_1 = t_0 - t_P)$?

(4) What is the survival age region? (A, B, C, D) Note: Look on the $S_Y(y)$ and $S_Y(y/t0)$ graphs?

(5) $S_Y(y_2/y_1 = (t_0 - t_P))/ = [S_Y(y_1 = t_0 - t_P)]^2$ (6) What is the $y_2 = t_N - t_0$? Look up the inverse in the Excel sheet.

(7) What is TNI-ER in years $(y_2 - y_1)$?

(7a) What is TNI-ER in years $(y_2 - y_1)$ determined from equivalent risk plot?

Step 9 - Additional measurements of the entire tank bottom (1) Were additional measurements made as described in Step 9: _____ (yes or no).

TNI-α Can be determined and used if survival age region is B (1) If Yes, methods were used: (ENter all that apply beneath the letter: (a) AECAT; (b) previous out-of-service API 653 internal inspection; (c) both (a) and (b); and (d) robotic inspection.

Steps 10 and 11: Results of additional measurements made in Step 10, including determination of TNI-α

FIG. 45G $t\_0 - t\_P =$ 20.0 years
$y = t\_0 - t\_P =$ 20.0 years
$SY(y = (t\_0 - tP)) =$ 0.400
Survival Age Region = B
$SY(y = tN / y = (t0 - tP))/ = [SY(y = t0 - tP)]^{\wedge}2 =$ 0.160
$y2 = t\_N - t\_0 =$ 25.900 years
$TNI\text{-}ER = y\_2 - y\_1 =$ 5.9 years
$TNI\text{-}ER = y\_2 - y\_1 =$ 6.1 years Were additional measurements of the entire tank bottom made?   Yes TNI-α Can be determined and used if survival age region is B (a) - AECAT          (b) - prev API 653          (c) - both No          Yes          No

FIG. 45H

This option for determining TNI-α cannot be used, because no AECAT test was performed Enter the information for a previous out-of-service API 653 internal inspection Steps 9 - 11 for a previous out-of-service API 653 internal inspection (b) Previous out-of-service API 653 internal inspection (1) Is an previous out-of-service API 653 internal inspection available for use with this standard? (Yes or no)

(2) Does the results of the out-of-service API 653 internal inspection prohibit the use of this measurement option? (Yes or no)

(3) enter the month, if available, and the year: _____ (mm,dd,yyyy))

(4) if a previous out of service API 653 internal inspection performed, will it be used as part of this standard? (Enter yes or no can override the automatic response)

(5) time since the previous out-of-service API 653 internal inspection or the time since the tank was installed or maintained/repaired and brought back into service, $(t_0 - t_P)$ in years: _____ years (6) $T_{Avg}$ from Step 3 = $T_{uniform}$ : _____ inches (7) $CR_{Ratio}$ from Step 3: _____

(8) $CR_{Avg}$ from Step 3 = $CR_{uniform}$ : _____ mpy (9) $CR_{pitting}$ from Step 3: _____ mpy

(10) $T_{pitting}$ from Step 3: _____ inches

FIG. 45I

(11) $T_{avg\,prev\,API\,653}$ from a previous out-of-service API 653 internal inspection: _____ inches
(12) $CR_{avg\,prev\,API\,653}$ from a previous out-of-service API 653 internal inspection: _____ mpy
(13) $T_{min\,underside}$ from a previous out-of-service API 653 internal inspection: _____ inches
(14) $T_{min\,topside}$ from a previous out-of-service API 653 internal inspection: _____ inches
(15) $T_{min\,sum}$ from a previous out-of-service API 653 internal inspection: _____ inches
(16) $CR_{max\,underside}$ from a previous out-of-service API 653 internal inspection: _____ mpy
(17) $CR_{max\,topside}$ from a previous out-of-service API 653 internal inspection: _____ mpy
(18) $CR_{max\,sum}$ from a previous out-of-service API 653 internal inspection: _____ mpy
(19) Adjusted $T_{min\,ext} = (T_{min\,prev\,API\,653}) * (CR_{avg} / CR_{avg\,prev\,API\,653})$ for external or underside corrosion or maximum CR
(20) Adjusted $CR_{max\,ext} = (CR_{max\,prev\,API\,653}) * (CR_{avg} / CR_{avg\,prev\,API\,653})$ for external or underside corrosion or maximum
(21) Adjusted $T_{min\,sum} = (T_{min\,prev\,API\,653}) * (CR_{avg} / CR_{avg\,prev\,API\,653})$ for sum of external or underside and internal
(22) Adjusted $CR_{max\,sum} = (CR_{max\,prev\,API\,653}) * (CR_{avg} / CR_{avg\,prev\,API\,653})$ for sum of external or underside and internal
(23) Adjusted $T_{min\,max\,(ext,\,int)} = (T_{min\,prev\,API\,653}) * (CR_{avg\,Step\,3} / CR_{avg\,prev\,API\,653})$ for maximum of external or underside
(24) Adjusted $CR_{max\,max\,(ext,\,int)} = (CR_{max\,prev\,API\,653}) * (CR_{avg\,Step\,3} / CR_{avg\,prev\,API\,653})$ for maximum of external or underside
(25) $CR_{max}$ to use = (Adjusted $CR_{max\,sum} + 1.4 * CR_{max\,pitting}) / 2$: _____ mpy
(26) $T_{min}$ to use = $T_{P\,min} - (t_P - t_0) * CR_{max}$ : _____ inches
(27) $TNI\text{-}\alpha = (T_{min} - T_{MAT}) / CR_{max}$ for survival region A or B using the "sum of the internal and external corrosion rates"
(28) $TNI\text{-}\alpha$ can be used to determine TNI for survival age regions A and B:

FIG. 45K

| | | |
|---|---|---|
| $T_{avg\ prev\ API\ 653}$ = | 0.24 | |
| $CR_{avg\ prev\ API\ 653}$ = | 0.45 | |
| $T_{min\ underside\ prev\ API\ 653}$ = | 0.20 | |
| $T_{min\ topside\ prev\ API\ 653}$ = | 0.22 | |
| $T_{min\ prev\ API\ 653}$ = | 0.16 | |
| $CR_{max\ underside\ prev\ API\ 653}$ = | 2.78 | |
| $CR_{max\ topside\ prev\ API\ 653}$ = | 1.67 | |
| $CR_{max\ prev\ API\ 653}$ = | 4.44 | |
| Adjusted $T_{min}$ = $(T_{min\ API\ 653}) * (CR_{avg} / CR_{avg\ API\ 653})$ | 0.249 | |
| Adjusted $CR_{max}$ = $(CR_{max\ API\ 653}) * (CR_{avg} / CR_{avg\ API\ 653})$ | 3.457 | |
| Adjusted $T_{min}$ = $(T_{min\ API\ 653}) * (CR_{avg} / CR_{avg\ API\ 653})$ | 0.274 | |
| Adjusted $CR_{max}$ = $(CR_{max\ API\ 653}) * (CR_{avg} / CR_{avg\ API\ 653})$ | 5.531 | |
| Adjusted $T_{min}$ = $(T_{min\ API\ 653}) * (CR_{avg} / CR_{avg\ API\ 653})$ | 0.200 | |
| Adjusted $CR_{max}$ = $(CR_{max\ API\ 653}) * (CR_{avg} / CR_{avg\ API\ 653})$ | 2.074 | |
| $CR_{max}$ to use = Average [Adjusted $CR_{max\ sum}$ + 1.4 * $CR_{max\ pitting}$] | 5.901 | |
| $T_{min}$ to use = $T_{P\ min} - (t_P - t_0) * CR_{max}$ = | 5.42 | |
| $TNI-\alpha = (T_{min} - T_{MAT}) / CR_{max}$ for No AECAT = | | |
| $TNI-\alpha$ to use = | 5.4 | |

Year = 1996 years
inches
mpy
mpy

FIG. 45L

This option for determining TNI-α for both an AECAT test and a previous out-of-service API 653 internal inspection CANNOT be used Output results
(1) TNI: _____ years
(2) TNI-ER: _____ years
(3) TNI-α : _____ years
(4) TNI is greater than 10 years, TNI is set equal to 10 years and is re-assessed in 10 years by repeating this standard.
(5) $T_{min}$ for TNI-ER _____ inches
(6) $CR_{max}$ for TNI-ER _____ mpy
(7) $T_{min}$ for TNI-α _____ inches
(8) $CR_{max}$ for TNI-α _____ mpy

FIG. 45M

Will both an AECAT test and a previous out-of-service API 653 internal inspection be part of the additional measurements in Step 9?

This option for determining TNI-α for both an AECAT test and a previous out-of-service API 653 internal inspection cannot be used Output Results
TNI = 8.1 years
TNI-ER = 8.1 years
TNI-α = 5.4 years TNI to use if TNI above is > 10 years =
T_min = 8.1 years
CR_max = 0.16 inches
T_min = 4.48 mpy
CR_max = 0.13 inches
       = 5.90 mpy

FIG. 45N

*Recommendation (circle (a), (b), or (c))*
(a) this ASTM standard method recommends that an out of service API 653 internal inspection be performed.
(b) this ASTM standard method recommends that an in-service API 653 external inspection be performed before the results of this standard be reported.

Signature _____ Name _____ Date _____

Graphs of $F_X(x)$, $F_Y(y)$, $S_Y(y)$, and $S_Y(y/t_0)$ (1) Corrosion rate Weibull distributed CDF with ($\gamma$, $\beta$ and $\eta$): $F_X(x)$
(2) Tank failure Weibull distributed CDF with ($\gamma$, $\beta$ and $\eta$): $F_X(x)$
(3) Tank survival Weibull distributed CDF with ($\gamma$, $\beta$ and $\eta$): $F_X(x)$
(4) Bayesian update of $S_Y(y)$ Weibull distributed CDF with ($\gamma$, $\beta$ and $\eta$): $S_Y(y/t_0)$

FIG. 45O

| FIG. 46A | FIG. 46B |
| FIG. 46C | FIG. 46D |
| FIG. 46E | FIG. 46F |
| FIG. 46G | FIG. 46H |
| FIG. 46I | FIG. 46J |
| FIG. 46K | FIG. 46L |
| FIG. 46M | |

FIG. 46

Yellow highlighted areas require an input to be entered in column D

Input parameters (1) What is the date of the application of this standard: by month and year (mm,yyy): $t_{0,age}$: _____ years (2) Determine the age of the tank in years, $t_0$, since the time of the completion of the last out-of-service API 653 internal inspection or the date when a new or refurbished tank was brought back into service: $t_0$ = _____ year (3) The mean or median measurement of the tank bottom thickness, $T_{0\,min}$, in inches, determined in step 3 of this standard at $t_0$: $T_{0\,min}$ = _____ inches (circle one: mean or median)

(4) What is the date of the completion of the last out-of-service API 653 internal inspection or the date when a new tank was brought back into service by month and year (mm, yyy)? $t_{P\,age}$ : = _____ years (5) Determine the age of the tank in years, $t_P$, at the time of the completion of the last out-of-service API 653 internal inspection, or the date when a new or refurbished tank was brought back into service: (either a previous API 653 internal inspection or when the tank was new): $t_P$ = _____ years (6) The mean or median thickness of the tank bottom, $T_{P\,min}$, in inches, determined from tank bottom thickness measurements made at the last out-of-service API 653 internal inspection after maintenance and/or repairs, or re- (7) The minimum allowable thickness, $T_{MAT}$, (typically 0.05 or 0.10 inches): $T_{MAT}$ = _____ inches (8) What is $y_1 = t_0 - t_{P?}$  $y_1 = t_0 - t_P$ = _____ years Step 2 - leak detection integrity test?

(1) Was a leak detection integrity test performed? (Yes or no)
(2) What was the result of the leak detection integrity test (pass, fail)
(3) This standard method can be considered for use only if the tank of interest passes the leak detection integrity test:

FIG. 46A

Enter only the yellow highlighted areas.

Date of applicate of this standard: Month = 3  Year = 2016 t_0 = 20.0 years

T_0 min = 0.2388 in.

Date of the previous out-of-service API 653 Internal
Inspection: Month = 3  Year = 1996 t_P = 0.0 years

T_0 min = 0.250 in.
T_MAT = 0.10 in.
y_1 = t_0 - t_P = 20.0 years

Was a leak detection integrity test performed? (Yes or No) = Yes

Leak detection integrity test result (Pass or Fail) = Pass

Yes: Standard can be considered for use

FIG. 46B

Yes: Standard can be considered for use

Step 3 - API 653 external inspection, in-service measurements of bottom thickness, and in-service measurements of average bottom thickness and corrosion rate in the tank of interest API 653 external inspection (1) Was an in service API 653 external inspection performed? (Yes or no)?
(2) Does the results of the API 653 external inspection prohibit the use of this ASTM standard method? (Yes or no)?
(3) Will the results of the API 653 external inspection be used in this ASTM standard method? (Yes or no)?
(4) If an in-service API 653 external inspection was performed, enter the month, if available, and the year (mm,yyyy): t_Ext API 653 age: _____ year
(5) Was the in-service API 653 external inspection performed within 2 months of the application of this standard?

Yes: Standard can be considered for use

What is $T_{min}$ and $CR_{max}$ for the tank of interest do to external or bottom side pitting?

(1) $T_{AVE}$ from Step 3: _____ inches
(2) $CR_{AVE} = T_{AVE} / (t_0 - t_P)$ from Step 3: _____ mpy
(3) $CR_{Ratio}$ from Step 3: _____
(4) Was $T_{pitting}$ from Step 3: (a) measured directly or (b) computed from $T_{Avg}$)

(5) $CR_{max}$ Due to external pitting from step 3: _____ mpy
(6) $T_{min\ ext}$ from Step 3: _____ inches

FIG. 46C

Was and API 653 external inspection performed? (Yes or no)     Yes does the API 653 external inspection prohibit use of this standard? (Yes or no)     no will the results of the API 653 external inspection be used in this standard? (Yes or no)     Yes Date of the API 653 external inspection:    Month = 3    Year = 2016 was the in-service API 653 external inspection performed within 2 months of the application of this standard?     Yes: Standard can be considered $T_{avg}$ = 0.239    inches
$CR_{avg}$ = 0.560    mpy
$CR_{ratio}$ = 8.0

Was $T_{pitting}$ (a) measured directly or (b) computed from $T_{avg}$ in Step 3     b $CR_{max\ pitting}$ = 4.480    mpy
$T_{min\ ext}$ = 0.160    inches

FIG. 46D (7) $CR_{max\ sum}$ from Step 3: _____ inches (8) $T_{min\ sum}$ from Step 3: _____ inches (9) Is $CR_{max}$ computed just from external or maximum corrosion or both the sum of internal and external? (External, Both)

(10) $CR_{max}$ To use for only AECAT _____ mpy

(11) $T_{min}$ to use for only AECAT _____ inches

Step 4 - Determine $F_x(x)$ to Use (1) What is the survival possibility based on the corrosion thickness of the tank bottom? $S_y(y=t0) = (T_0 - T_{MAT}) / (T_P - T_{MAT})$: _____

(2) Determine $\gamma$, $\beta$ and $\eta$ for this survival probability using $CR_{max}$ following appendix 11. Plots will be generated by the worksheet.

(1) $\gamma =$
(2) $\beta =$
(3) $\eta =$
(4) Mean $F_x(x) =$
(5) StDev $F_x(x) =$
(6) COV $F_x(x) =$
(7) Mean $S_Y(y) =$
(8) StDev $S_Y(y) =$
(9) COV $S_Y(y) =$

FIG. 46E

| | | |
|---|---:|---|
| $CR_{max\,ext+int}$ = | 6.272 | mpy |
| $T_{min\,ext+int}$ = | 0.125 | inches |
| CR assume external/maximum or both? | External | |
| $CR_{max}$ to use for only AECAT = | 4.48 | mpy |
| $T_{min}$ to use for only AECAT = | 0.160 | inches |
| Survival probability based on tank bottom corrosion = | 0.403 | |

Determine $\gamma$, $\beta$ and $\eta$ for this survival probability using $CR_{max}$ following appendix 11. Plots will be generated by the worksheet.

| | | |
|---|---:|---|
| $\gamma$ = | -1.00 | |
| $\beta$ = | 5.80 | |
| $\eta$ = | 4.50 | |
| Mean FX(x) = | 3.17 | mpy |
| StDev FX(x) = | 0.83 | mpy |
| COV FX(x) = | 0.26 | mpy |
| Mean SY(y) = | 18.94 | years |
| StDev SY(y) = | 4.97 | years |
| COV SY(y) = | 0.26 | years |

FIG. 46F

Steps 5,6,7 - Generate $F_Y(y)$, $S_Y(y/t0)$ as graphs in the Excel worksheet

Step 8 - Computation of TNI-ER (1) What is $t_0 - t_{P?}$ $t_0 - t_{P?}$ = _____ years
(2) What is y equal to at the implementation of this standard ($y_1 = t_0 - t_P$)?
(3) What is the survival probability, $S_Y(y_1 = t_0 - t_P)$?
(4) What is the survival age region? (A, B, C, D) Note: Look on the $S_Y(y)$ and $S_Y(y/t0)$ graphs?
(5) $S_Y(y_2 = t_N / y_1 = (t_0 - t_P)) / = [S_Y(y_1 = t_0 - t_P)]^2$
(6) What is the $y_2 = t_N - t_0$? Look up the inverse in the Excel sheet.
(7) What is TNI-ER in years ($y_2 - y_1$)?
(7a) What is TNI-ER in years ($y_2 - y_1$) determined from equivalent risk plot?

Step 9 - Additional measurements of the entire tank bottom (1) Were additional measurements made as described in Step 9: _____ (yes or no)

TNI-α Can be determined and used if survival age region is B (1) If Yes, methods were used: (ENter all that apply beneath the letter; (a) AECAT; (b) previous out-of-service API 653 internal inspection; (c) both (a) and (b); and (d) robotic inspection:

Steps 10 and 11: Results of additional measurements made in Step 10, including determination of TNI-α

FIG. 46G

| | | |
|---|---|---|
| $t\_0 - t\_P =$ | 20.0 | years |
| $y = t\_0 - t\_P =$ | 20.0 | years |
| $SY(y = (t\_0 - tP)) =$ | 0.400 | |
| Survival Age Region = | B | |
| $SY(y = tN / y = (t0 - tP))/ = [SY(y = t0 - tP))^{\wedge}2 =$ | 0.160 | years |
| $y2 = t\_N - t\_0 =$ | 25.900 | years |
| TNI-ER = $y\_2 - y\_1 =$ | 5.9 | years |
| TNI-ER = $y\_2 - y\_1 =$ | 6.1 | years |

Were additional measurements of the entire tank bottom made? Yes

TNI-α Can be determined and used if survival age region is B (a) - AECAT  (b) - prev API 653  (c) - both

Yes  Yes

FIG. 46H

This option for determining TNI-α cannot be used, because no AECAT test was performed
Enter the information for a previous out-of-service API 653 internal inspection Steps 9 - 11 for both an AECAT and a previous out-of-service API 653 internal inspection
(c) Both (a) and (b)

Determine CR max CR min to Use with or without AECAT and a previous Out-of-service API 653 Internal Inspection
(1) PASS or FAIL an external API 653 inspection? (PASS or FAIL)
(2) Was an AECAT performed?
(3) PASS or FAIL an AECAT? (PASS or FAIL)
(4) Is a previous API 653 report available to be used? (yes or no)
(5) Will both the AECAT and the previous API 653 report be used? (yes or no)
(6) Do both the AECAT and the previous out-of-service API 653 internal inspection meet the criteria of this standard to be used as a measurement option in Step 9?
(7) What is the survival age region? (A, B, C, D)
(8) $CR_{max}$ : _____ mpy from table 14
(9) $T_{min}$ : _____ inches
(10) MRT : _____ inches
(11) TNI-α : _____ years or "Recommend out-of-service API 653 internal inspection" if MRT < 0.0 in.
(12) What is CRmax and Tmin for the tank interest determined by table 14 for AECAT and a previous out-of-service
(13) TNI-α Can be used to determine TNI for survival age regions A and B:

FIG. 46I

Will both an AECAT test and a previous out-of-service API 653 internal inspection be part of the additional measurements in Step 9?

This information for an AECAT test and previous out of service API 653 internal inspection to determine TNI-α

PASS or FAIL an external API 653 inspection?    Pass

Was an AECAT performed?    Yes    Year =

PASS or FAIL an AECAT?    Pass

Is a previous API 653 report available to be used? (yes or no)    Yes

Will both the AECAT and the previous API 653 report be used? (yes or no)    Yes

Do both the AECAT and the previous out-of-service API 653 internal inspection meet the criteria of this standard to be used as a measurement option in Step 9?    Yes Survival age region =    B $CR_{max}$ from table 14 =    4.4    mpy $T_{min}$ =    0.16    inches MRT =    13.8    years TNI-α =    13.8    mpy TNI from table 14 for survival age regions A and B TNI-α to use =    13.8    mpy

FIG. 46J

Output results
(1) TNI: _____ years
(2) TNI-ER: _____ years
(3) TNI-α : _____ years
(4) TNI is greater than 10 years, TNI is set equal to 10 years and is re-assessed in 10 years by repeating this standard.
(5) T$_{min}$ for TNI-ER _____ inches
(6) CR$_{max}$ for TNI-ER _____ mpy
(7) T$_{min}$ for TNI-α _____ inches
(8) CR$_{max}$ for TNI-α _____ mpy

FIG. 46K

| Output Results | | |
|---|---|---|
| TNI = | 13.8 | years |
| TNI-ER = | 8.1 | years |
| TNI-α = | 13.8 | years |
| TNI to use if TNI above is > 10 years = | 10.0 | years |
| T_min = | 0.16 | inches |
| CR_max = | 4.48 | mpy |
| T_min = | 0.16 | inches |
| CR_max = | 4.44 | mpy |

FIG. 46L

*Recommendation (circle (a), (b), or (c))*
(a) this ASTM standard method recommends that an out of service API 653 internal inspection be performed.
(b) this ASTM standard method recommends that an in-service API 653 external inspection be performed before the results of this standard be reported.

_____  _____  _____
Signature                  Name                       Date

Graphs of $F_X(x)$, $F_Y(y)$, $S_Y(y)$, and $S_Y(y/t_0)$
(1) Corrosion rate Weibull distributed CDF with ($\gamma$, $\beta$ and $\eta$ ): $F_X(x)$
(2) Tank failure Weibull distributed CDF with ($\gamma$, $\beta$ and $\eta$ ): $F_X(x)$
(3) Tank survival Weibull distributed CDF with ($\gamma$, $\beta$ and $\eta$ ): $F_X(x)$
(4) Bayesian update of $S_Y(y)$ Weibull distributed CDF with ($\gamma$, $\beta$ and $\eta$ ): $S_Y(y/t_0)$

FIG. 46M

MEASUREMENT-BASED, IN-SERVICE METHOD FOR DETERMINING THE TIME TO THE NEXT INTERNAL INSPECTION OF AN AST

RELATED APPLICATIONS

This application claims priority to U.S. Provisional Patent Application Ser. No. 62/324,099 filed on Apr. 18, 2016, and is incorporated by reference herein.

FIELD OF THE INVENTION

The methods of the present invention can be used for quantitatively determining the time (TNI) between (1) the application of this method and (2) the time at which the next out-of-service API 653 internal inspection (see Appendix 14 for a definition of an Internal Inspection of a Tank) of a steel, field-erected, aboveground storage tank (AST) should be performed. These methods can be applied to a single tank containing refined petroleum products and can be used at any time during the service life of a tank to check or update the internal inspection interval specified in API 653 for the next out-of-service internal inspection. This method can be applied directly to the tank of interest (see Appendix 14 for a definition of the Tank of Interest) and does not require a control tank or detailed knowledge about some or all of the tanks in the facility to implement. TNI is based on a comprehensive set of measurements made on the tank of interest to determine the condition (thickness, corrosion rate, and integrity) of the tank bottom (or floor). This method uses the minimum allowable thickness, $T_{MAT}$, of the tank bottom, as defined in API 653, to determine when the tank should be taken out-of-service for a full API 653 internal inspection. Up to five different in-service measurements, tests, or inspections, which are currently used by the petroleum industry, are made and used in the determination of TNI. The data and test/inspection results from these five sources and an empirical corrosion rate cumulative frequency distribution (CFD) are then combined and used in a novel way to determine TNI. The analysis methods used in this method are similar to the Bayesian methods used by the life insurance industry to determine life expectancy, or by a company to determine the period of a warranty (i.e., life expectancy) of its products, but these methods are used very differently to determine TNI. These methods have substantial operational, cost-saving, and environment benefits and are relevant to a variety of important internal inspection applications for ASTs.

TNI is determined by appropriately combining two estimates of TNI (TNI-ER and TNI-α). TNI-ER determines the time to the next out-of-service internal inspection without any additional risk of tank bottom failure (as defined by $T_{MAT}$). During this entire time interval, TNI-ER, the risk or probability of tank bottom failure, is lower than determined at the time of the application of the method. It is based on a Bayesian update of the probability of survival of the tank bottom and is determined using a novel method called Equivalent Risk (see Appendix 14 for a definition of Equivalent Risk). If the probability of survival of the tank bottom is high and if additional measurements of the tank bottom are available that meet the criteria in this method, a second estimate of TNI (i.e., TNI-α) can be made and combined with TNI-ER to determine TNI.

These methods can also be applied to bulk underground storage tanks (bulk USTs) with a flat bottom like those owned and operated by the US Department of Defense (DoD), and they can also be applied to shop-fabricated steel ASTs. These methods focus on refined petroleum applications, but they can be applied to water tanks and a wide range of other tanks containing liquid products where tank bottom corrosion is the major failure mechanism. In addition to API 653, these methods can be used to estimate the time interval to the next inspections as described in similar standards such as API12R1, STI SP001, and other out-of-service inspection recommended practices and methods, where the corrosion rate CFD of the tank bottom can be generated.

Appendices A15 and A15 define all of the variables and the important abbreviations used in this patent.

BRIEF DESCRIPTION OF THE PRIOR ART

There are several recommended practices or methods for inspecting the integrity of welded or riveted, steel, atmospheric-pressure, aboveground storage tanks (ASTs) after they have been placed in service. API 653 covers the maintenance inspection, repair, alteration, relocation, and reconstruction of petroleum tanks containing refined petroleum fuels. It is a performance-based inspection with the time between inspections being 10 years or more for out-of-service internal inspections, where the tank bottom can be inspected, and 5 years or less for in-service external inspections (see Appendix 14 for a definition for an External Inspection of a Tank), where the tank bottom is not accessible for inspection. The scope of this API publication is limited to the tank foundation, bottom, shell, structure, roof, attached appurtenances, and nozzles to the face of the first flange, first threaded joint, or first welding-end connection. While it can be used for inspecting shop-fabricated tanks, it is mainly intended for field-erected ASTs. It is also used for many of the military's large, bulk underground storage tanks owned or operated by the US Department of Define (DoD). In September 2000, the Steel Tank Institute (STI SP001) published a method for inspection and repair of shop-fabricated steel tanks. The STI method addresses double wall tanks and tanks with integral secondary containment pans as well as horizontal tanks; none of these tanks are within the scope of API 653. This method includes a risk-based approach to inspections, where tanks with the most risk requiring more frequent inspections. The risk-based approach is a function of the size, containment, release prevention and detection, and corrosion history of the tank. Internal Inspection of a Tank—A formal, complete inspection, as supervised by an authorized/certified inspector, of all accessible internal tank surfaces. The main intent of the internal inspection is to ensure that the tank bottom is not severely corroded or leaking and to gather the data necessary for the minimum bottom, shell, and roof thickness assessments. For petroleum tanks storing refined products, this is performed in accordance with API 653.

An Internal Inspection of a Tank is a formal, complete inspection, as supervised by an authorized/certified inspector, of all accessible internal tank surfaces. The main intent of the internal inspection is to ensure that the tank bottom is not severely corroded or leaking and to gather the data necessary for the minimum bottom, shell, and roof thickness assessments. For petroleum tanks storing refined products, this is performed in accordance with API 653.

In general, API 653 and most regulatory agencies require an out-of-service inspection every 10 years unless the tank is in good shape (i.e., no maintenance or repairs are needed), has certain protective features or secondary containment, the corrosion rate is low, and the minimum required thickness of the tank floor will not be exceeded during the interval between internal inspections (typically, 10 years). An out-of-service inspection is very expensive, not only because of the inspection itself, but because the maintenance and repairs made and the loss of the tank for operations during the inspection, repairs, and maintenance activities are expensive. The out-of-service inspection interval, i.e., the time until the tank must be taken out of service and inspected internally is determined from API 653 or equivalent standards. This internal inspection interval determines the maximum corrosion rate for the underside and the topside of the tank bottom from the minimum tank bottom thickness of the underside and topside before maintenance and repairs were made. The maximum corrosion rates of the underside and topside corrosion rate are added together, and this sum is then used to computed this time interval based on the thickness of the tank bottom after the maintenance and repairs were made and after subtracting the minimum allowable thickness of the tank bottom, $T_{MAT}$. $T_{MAT}$ is 0.10 in. for tanks without a release prevention barrier (RPB) and 0.05 in. with a RPB. Thus, if the tank bottom after maintenance and repairs is 0.25 in., the internal inspection interval is determined assuming only 0.15 in. or 0.20 in. could corrode before that the tank needs to be taken out-of-service and internally inspected following API 653, or equivalent.

The internal inspection interval computed in this fashion is extremely conservative and the tank bottoms often do not need any maintenance or repairs when the time for another out-of-service API 653 internal inspection occurs. This method and apparatuses based on this method presented herein allow the tank owner/operator to check the condition of the tank bottom using an in-service inspection to determine whether or not there is useful life left in the tank bottom. If there is, then the internal inspection interval computed using API 653 can be updated and used to schedule the next out-of-service API 653 internal inspection. This method recommends that a current API 653 external inspection be reviewed or performed at the same time to minimize the possibility of other non-tank-bottom issues that might require taking the tank out-of-service for an internal inspection. If a previous API 653 external inspection is used, it should be current, i.e., within 5 years of the previous external inspection, or this method should not be applied. This method recommends performing a new API 653 internal inspection if the previous external inspection is older than 4 years. While not required, this method highly recommends that an API 653 External Inspection be included when applying this method.

Loo [11] reported on a study of 148 aboveground storage tanks inspected using an acoustic emissions (AE) method of assessing the corrosion activity in the floor of an aboveground storage tank while in-service. The AE results for each of these 148 tanks were compared to the results of an internal tank floor inspection performed as part of an out-of-service inspection to verify the results of the AE test. Of the 148 tanks, 33 were crude tanks and 115 were refined product tanks. The results were summarized in FIG. 2 of Loo's paper. The results of the internal inspections (i.e., the actual or true condition of the tank) were reported in terms of four categories (FU1, FU2, FU3, and FU4). The results of the AE tests, which were reported in terms of five corrosion grades from A to E (as defined below), were compared to the out-of-service inspection results. Analysis of the results of the out-of-service internal inspections indicated that no maintenance or repairs were required on the tank bottom in 64.2% of the tanks tested. This suggests that the internal inspection interval was too conservative and could have been longer. Furthermore, 58% of all of the tanks tested with the AE test that did not need maintenance or repairs of the tank bottom could be identified with the AE test. These test results verify the fact that the internal inspection interval could be longer if it could be reliably checked. The methods of the present invention provide methods to check or update this inspection interval. These methods apply to a wide variety of tanks containing a wide variety of different types of products/liquids, particularly petroleum fuels and water.

The methods of the present invention have very substantial environmental, operational, cost-saving and cost avoidance benefits. For example, the enviromnental risk associated with the potential release of petroleum vapors associated with opening and emptying the tank for an out-of-service internal inspection is eliminated. Also, this method reduces the operational downtime per tank from weeks or months, which is required for an out-of-service API 653 internal inspection, to a day or two, which is required to implement this method. The cost savings associated with the application of this method are real, immediate, and substantial and could be over 80 to 90% of the total cost of an out-of-service API 653 internal, which includes both the inspection and any maintenance or repairs. The cost savings can be calculated from the difference in cost between the application of this method and the performance of an out-of-service internal inspection, before considering the loss of revenue due to the operational downtime required to perform the internal inspection. Finally, this method minimizes avoidance costs such as the eventual cleanup costs associated with a leak that may have gone undetected.

These methods of the present invention are based on the methods and apparatuses taught by Maresca and Maresca, et. al., in U.S. Pat. No. 9,228,932 and at least four pending patent applications: (1) "A Method and Apparatus for Extending the Time Between Out-of-Service, In-Tank Inspections," (2) "A Method and Apparatus for Determining the Time Between Internal Inspections of a Tank," (3) "A Method and Apparatus for an In-Service Measurement of the Bottom Thickness and Corrosion Rate of a Tank Bottom," and (4) "A Measurement-based, In-service Method for Updating the Internal Inspection Interval of an AST." The methods of the present invention describe methods for determining the time until the next internal inspection (TNI) by and combining the Bayesian survival probability approach taught in these patents to determine TNI-ER using Equivalent Risk and TNI-a Determined from additional measurements of the entire tank bottom for higher survival probability tank bottoms.

Equivalent Risk is a new term that is used in previous patents and patent applications by Maresca and Maresca, et. al. to determine the time from the application of this method until the time that the next out-of-service internal inspection can be performed without any additional risk or probability of tank bottom failure. It is determined from the underlying survival probability distribution of the tank bottom and a Bayesian updated survival probability distribution of the tank bottom that is developed at the time when and once the integrity of the tank bottom is verified. It is the time that it takes for the survival probability of the updated Bayesian survival probability distribution to decrease to the survival probability of the underlying probability distribution at the time of the application of this method.

SUMMARY OF THE INVENTION

It is the object of this invention to provide methods for accurately and reliably determining or updating the time until or between out-of-service inspections, TNI, using an in-service, quantitative measurement method to determine the integrity, corrosion rate, and thickness of the tank bottom.

It is the object of this invention to provide methods for accurately and reliably determining or updating the time until or between out-of-service inspections, TNI, by combining the results of in-service measurements of the tank bottom to determine TNI-ER using a Bayesian survival approach with in-service measurements of integrity, corrosion rate, and bottom thickness and TNI-α using additional measurements of the entire tank bottom using the results of an AE corrosion activity test or a previous out-of-service API 653 internal inspection report, or equivalent.

It is the object of this invention to provide methods for accurately and reliably determining or updating the time until or between out-of-service inspections, TNI, where the integrity of the tank is determined by passing a leak detection integrity test.

The preferred method of the present invention can be used to determine or update the time until the next out-of-service inspection of an aboveground storage tank (AST) or a bulk underground storage tank (UST) based on in-service measurements of the tank bottom to determine TNI from the combination of TNI-ER and TNI-α. TNI-ER is based on a Bayesian survival analysis approach to determine the time, TNI-ER, between the underlying survival probability of a tank and the same survival probability in the future once it can be determined that the tank bottom has survived, i.e., has integrity, to the time that this method is being applied. Survival, i.e., integrity, is determined by passing a leak detection test. The underlying survival probability distribution and the Bayesian update of this survival probability distribution are determined by in-service measurements of the bottom thickness and corrosion rate made at one or more location in the tank. TNI-α is determined by combining additional in-service measurements of the entire tank bottom with these local measurements. These additional measurements include the results of an in-service acoustic emission (AE) corrosion activity test where the results indicate little or no corrosion or one or more previous out-of-service API 653 internal inspections where the thickness and corrosion rate is determined from many tank floor thickness measurements over the entire floor, or a combination of both.

The preferred method of measuring thickness of the tank floor is to use one or more ultrasonic thickness (UT) sensing or measurement sensors or measurement probes on a vertical staff that is inserted into the tank from an opening at the top of the tank. The preferred method of performing AE corrosion activity test is by placing one or more, and preferably three or more, sensors in the product inside the tank on the staff, where at least one of the sensors is at a different elevation than the other sensors. Alternatively, the AE sensors can be placed on the outside wall of an AST. All of these proposed measurement procedures have been used for tank integrity assessments for many years, but they have not been used for in-service inspections or in combination to estimate the thickness and corrosion rate for the entire tank floor. The preferred method of the present invention for determining integrity is comprised of a mass-based leak detection test (Vista Precision Solution's LRDP) with a reference sensor tube inserted into the tank at a convenient opening from the top of the tank. For double-bottom tanks, a pressure decay method is the preferred method (Vista Precision Solution's Double-Bottom Pressure Decay Method).

IN THE DRAWINGS

FIG. 1 illustrates an overview flow chart of the six major activities to implement this method.

FIG. 2 illustrates the Cumulative Frequency Distributions (CFDs) of the mean corrosion data obtained over an 18-year period at 47 different locations in the US and partitioned in ~2-year groups of years after burial. The corrosion rate was determined from an average of the maximum penetration depth on two replicate samples. The maximum penetration on these samples was typically 10 times greater than the average loss of material due to corrosion.

FIG. 3 illustrates a plot of the mean, method deviation, and coefficient of variation (method deviation divided by mean) of the corrosion data for each 2-years group in FIG. 2.

FIG. 4 illustrates a Cumulative Frequency Distribution (CFD) of a corrosion rate CFD used to generate $F_X(x)$ in Step 4 of this method generated from the maximum pitting for the pitting corrosion rates between 0 and 17 mpy obtained at all 47 locations during the sampling period between 9.6 and 12.1 years after sample burial.

FIG. 5 illustrates a Cumulative Frequency Distribution (CFD) of a corrosion rate CFD used to generate $F_X(x)$ in Step 4 of this method generated from the maximum pitting for the pitting corrosion rates between 0 and ≤4 mpy obtained at all 47 locations during the sampling period between 9.6 and 12.1 years after sample burial.

FIG. 6 illustrates a Cumulative Frequency Distribution (CFD) of a corrosion rate CFD used to generate $F_X(x)$ in Step 4 of this method generated from the maximum pitting for the pitting corrosion rates between 4 and ≤8 mpy obtained at all 47 locations during the sampling period between 9.6 and 12.1 years after sample burial.

FIG. 7 illustrates a Cumulative Frequency Distribution (CFD) of a corrosion rate CFD used to generate $F_X(x)$ in Step 4 of this method generated from the maximum pitting for the pitting corrosion rates between 8 and ≤12 mpy obtained at all 47 locations during the sampling period between 9.6 and 12.1 years after sample burial.

FIG. 8 illustrates a Cumulative Frequency Distribution (CFD) of a corrosion rate CFD used to generate $F_X(x)$ in Step 4 of this method generated from the maximum pitting for the pitting corrosion rates between 12 and ≤17 mpy obtained at all 47 locations during the sampling period between 9.6 and 12.1 years after sample burial.

FIG. 9 illustrates Cumulative Frequency Distributions (CFDs) of the mean raw uniform corrosion rate and the mean and raw maximum pitting corrosion rate CFDs used to generate $F_X(x)$ in Step 4 of this method generated from the maximum pitting for the pitting corrosion rates between 4 and 8 mpy-obtained at all 47 locations during the sampling period between 9.6 and 12.1 years after sample burial. The main difference is the addition of more samples in the lower and higher tails of the CFDs. The raw corrosion rate data is comprised of the individual samples from the 8 replicates, and the mean corrosion rate data is comprised of the average of the 8 replicates. This plot provides several ways to relate the maximum pitting corrosion rate to the uniform corrosion rate measured in Step 3. This can be done using the ratio between the uniform and maximum pitting corrosion rates at a cumulative frequency of 50% or cumulative frequency of the tank bottom failure CFD at the time of the measurement.

Figure 16A:
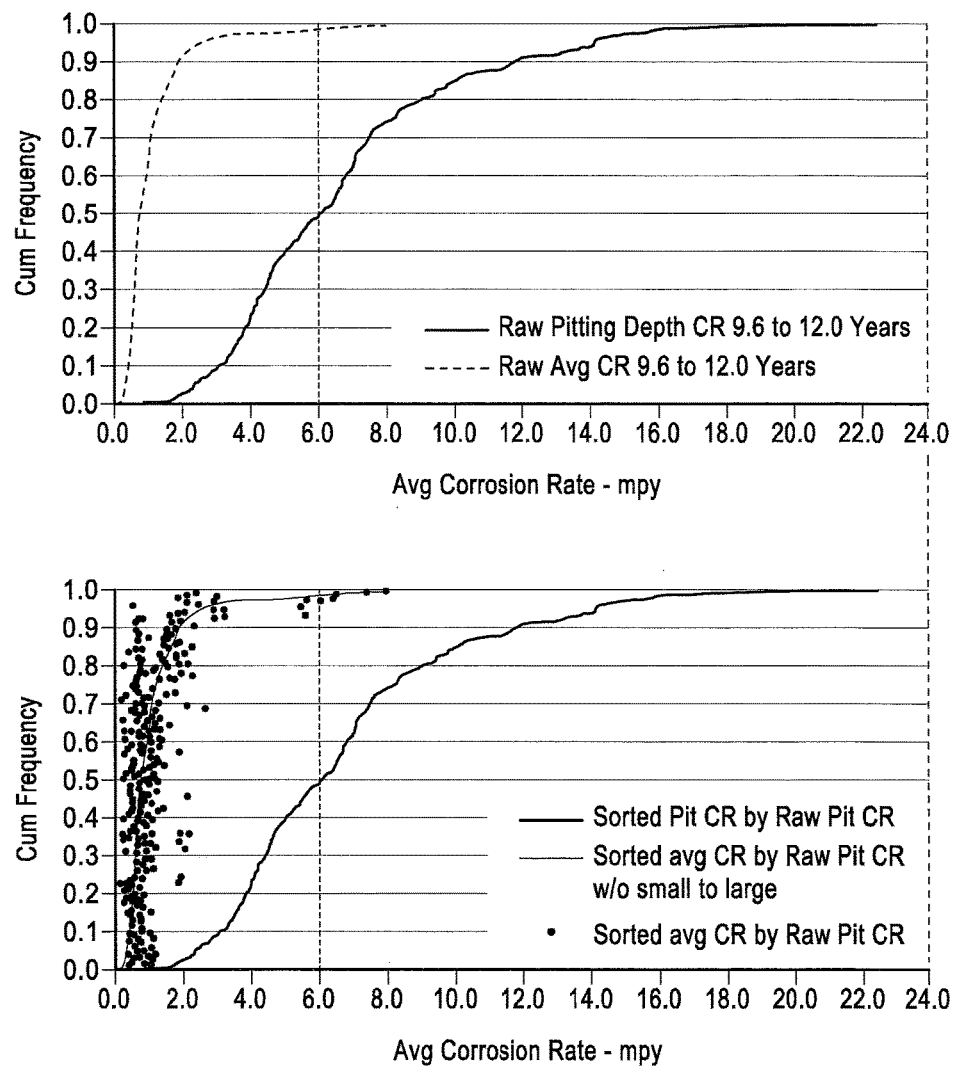
Figure 16B:
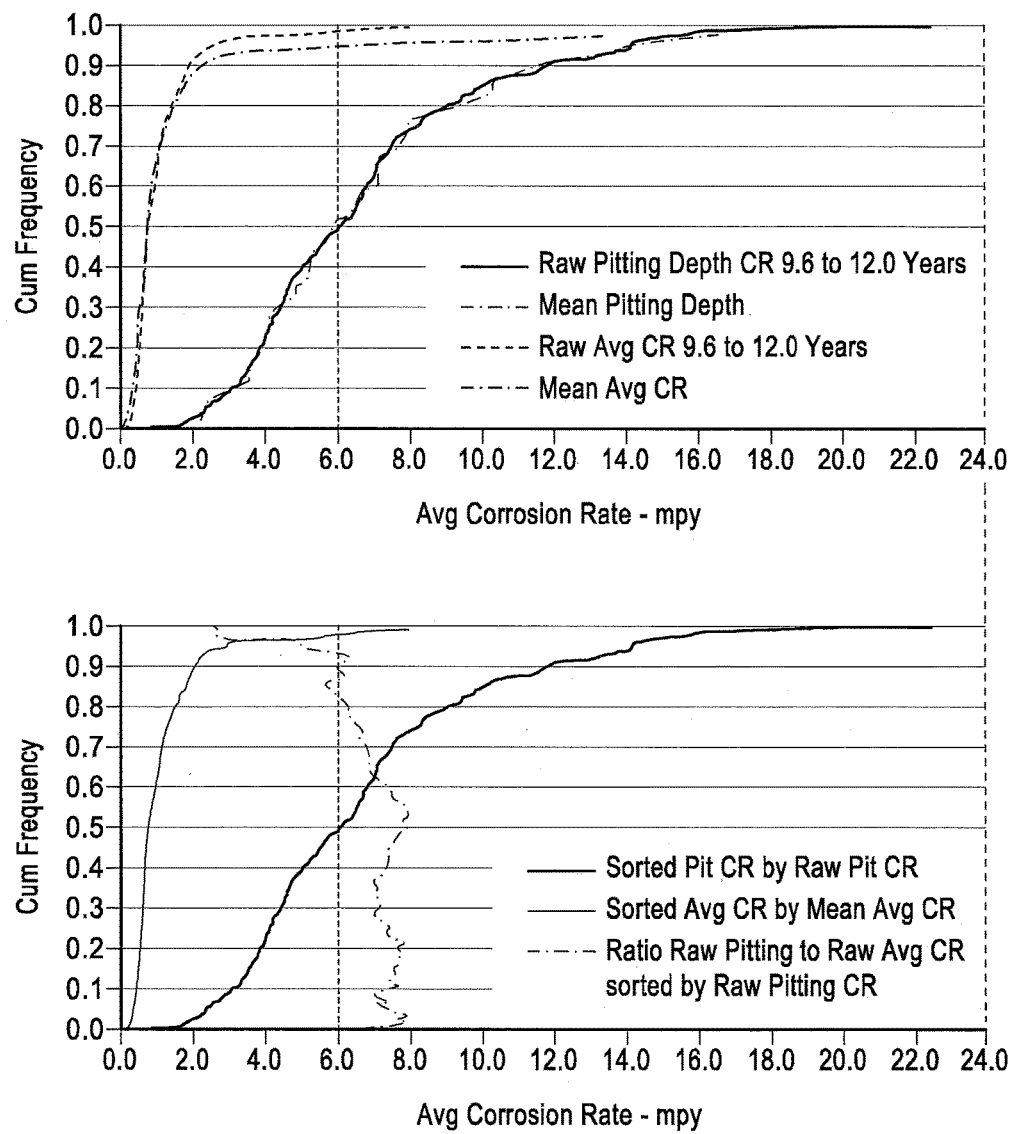

FIG. 16 illustrates $F_X(x)$ generated for 336 samples of the average and maximum pitting depth determined from the replicate samples obtained during the period 9.6 to 12.4 years after burial. Samples were obtained from 42 of the 47 burial sites throughout the United States. (A) raw $CR_{pit}$ and raw $CR_{uniform}$ were individual sorted from smallest to largest; (B) $CR_{pit}$ and raw $CR_{uniform}$ were sorted together by $CR_{pit}$ and then plotted; (C) the mean and raw corrosion rate were plotted after coring the mean and raw pitting corrosion rate was sorted by the raw corrosion rate and the mean and raw uniform corrosion rate was sorted by the raw uniform corrosion rate (the $<CR_{pitting}>$ and raw $CR_{pitting}$ sorted by raw $CR_{pitting}$ and the $<CR_{uniform}>$ and raw $CR_{uniform}$ sorted by raw $CR_{uniform}$), and (D) the ratio of the raw $CR_{pitting}$ and raw $CR_{uniform}$, samples, $CR_{ratio\{Pit\ to\ Uniform\}}$, was computed and plotted as a function of cumulative frequency were computed, where the pitting corrosion rates, raw $CR_{pitting}$, were generally 6 to 8 times larger than the uniform corrosion rates, raw $CR_{uniform}$.

Figure 17:
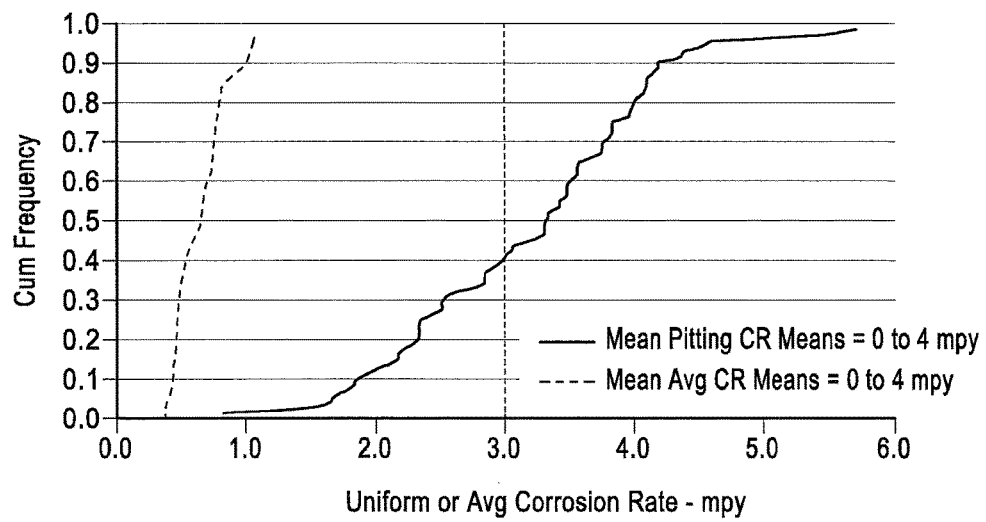

FIG. 17 illustrates a $F_X(x)$ generated by using the maximum pitting depth from all eight of the replicates at each site in FIG. 16 when sorted by the mean of the eight replicate samples with means between 0 and ≤4 mpy. The total number of replicate samples are 72. This CFD is then used to generate $F_X(x)$ for different mean corrosion rates between 0 and ≤4 mpy.

Figure 18:
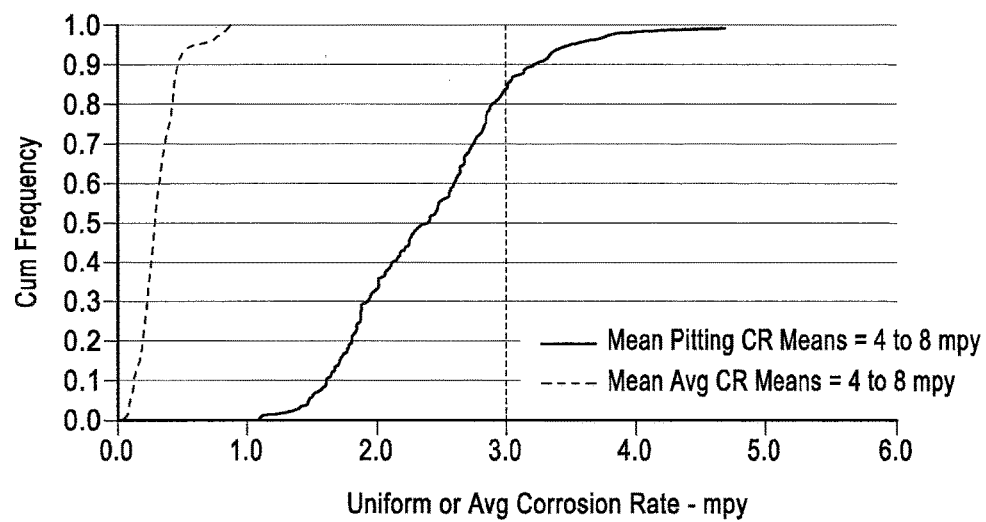

FIG. 18 illustrates a $F_X(x)$ generated by using the maximum pitting depth from all eight of the replicates at each site in FIG. 16 when sorted by the mean of the eight replicate samples with means between 4 and ≤8 mpy. The total number of replicate samples are 184. This CFD is then used to generate $F_X(x)$ for different mean corrosion rates between 4 and ≤8 mpy.

Figure 19:
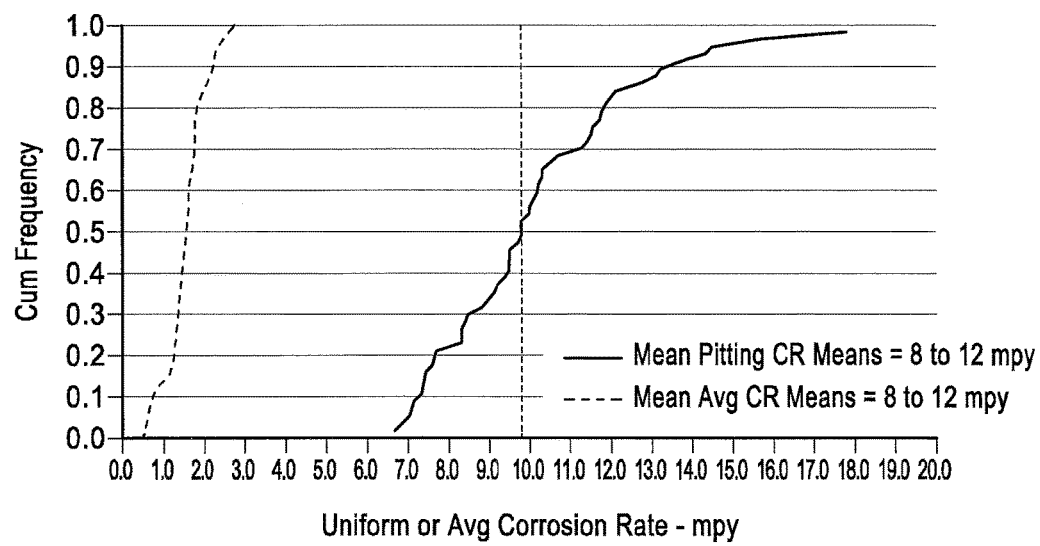

FIG. 19 illustrates $F_X(x)$ generated by using the maximum pitting depth from all eight of the replicates at each site in FIG. 16 when sorted by the mean of the eight replicate samples with means between 8 and ≤12 mpy. The total number of replicate samples are 56. This CFD is then used to generate $F_X(x)$ for different mean corrosion rates between 8 and ≤12 mpy.

Figure 20:
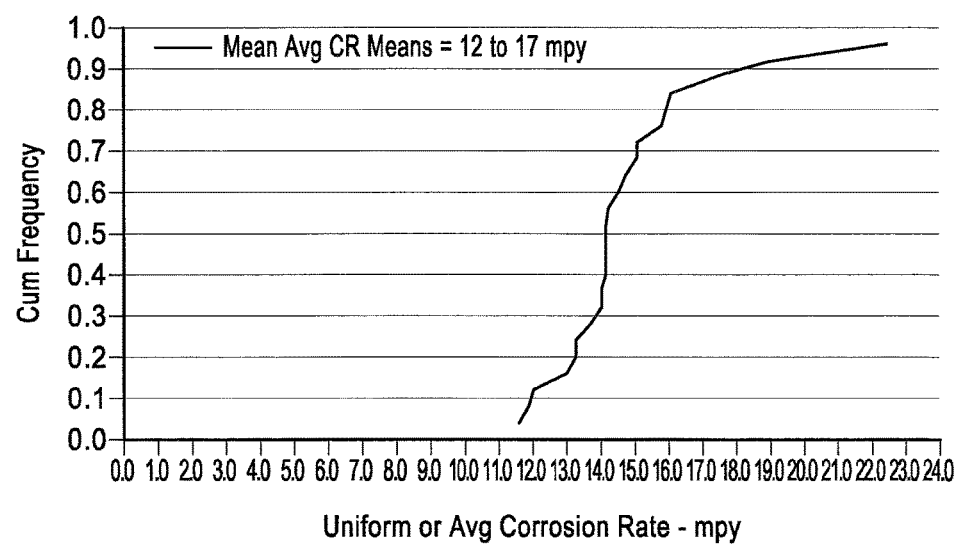

FIG. 20 illustrates $F_X(x)$ generated by using the maximum pitting depth from all eight of the replicates at each site in FIG. 16 when sorted by the mean of the eight replicate samples with means between 12 and ≤17 mpy. The total number of replicate samples are 24. This CFD is then used to generate $F_X(x)$ for different mean corrosion rates between 12 and ≤17 mpy.

Figure 21:
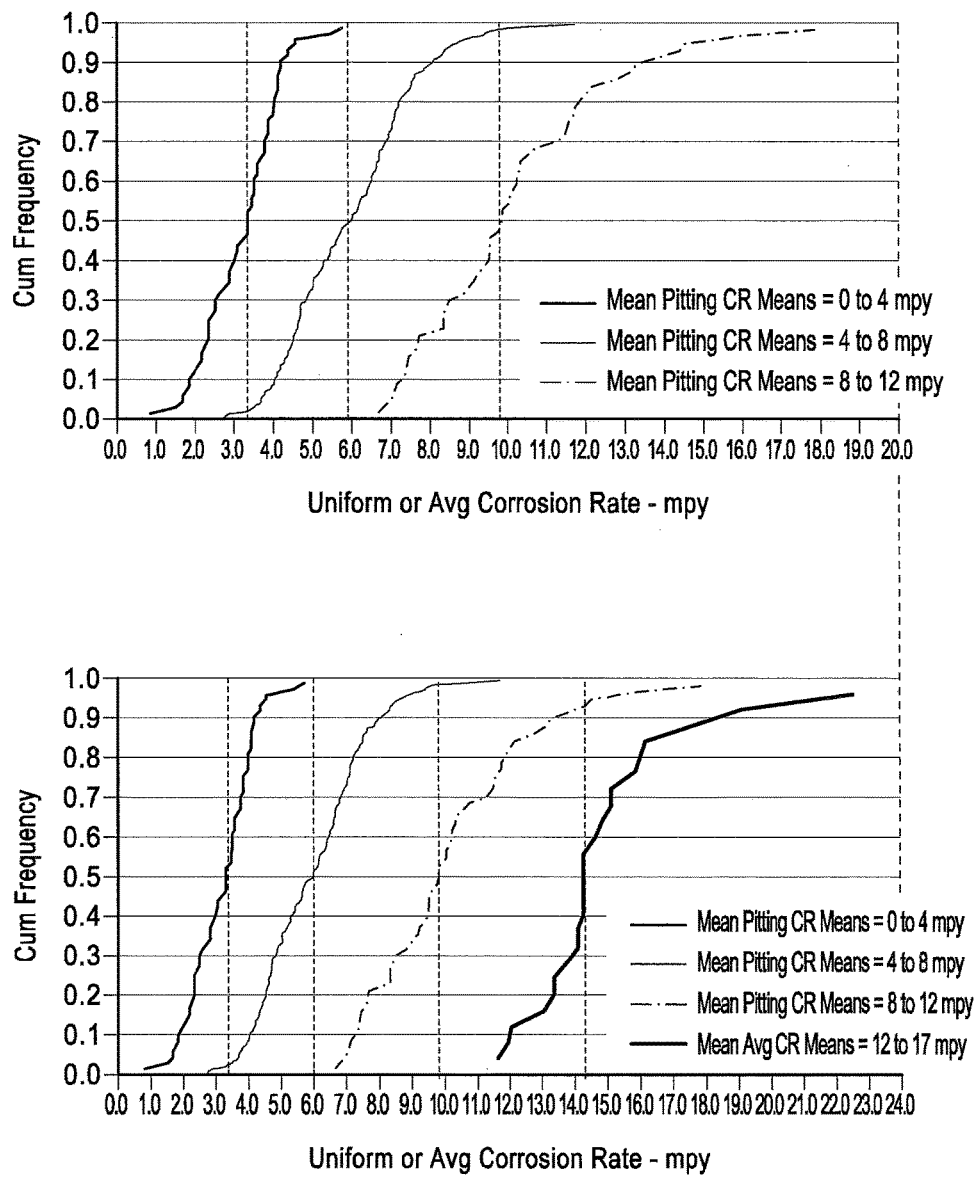

FIG. 21 illustrates (A) Three $F_X(x)$'s presented in FIGS. 17-19 for the corrosion rates due to pitting depth and (B) Four $F_X(x)$'s presented in FIGS. 17-20 for the corrosion rates due to pitting depth.

Figure 22:
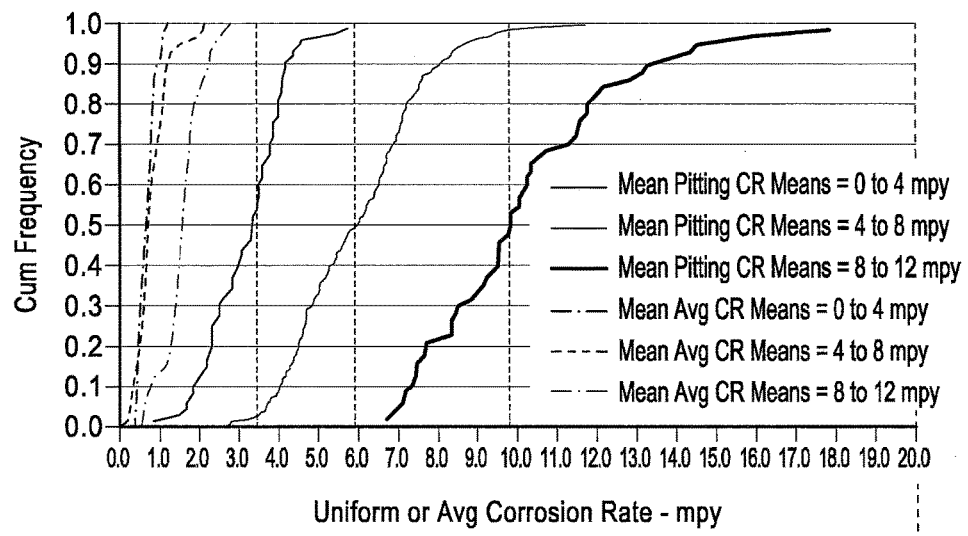
Figure 22:
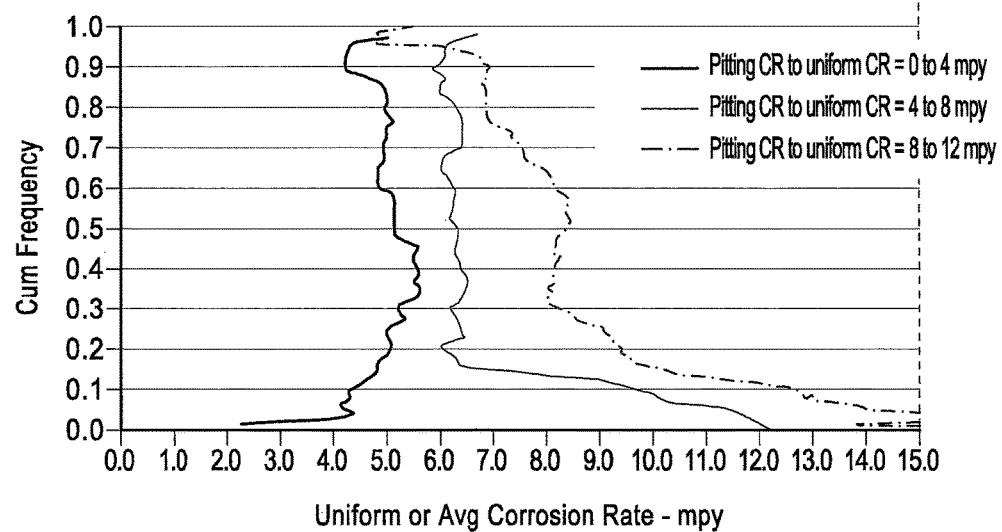

FIG. 22 illustrates (A) Three $F_X(x)$'s presented in FIGS. 17-19 for the corrosion rates due to pitting depth and uniform corrosion rate ($<CR_{pitting}>$, $<CR_{uniform}>$, raw $CR_{pitting}$, raw $CR_{uniform}$) and (B) The ratio of the raw pitting to uniform corrosion rate ($Ratio_{pit\ to\ uniform}$=raw $CR_{pitting}$/$CR_{uniform}$).

Figure 4:
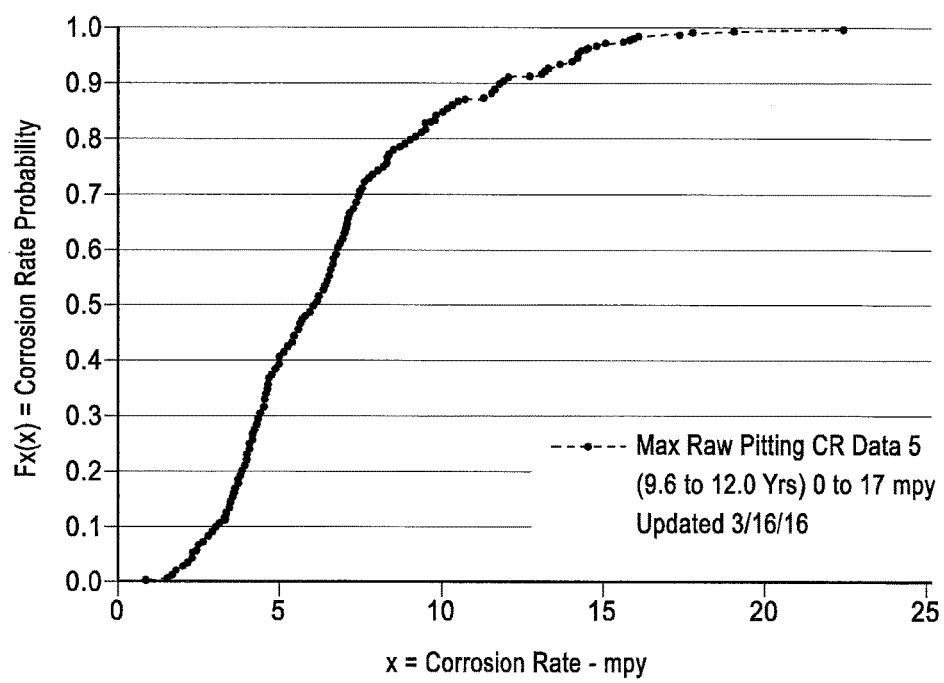
Figure 5:
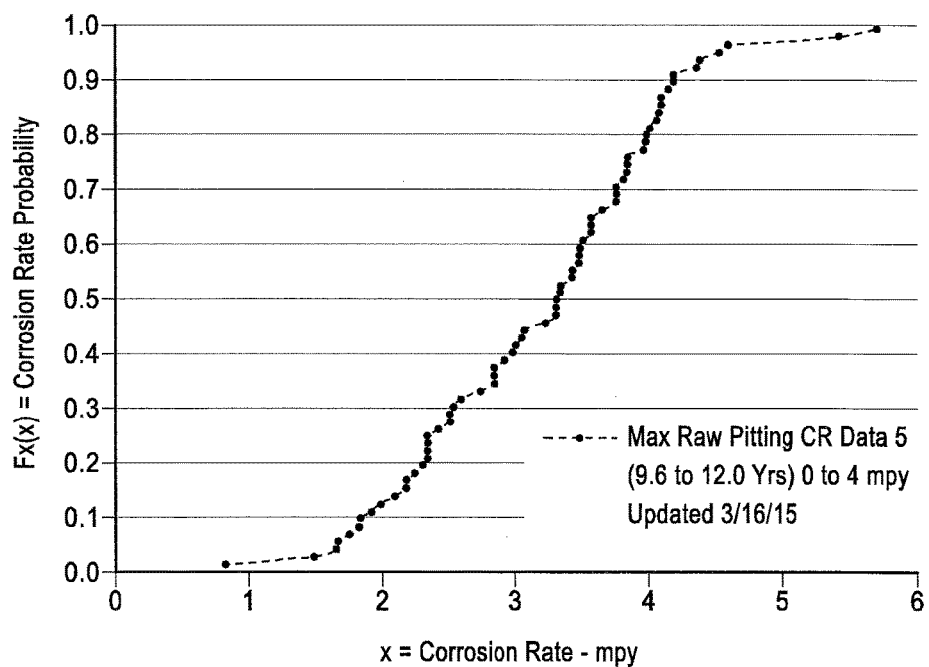
Figure 6:
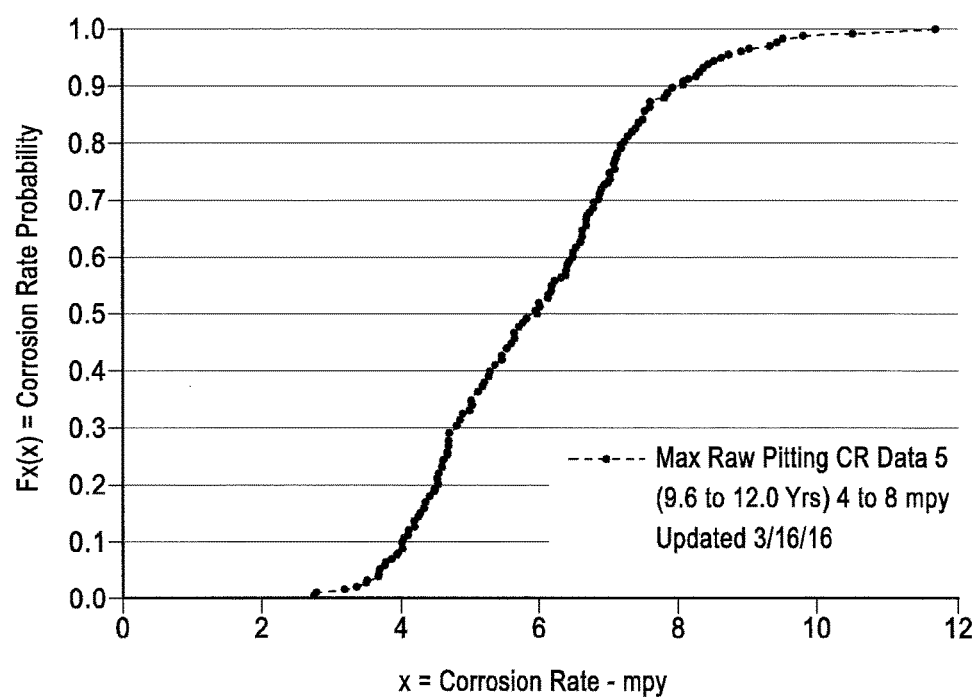
Figure 7:
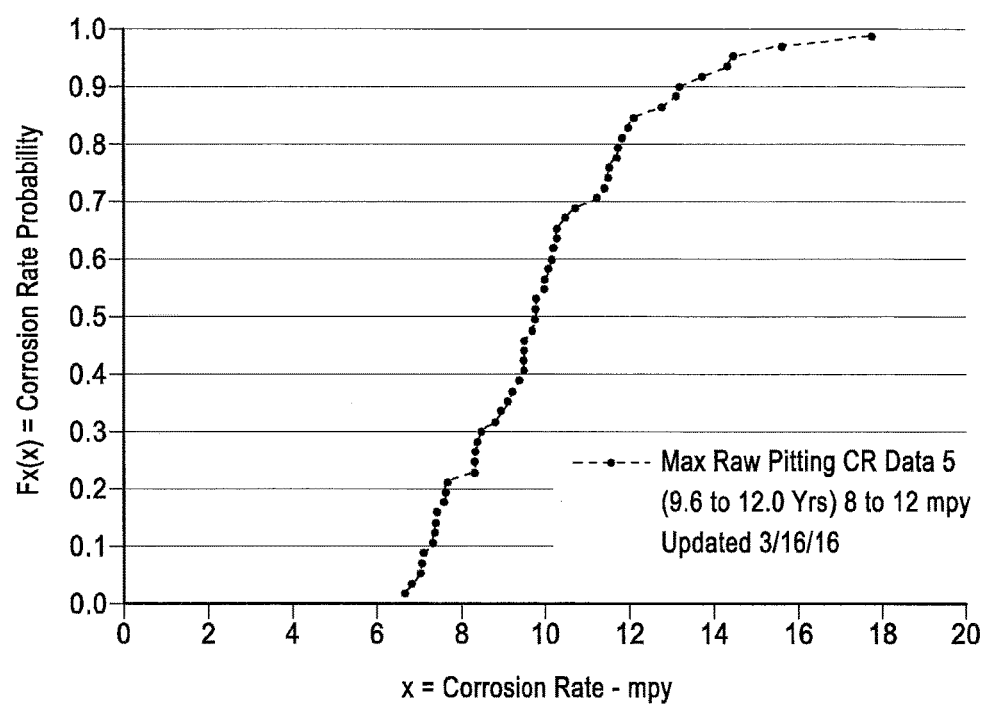
Figure 8:
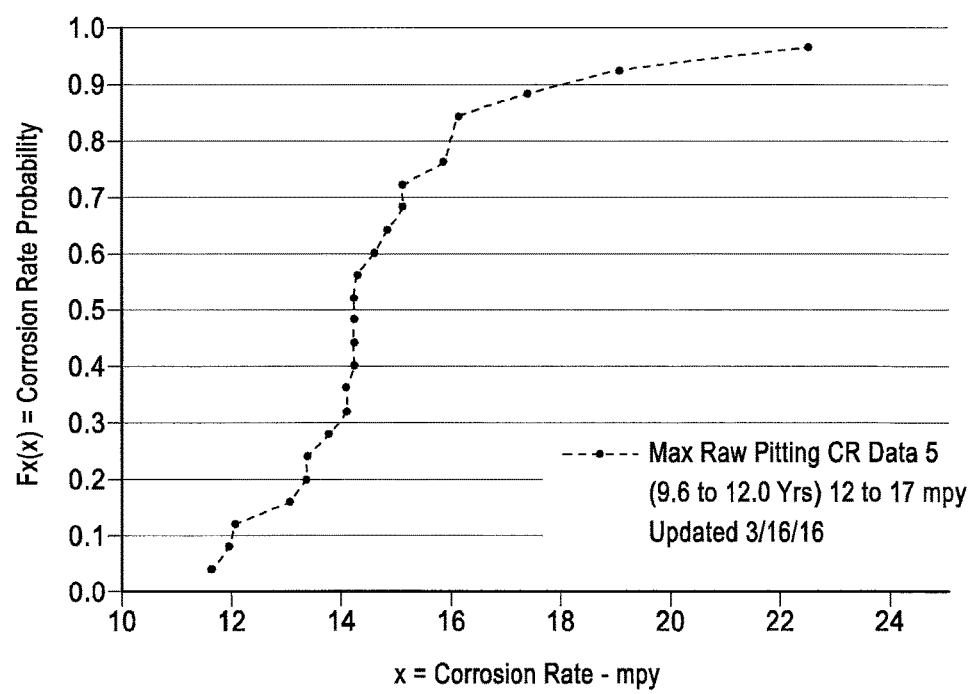
Figure 9:
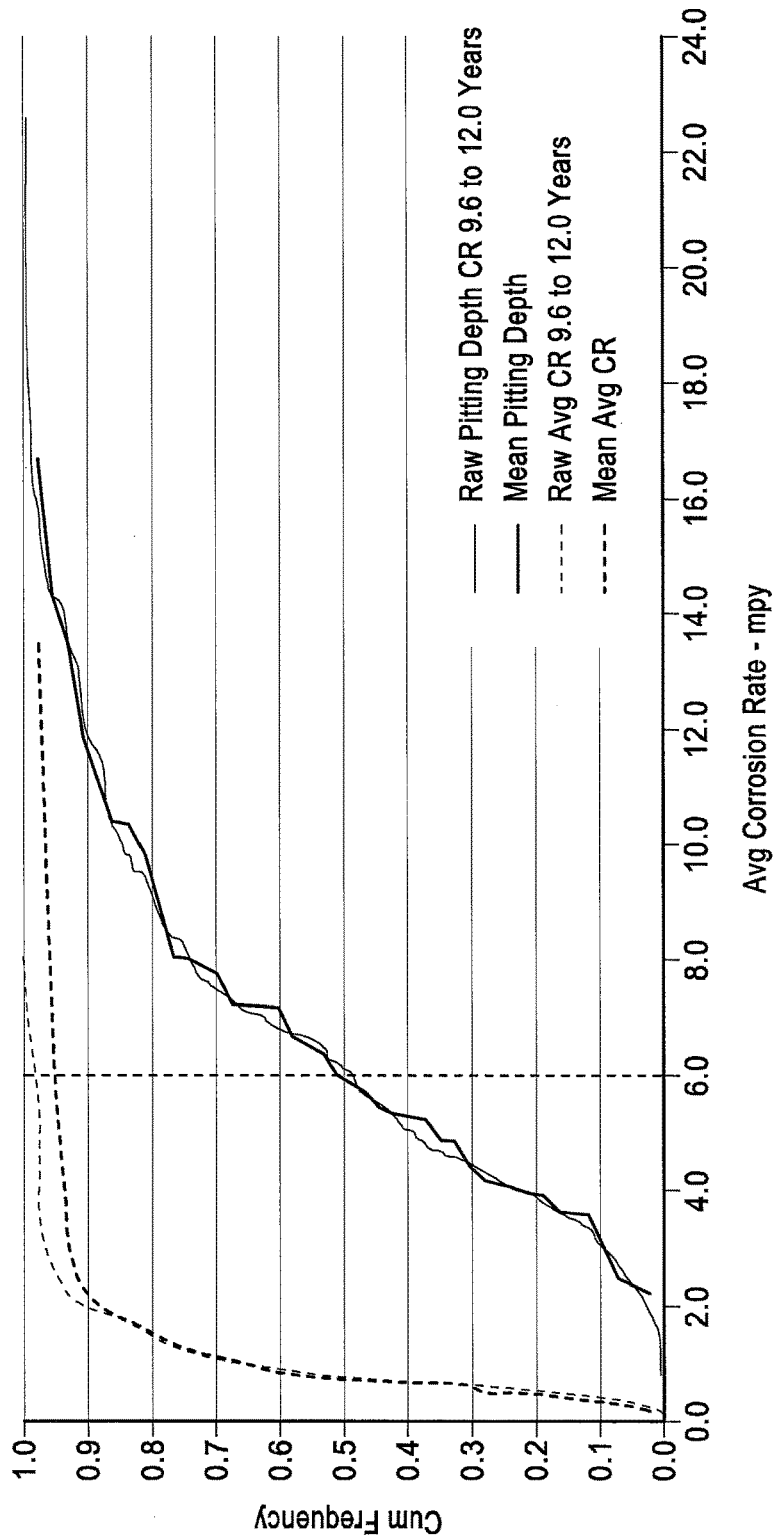
Figure 10:
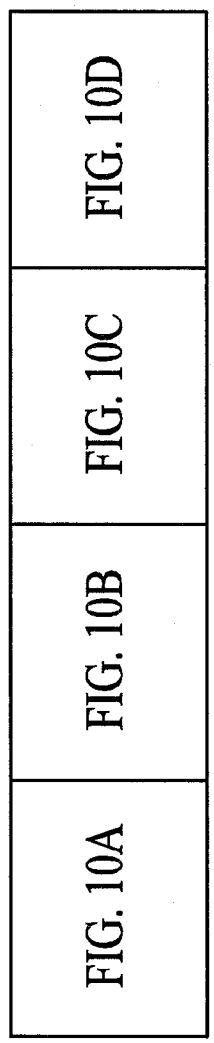
FIG. 10 illustrates a summary overview flow chart of the six major activities to implement this method.
Figure 10A:
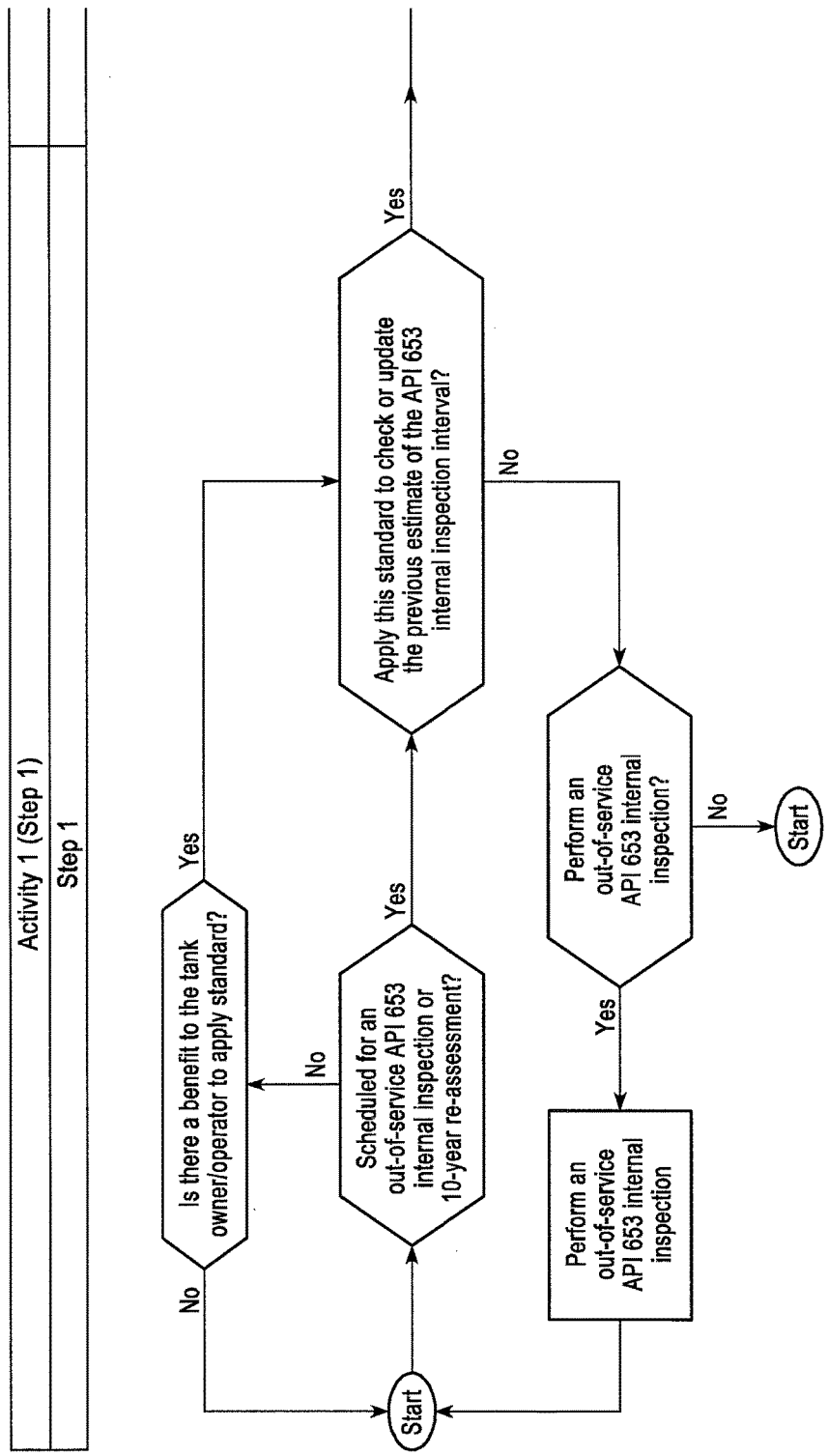
Figure 10B:
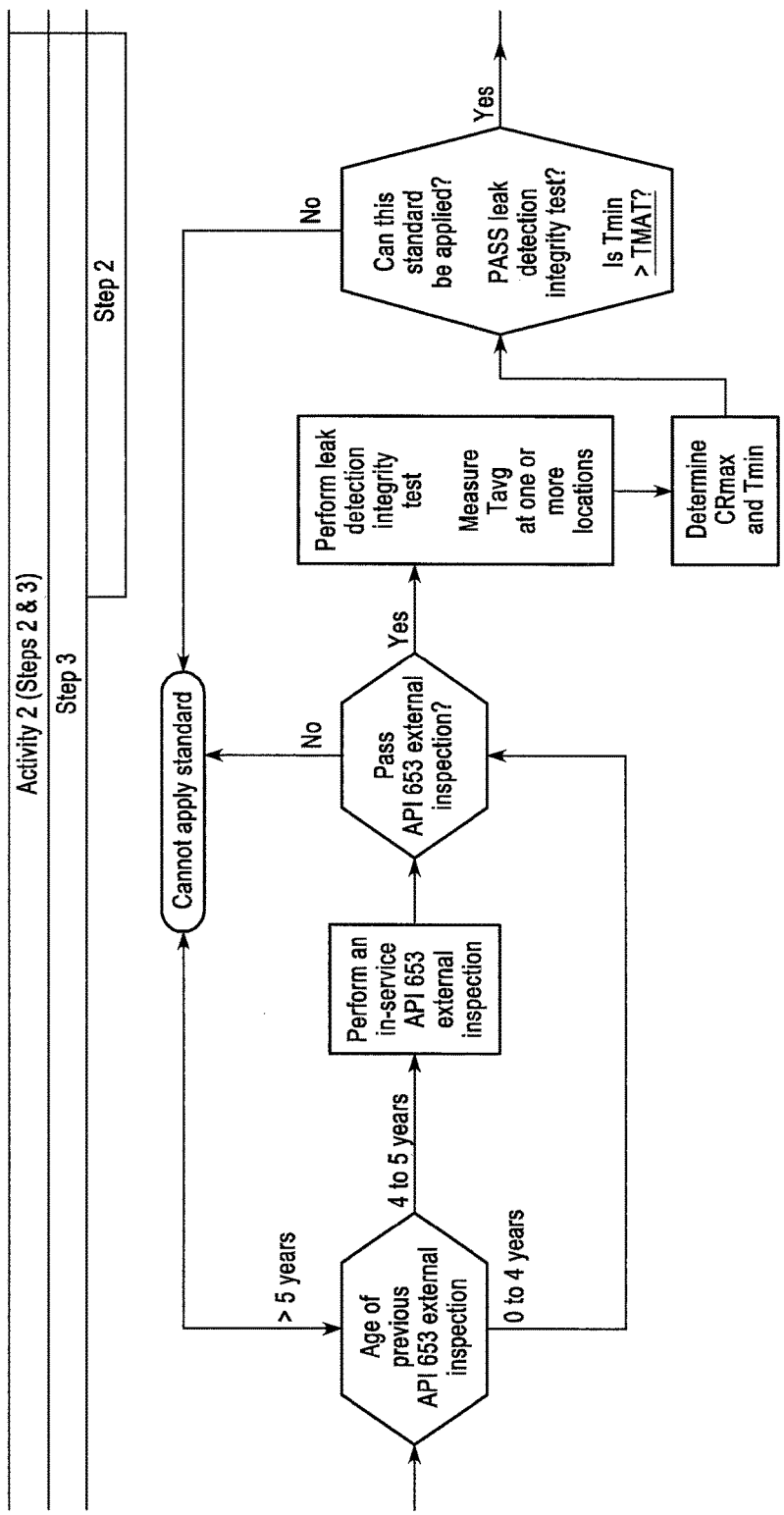
Figure 10C:
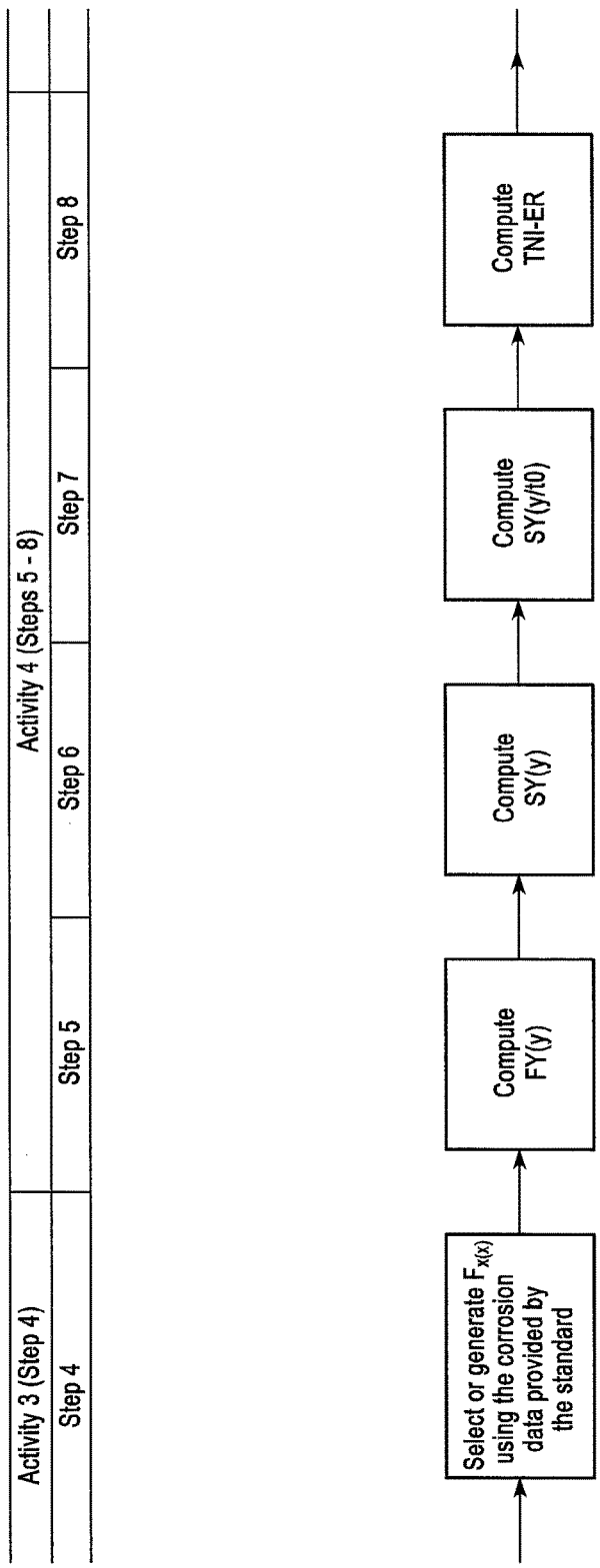
Figure 10D:
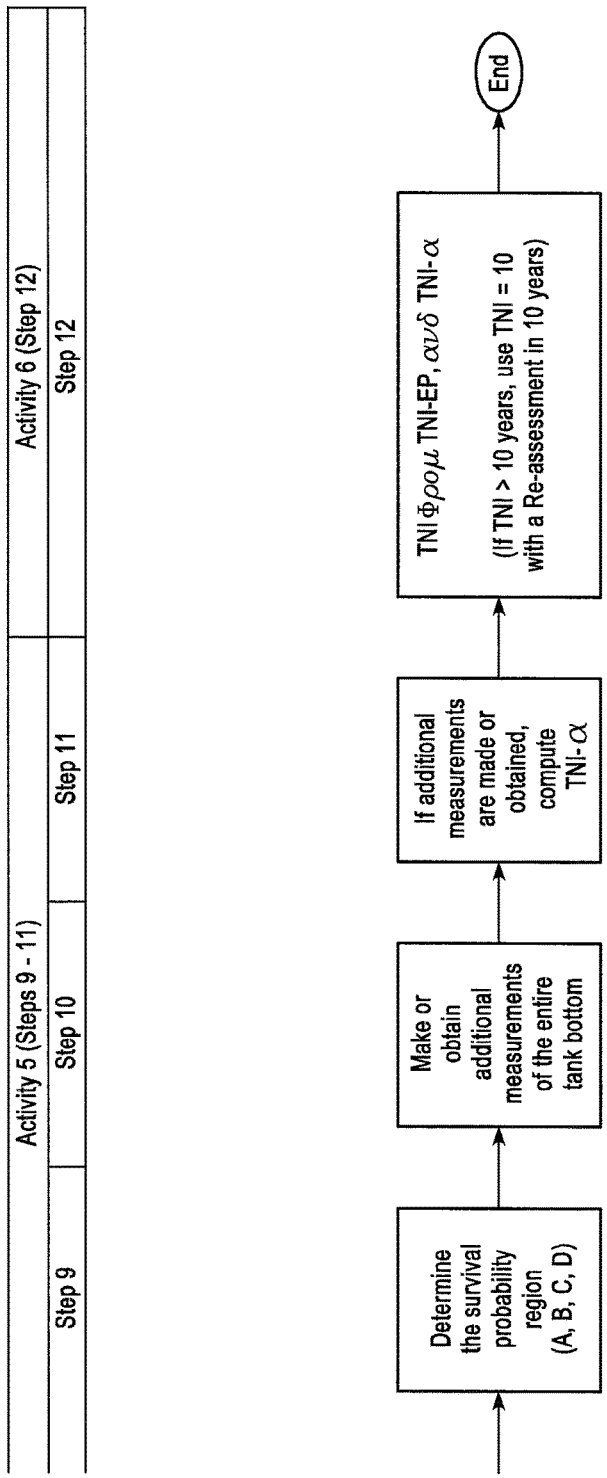
Figure 11A:
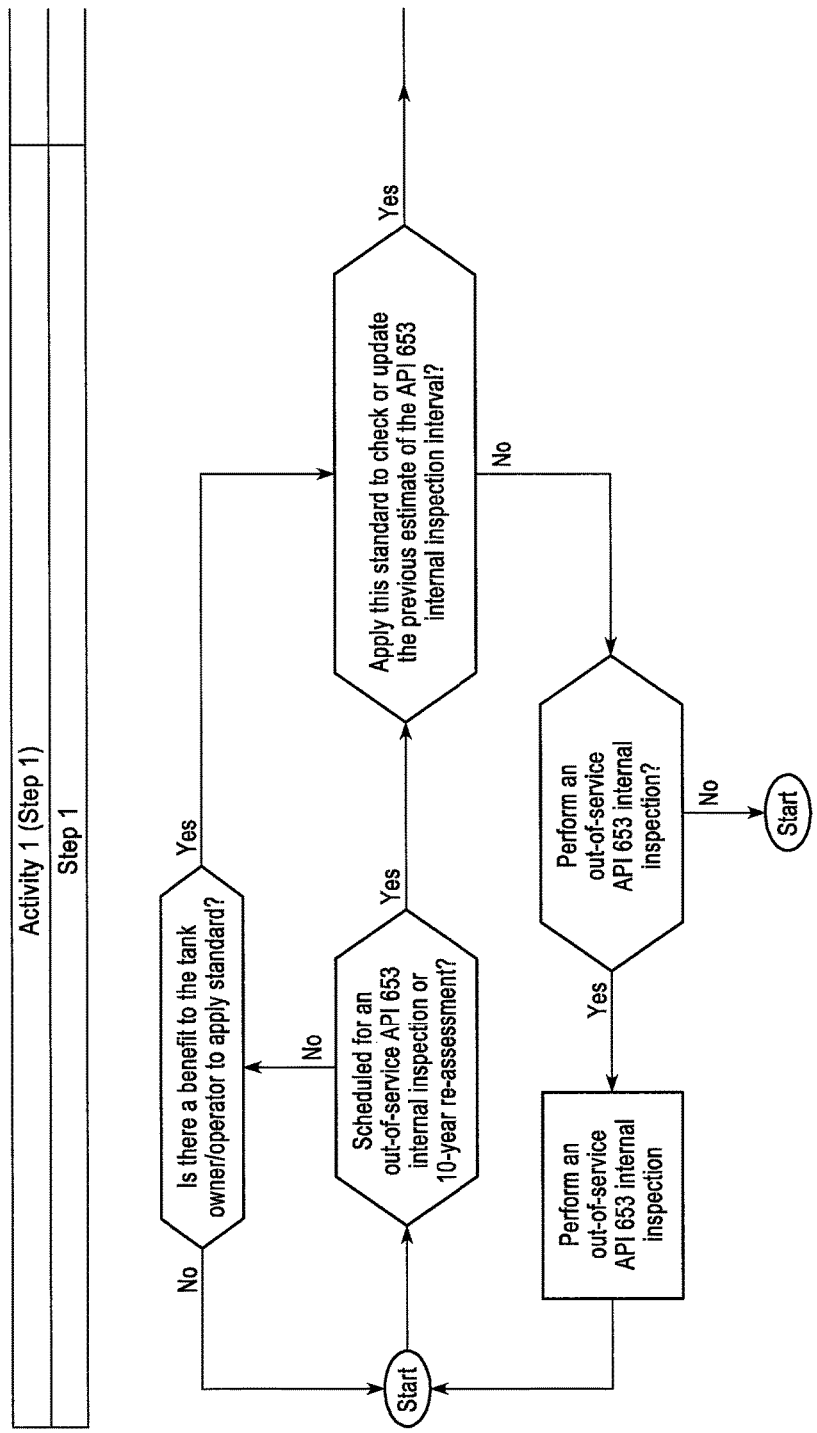
FIG. 11 illustrates a detailed overview flow chart of the six major activities to implement this method.
Figure 11B:
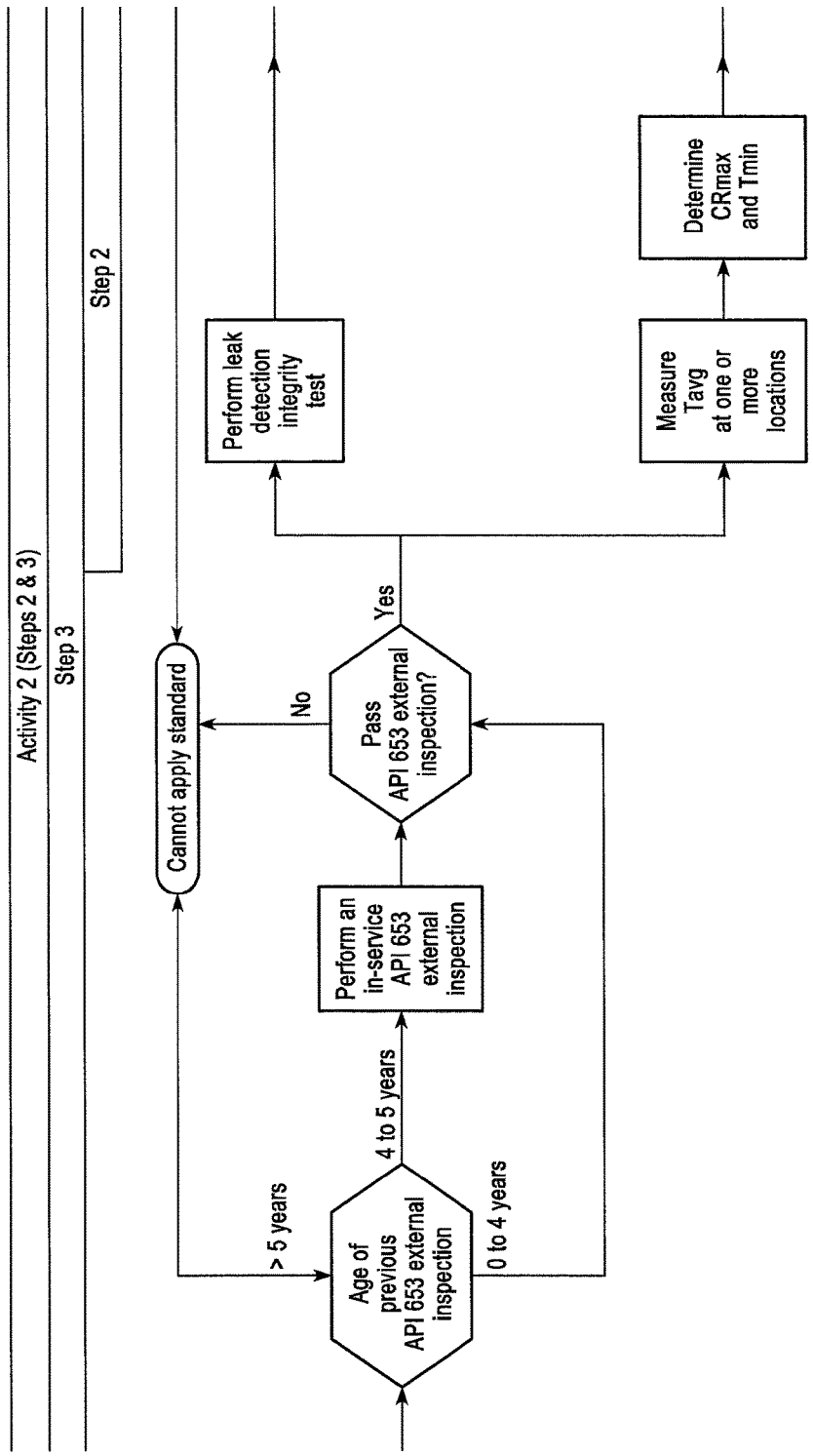
Figure 11C:
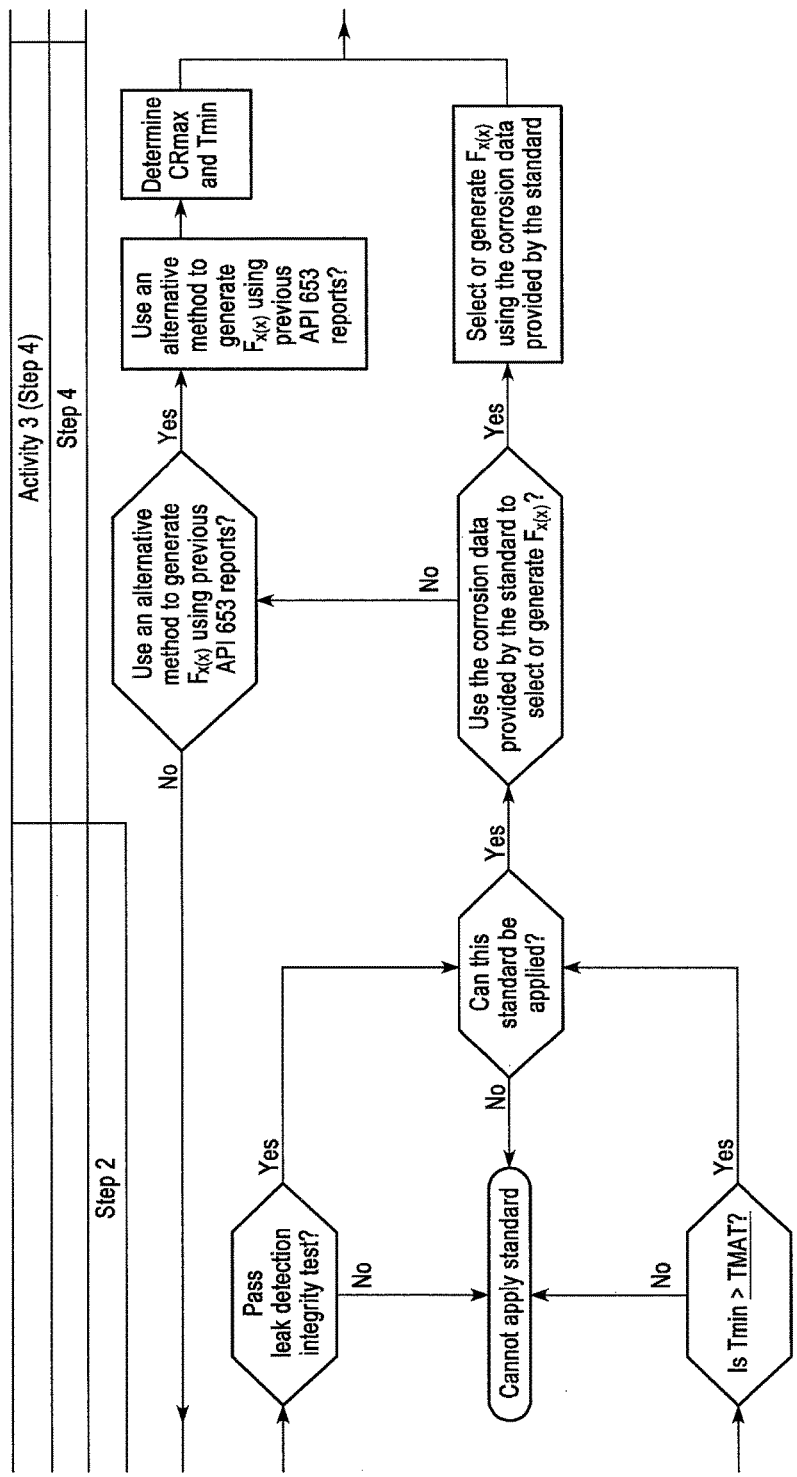
Figure 11D:
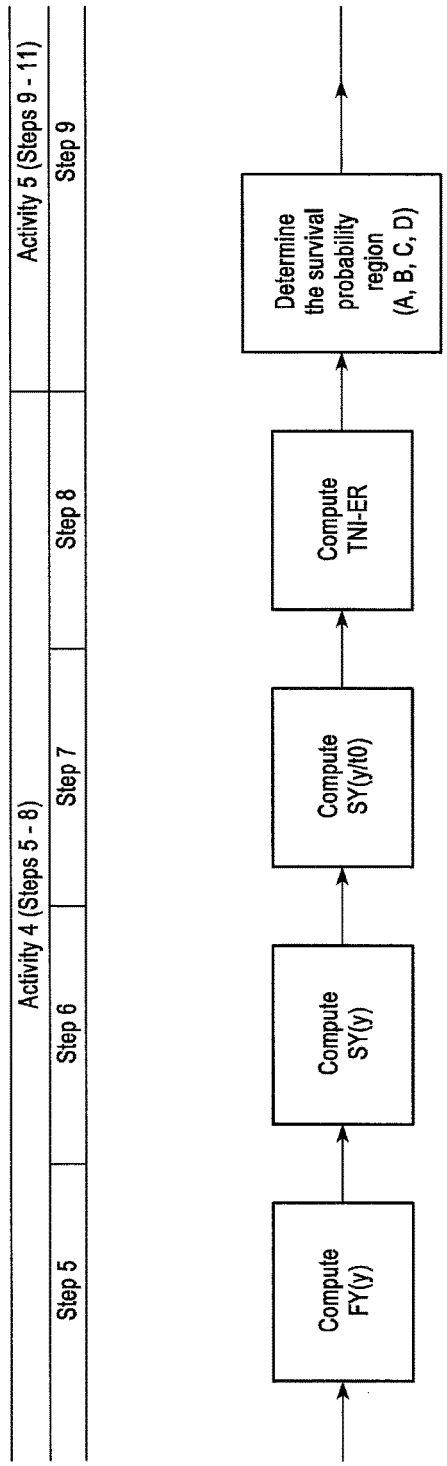
Figure 11E:
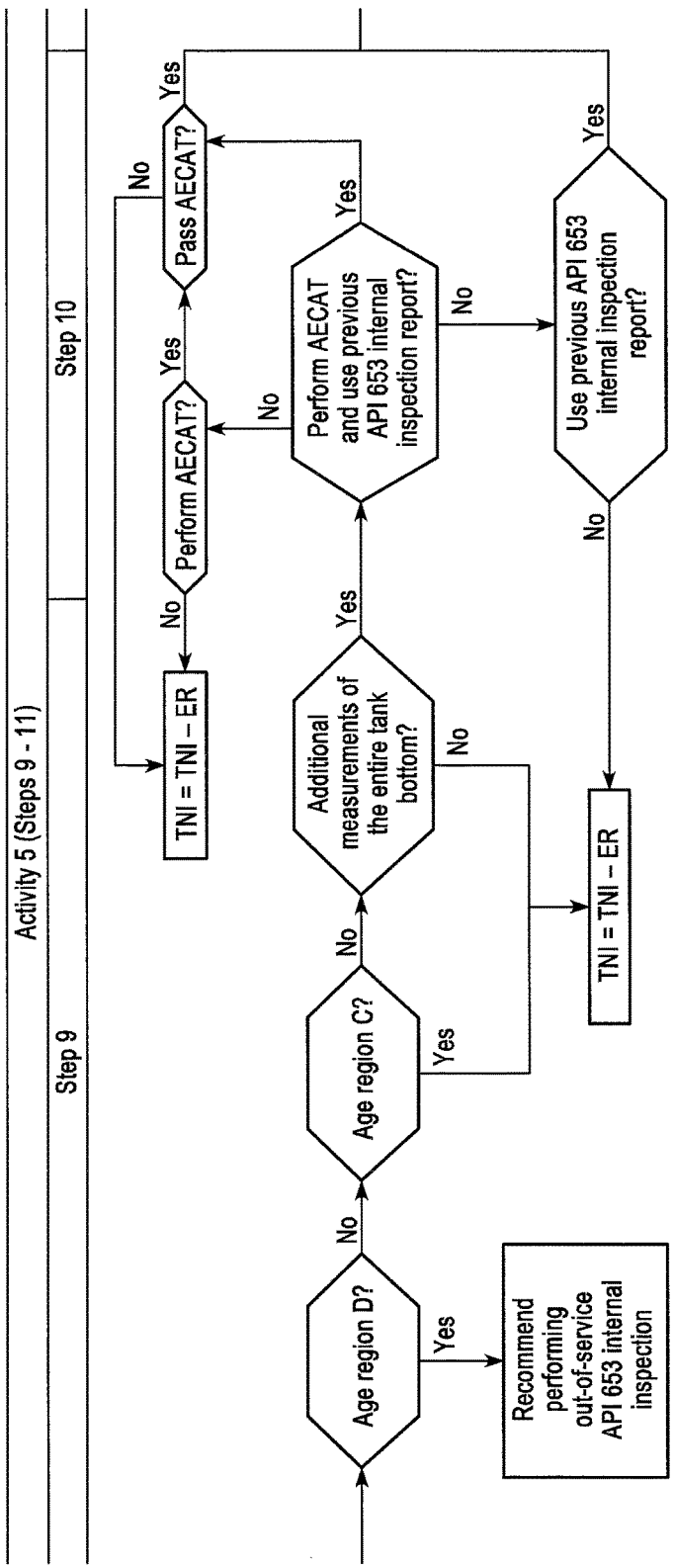
Figure 11F:
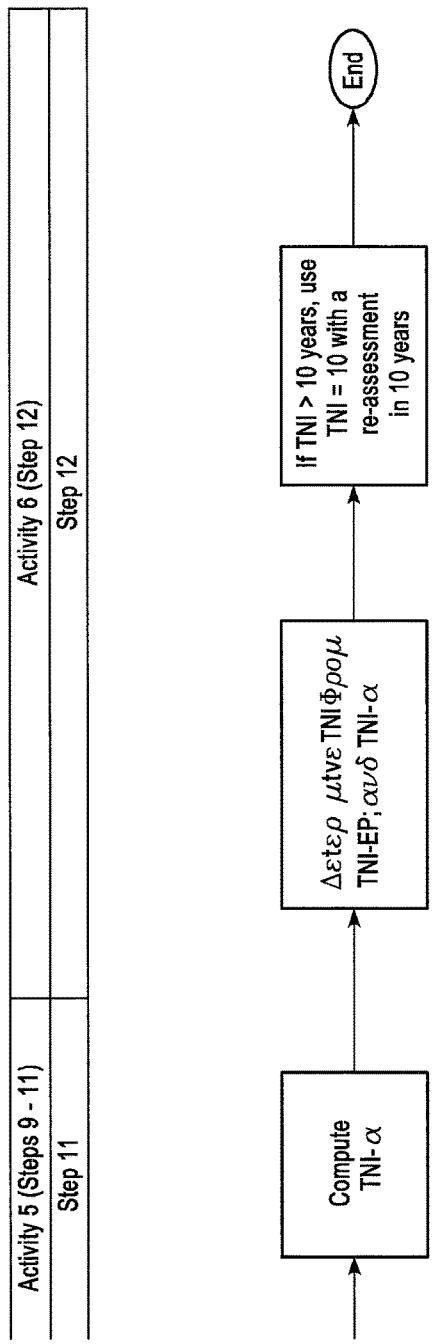
Figure 12:
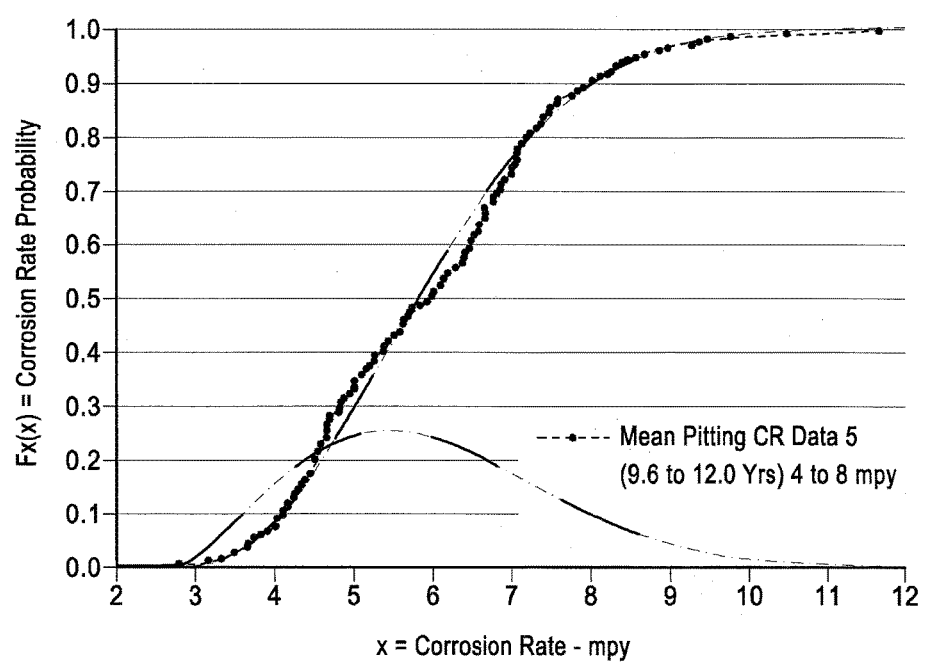
FIG. 12 illustrates $F_X(x)$ and $f_X(x)$ for a $CR_{max}$ of 6 mpy using corrosion data with values between 4 and 8 mpy. The dashed line represents the Weibull CDF fit to the empirical CFD.
Figure 13:
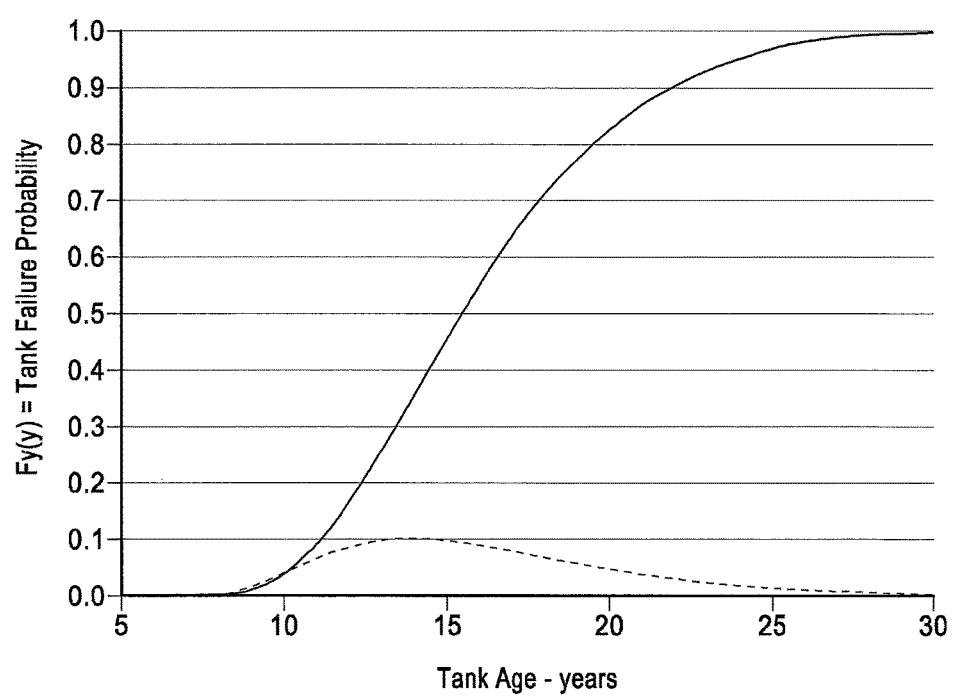
FIG. 13 illustrates $F_Y(y)$ and $f_Y(y)$ for $F_X(x)$ in FIG. 12 using the Weibull CDF.
Figure 14:
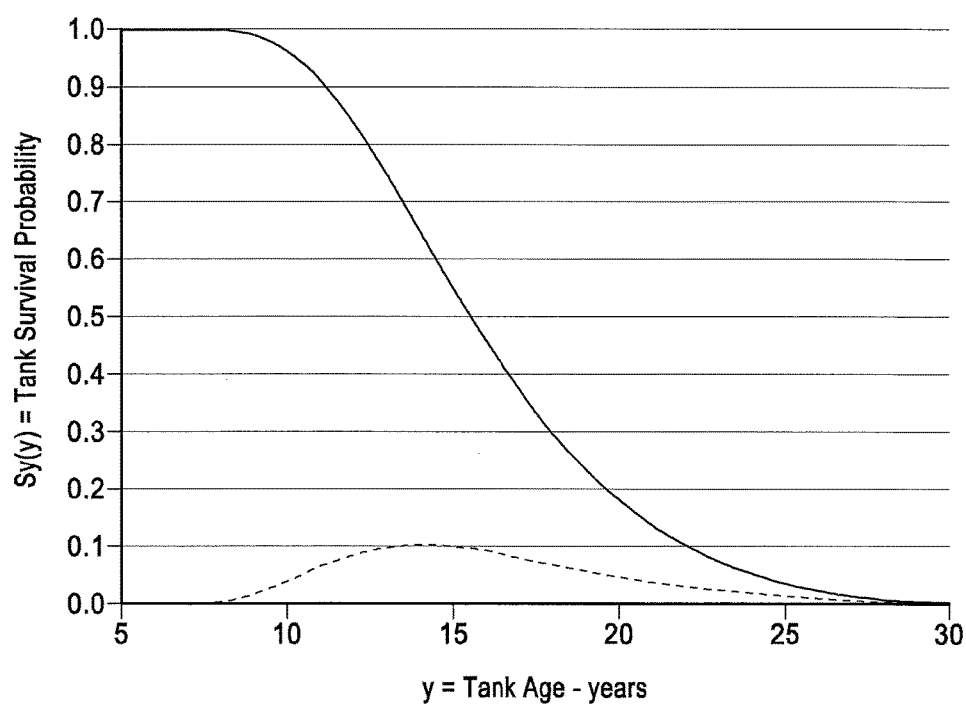
FIG. 14 illustrates $S_Y(y)$ and $s_Y(y)$ for $F_Y(y)$ and $f_Y(y)$ in FIG. 13.
Figure 15:
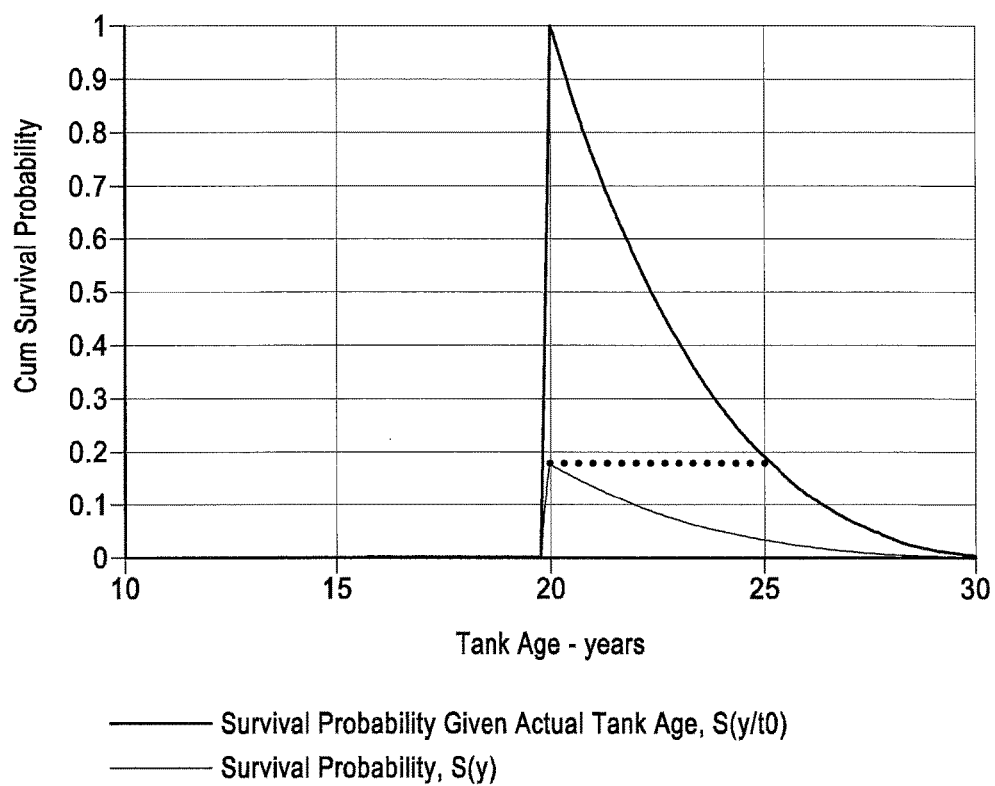
FIG. 15 illustrates $S_Y(y)$ and $S_Y(y/t_0)$ superimposed on $S_Y(y)$ between $y=t_0$ and $y=t_N$, where $S_Y(y=t_N/t_0)=S_Y(y=t_0)$, for $F_X(x)$ in Appendix X3 to illustrate the determination of TNI-ER using Equivalent Risk.
Figure 23:
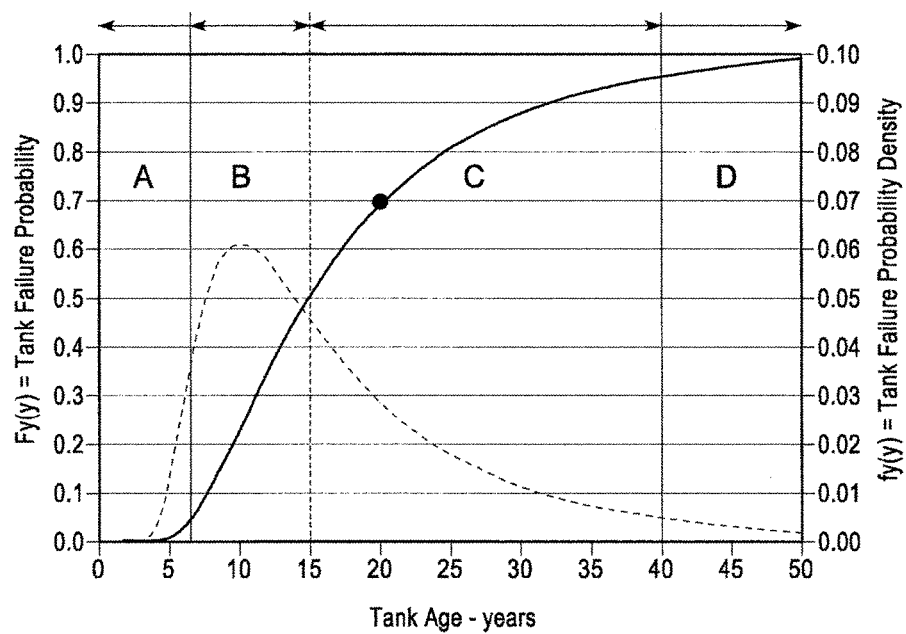

FIG. 23 illustrates the Survival Age Regions for $F_Y(y)$ and $f_Y(y)$ generated for $F_X(x)$ in FIG. 4 using the Weibull CDF for $F_X(x)$.

Figure 24:
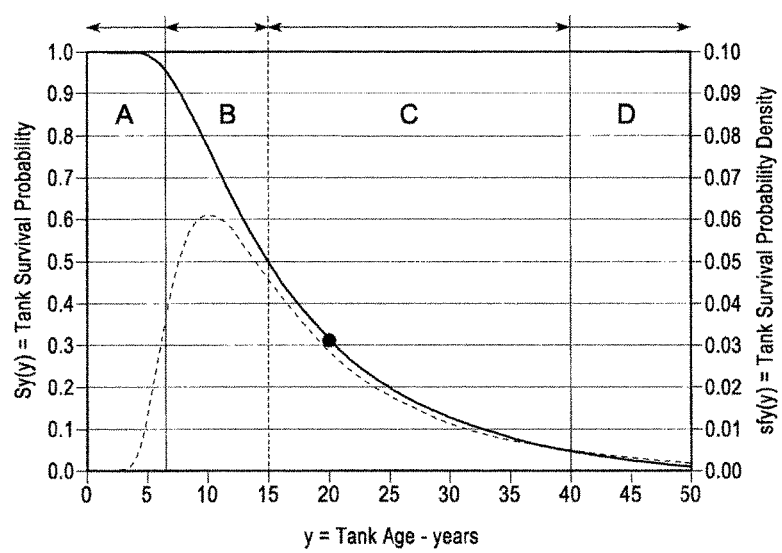

FIG. 24 illustrates the Survival Age Regions for $S_Y(y)$ and $s_Y(y)$ generated for $F_Y(y)$ and $f_Y(y)$ in FIG. 23.

Figure 25:
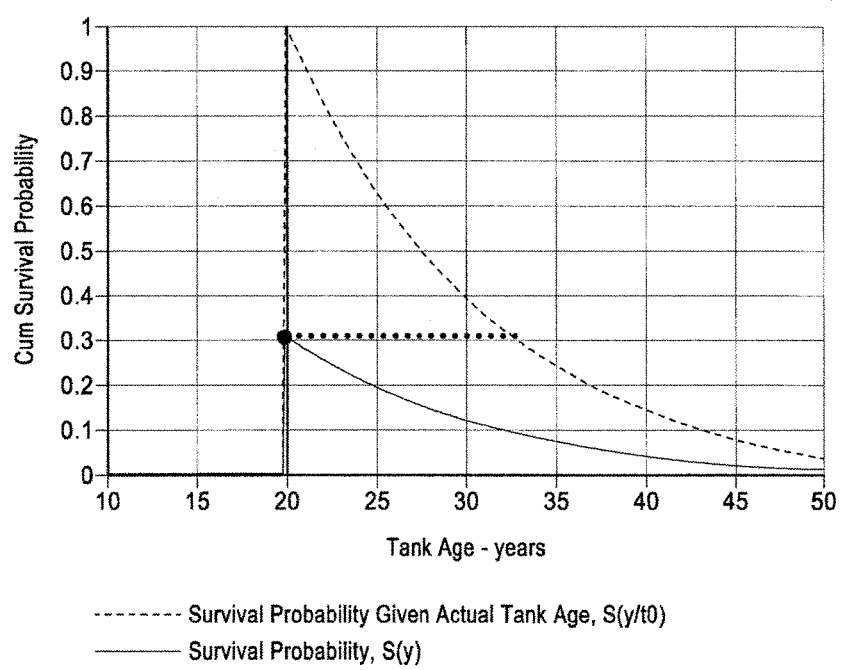

FIG. 25 illustrates the determination of TNI-ER for Survival Age Region C for $S_Y(y)$ generated in FIG. 24 20 years after the previous out-of-service API 653 internal inspection.

Figure 26:
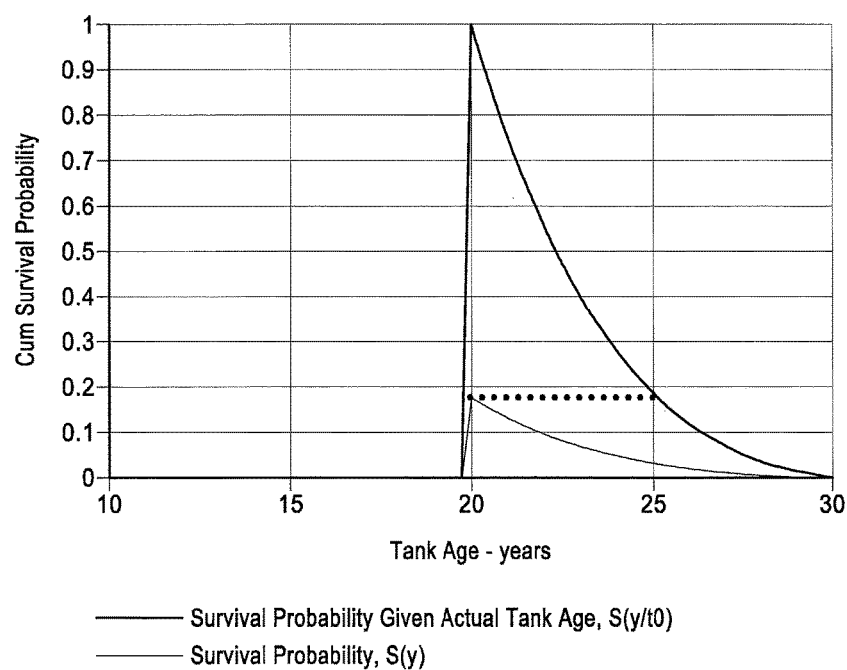

FIG. 26 illustrates $S_Y(y)$ and $S_Y(y/t_0)$ superimposed on $S_Y(y)$ between $y=t_0$ and $y=t_N$, where $S_Y(y=t_N/t_0)=S_Y(y=t_0)$, for $F_X(x)$ in Appendix X3 to illustrate the determination of TNI-ER in Region C for $y=t_0=20$ years using Equivalent Risk. TNI-ER=5.35 years, as illustrated by the blue dotted line.

Figure 27:
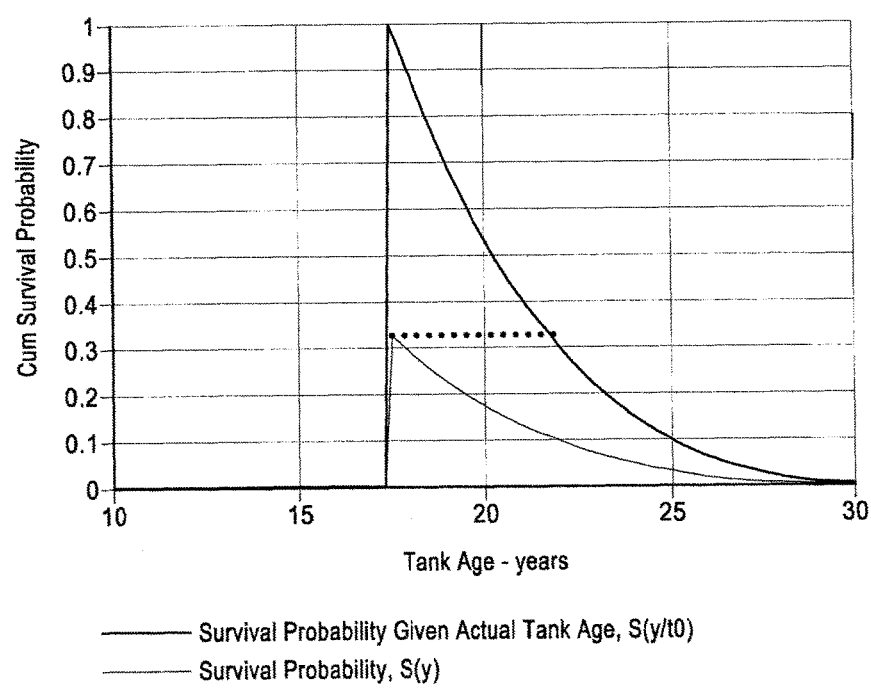

FIG. 27 illustrates $S_Y(y)$ and $S_Y(y/t_0)$ superimposed on $S_Y(y)$ between $y=t_0$ and $y\ t_N$, where $S_Y(y=t_N/t_0)=S_Y(y=t_0)$, for $F_X(x)$ in Appendix X3 to illustrate the determination of TNI-ER in Region C for $y=t_0=17.5$ years using Equivalent Risk. TNI-ER=4.45 years, as illustrated by the blue dotted line.

Figure 28:
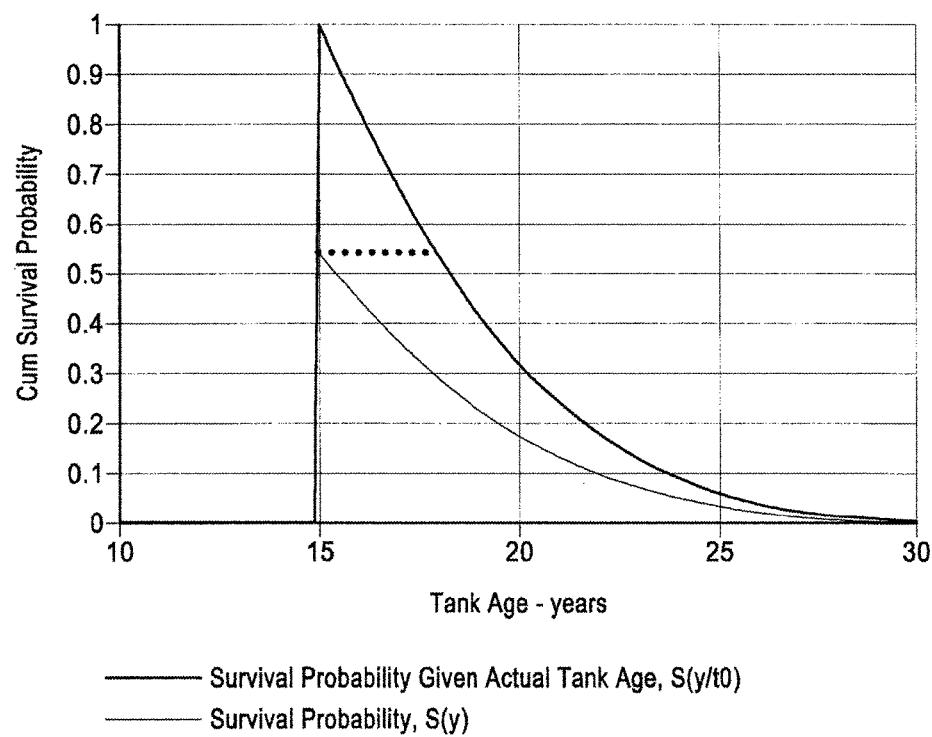

FIG. 28 illustrates $S_Y(y)$ and $S_Y(y/t_0)$ superimposed on $S_Y(y)$ between $y=t_0$ and $y=t_N$, where $S_Y(y=t_N/t_0)=S_Y(y=t_0)$, for $F_X(x)$ in Appendix X3 to illustrate the determination of TNI-ER in Region C for $y=t_0=15.0$ years using Equivalent Risk. TNI-ER=3.0 years, as illustrated by the blue dotted line.

Figure 29:
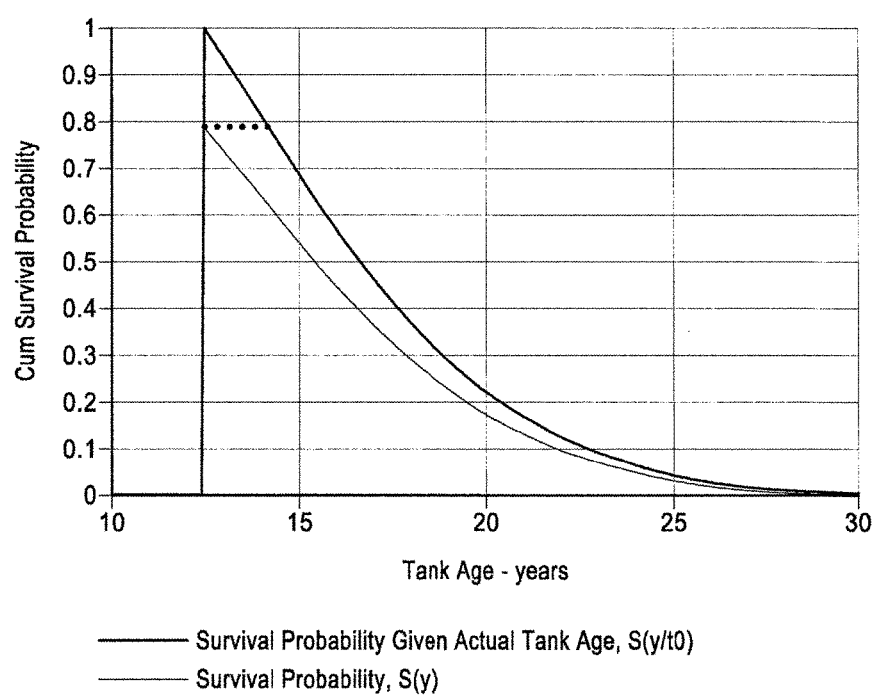

FIG. 29 illustrates $S_Y(y)$ and $S_Y(y/t_0)$ superimposed on $S_Y(y)$ between $y=t_0$ and $y=t_N$, where $S_Y(y=t_N/t_0)=s_Y(y=t_0)$, for $F_X(x)$ in Appendix X3 to illustrate the determination of TNI-ER in Region B for $y=t_0=12.5$ years using Equivalent Risk. TNI-ER=1.9 years, as illustrated by the blue dotted line.

Figure 30:
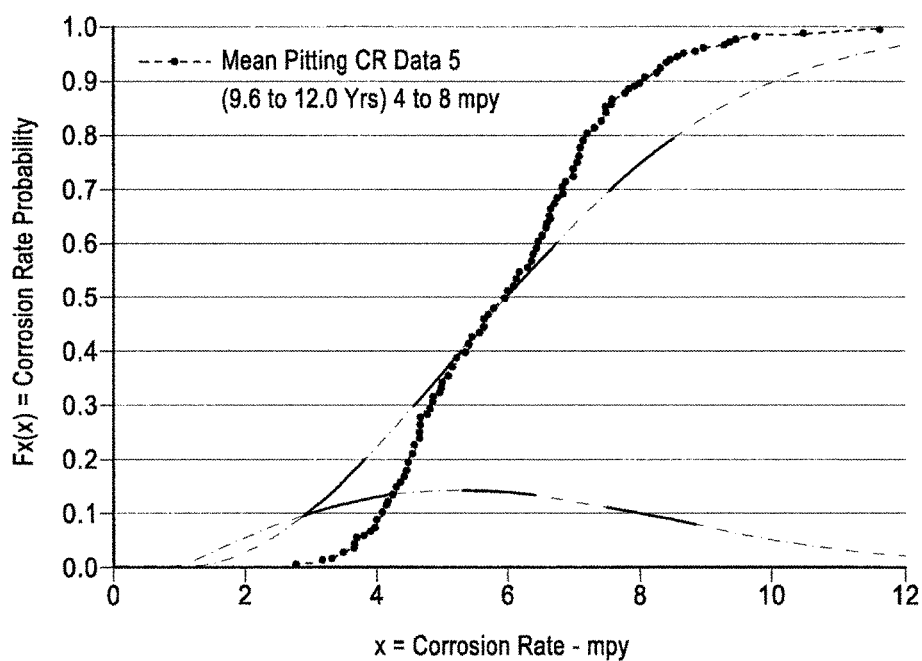

FIG. 30 illustrates a preliminary fit selected for $F_X(x)$ for assumed values of $\gamma=1.0$, $\beta=2.0$, and $\eta=6.0$, where the mean square errors are MSE-x=0.775 and MSE-$F_X(x)$=0.085.

Figure 31:
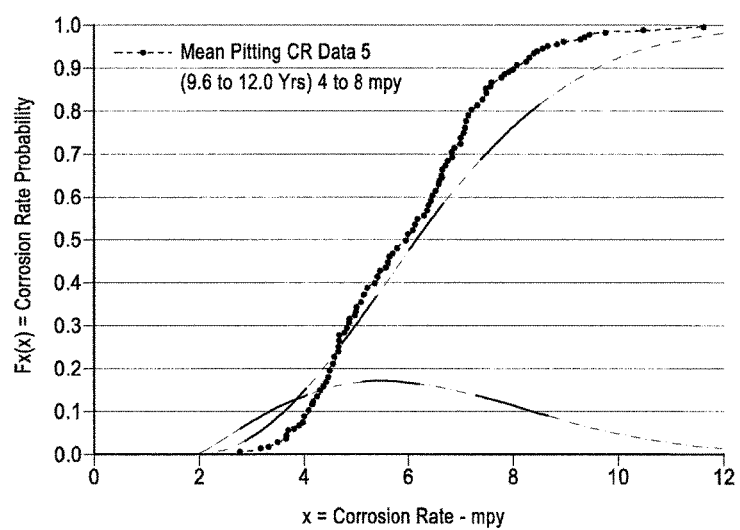

FIG. 31 illustrates a preliminary fit selected for $F_X(x)$ for assumed values of $\gamma=2.0$, $\beta=2.0$, and $\eta=5.0$, where the mean square errors are MSE-x=0.339 and MSE-$F_X(x)$=0.042.

Figure 32:
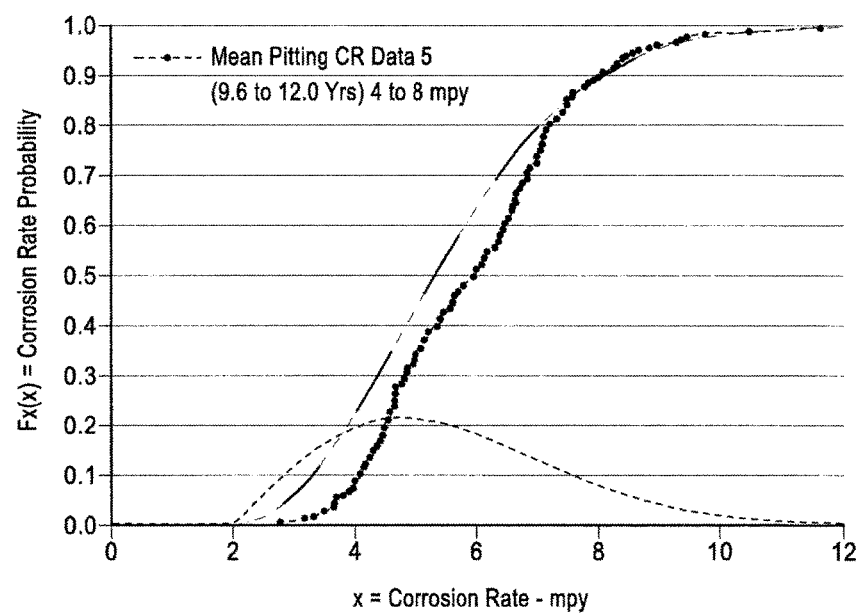

FIG. 32 illustrates a preliminary fit selected for $F_X(x)$ for assumed values of $\gamma=2.0$, $\beta=2.0$, and $\eta=4.0$, where the mean square errors are MSE-x=0.629 and MSE-$F_X(x)$=0.116.

Figure 33:
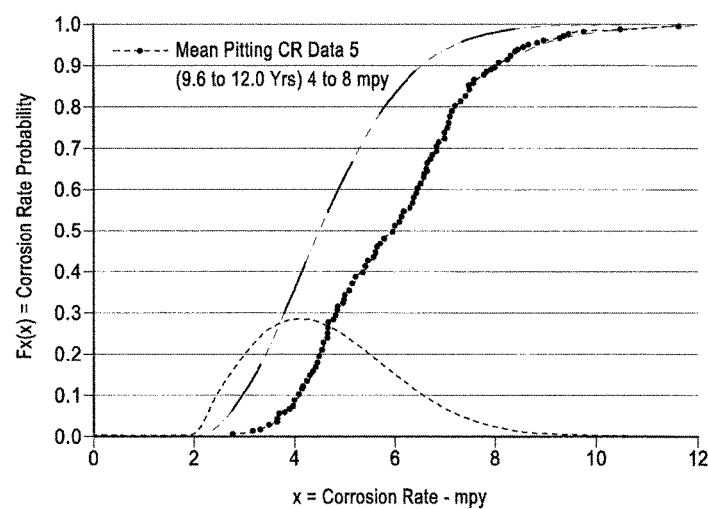

FIG. 33 illustrates a preliminary fit selected for $F_X(x)$ for assumed values of $\gamma=2.0$, $\beta=2.0$, and $\eta=3.0$, where the mean square errors are MSE-x=0.292 and MSE-$F_X(x)$=1.135.

Figure 34:
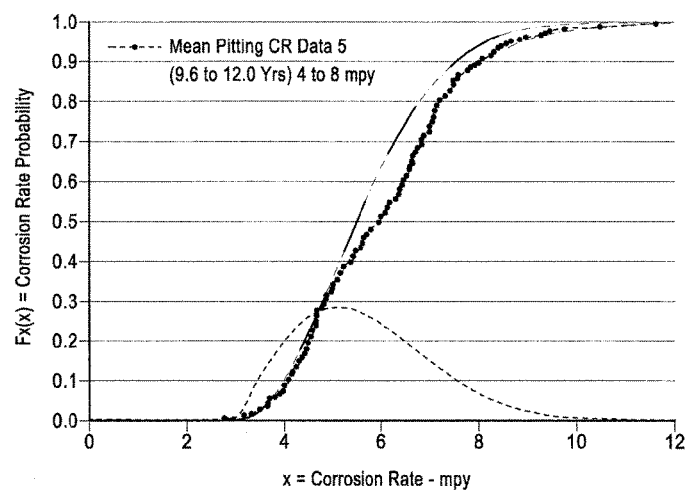

FIG. 34 illustrates a preliminary fit selected for $F_X(x)$ for assumed values of $\gamma=3.0$, $\beta=2.0$, and $\eta=3.0$, where the mean square errors are MSE-x=0.178 and MSE-$F_X(x)$=0.046.

Figure 35:
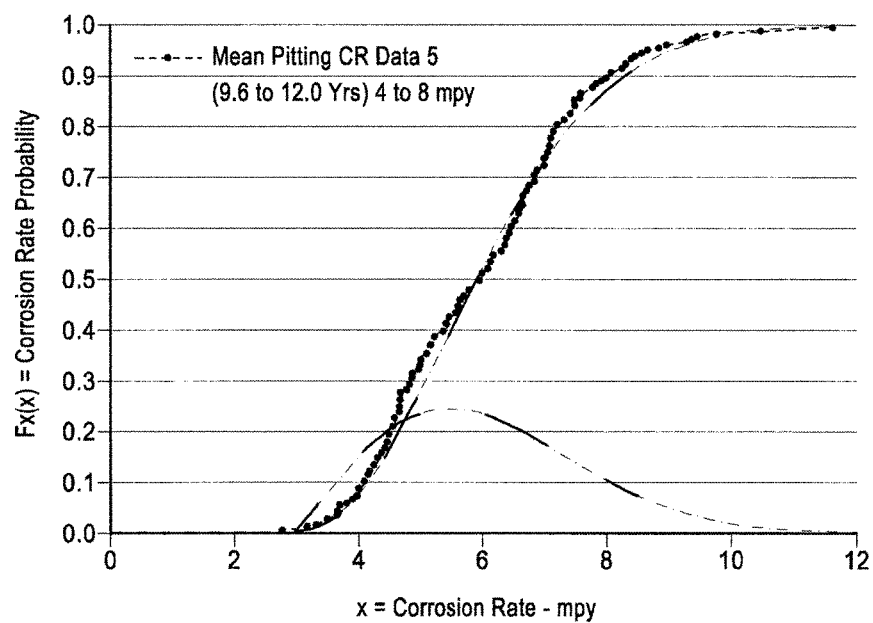

FIG. 35 illustrates a preliminary fit selected for $F_X(x)$ for assumed values of $\gamma=2.0$, $\beta=2.0$, and $\eta=3.5$, where the mean square errors are MSE-x=0.161 and MSE-$F_X(x)$=0.035.

Figure 36:
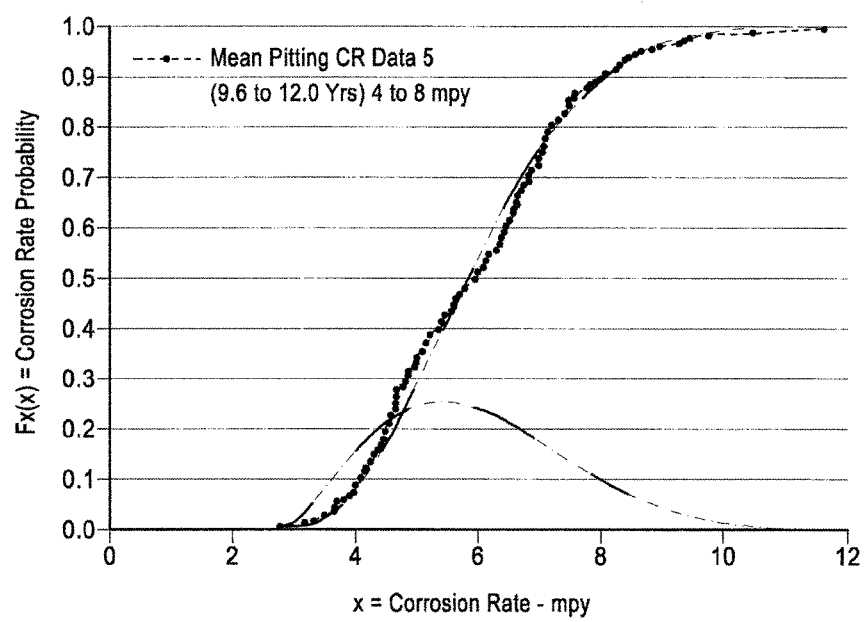

FIG. 36 illustrates the final selected fit for $F_X(x)$ for assumed values of $\gamma=2.9$, $\beta=2.1$, and $\eta=3.49$, where the mean square errors are MSE-x=0.121 and MSE-$F_X(x)$=0.027.

Figure 37:
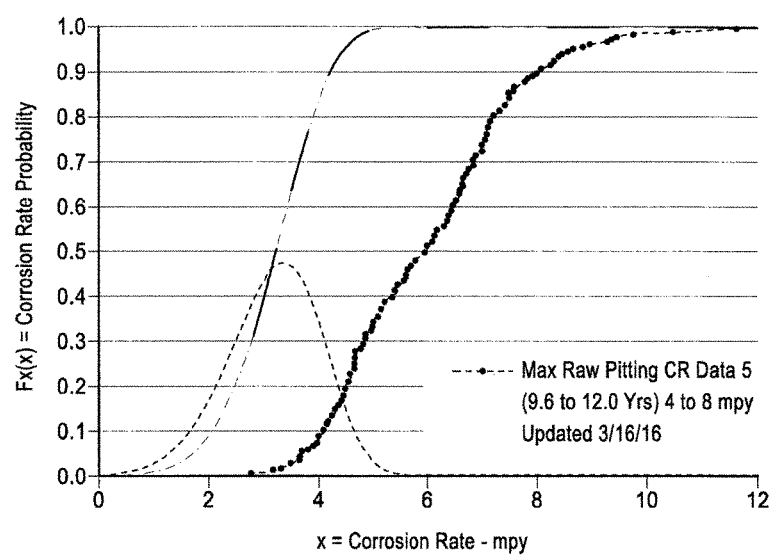

FIG. 37 illustrates the final selected fit for $F_X(x)$ for values of $\gamma=-0.987$, $\beta=5.700$, and $\eta=4.500$ that produced a survival probability of 40.26% with an age y of 20.00 years and COV of 0.266.

Figure 38:
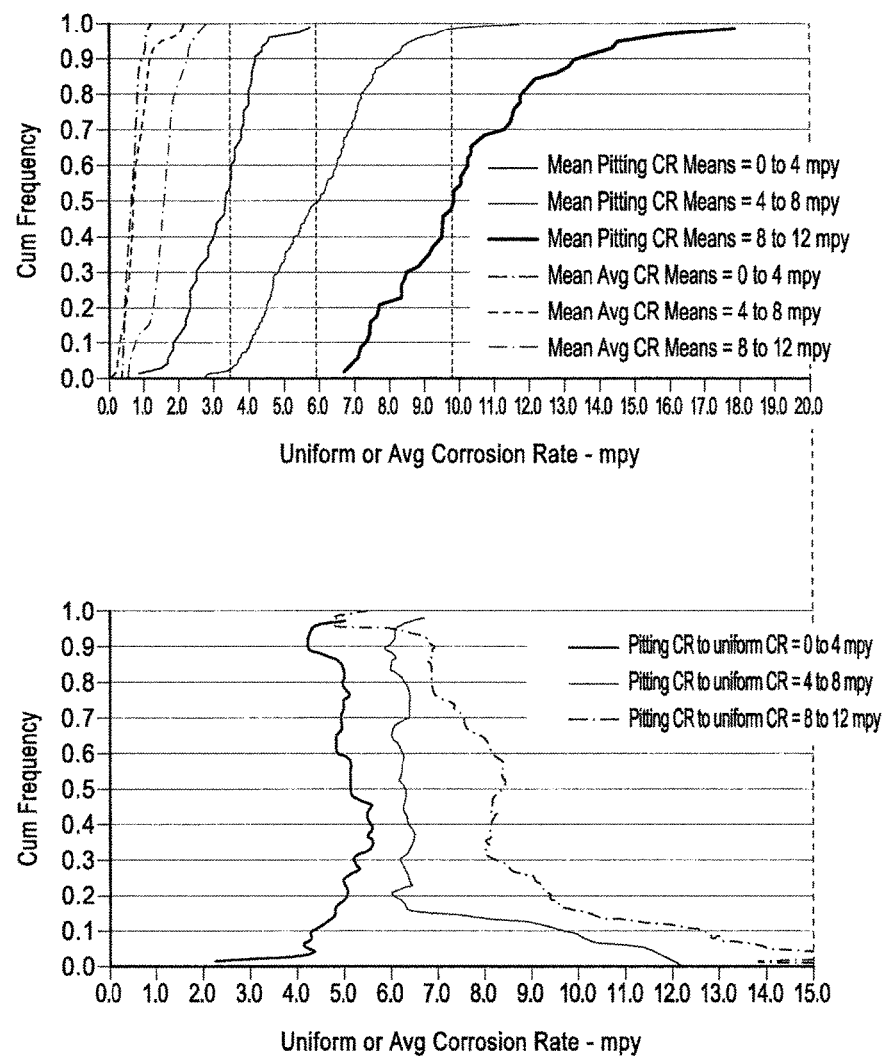

FIG. 38 Illustration of the three $F_X(x)$'s presented in FIGs. X.7.2-X.7.4 for the corrosion rates due to pitting depth and uniform corrosion rate ($<CRpitting>$, $<CRuniform>$, raw CRpitting, raw CRuniform) and (B) the ratio of the raw pitting to uniform corrosion rate (Ratiopit to uniform=raw CRpitting/CRuniform).

Figure 39:
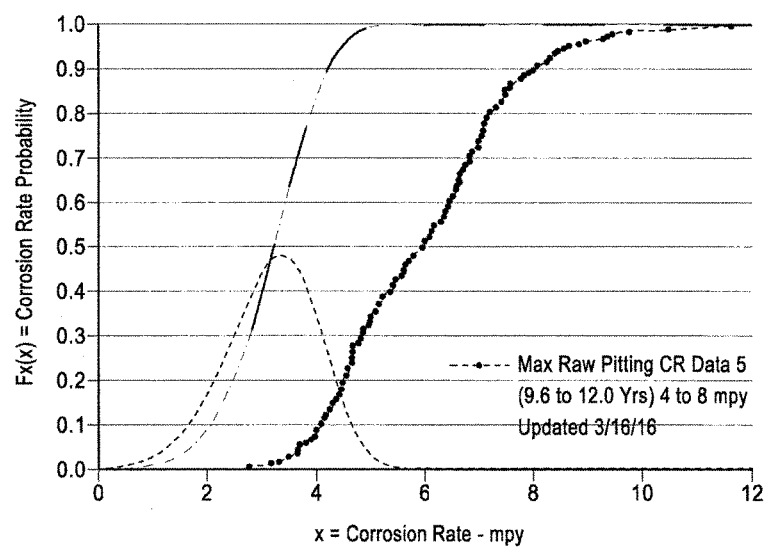

FIG. 39 illustrates $F_X(x)$ and $f_X(x)$ for a $CR_{max}$ of 4.48 mpy using corrosion data with values between 4 and 8 mpy. The dashed line represents the Weibull CDF fit to the empirical CFD.

Figure 40:
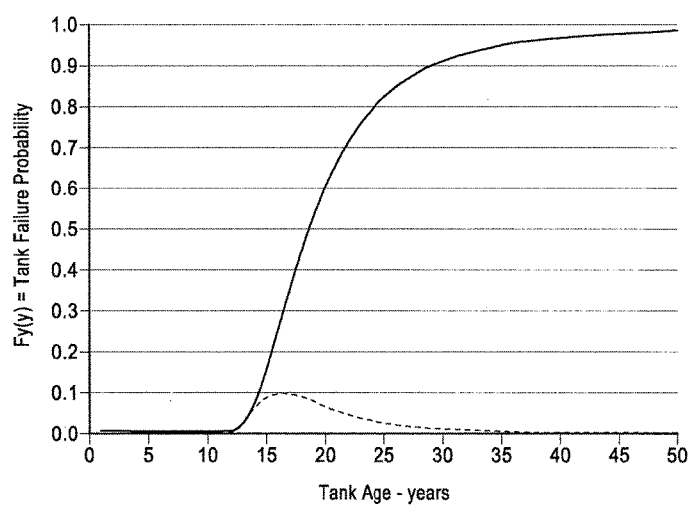

FIG. 40 illustrates $F_Y(y)$ and $f_Y(y)$ for $F_X(x)$ in FIG. 39 using the Weibull CDF.

Figure 41:
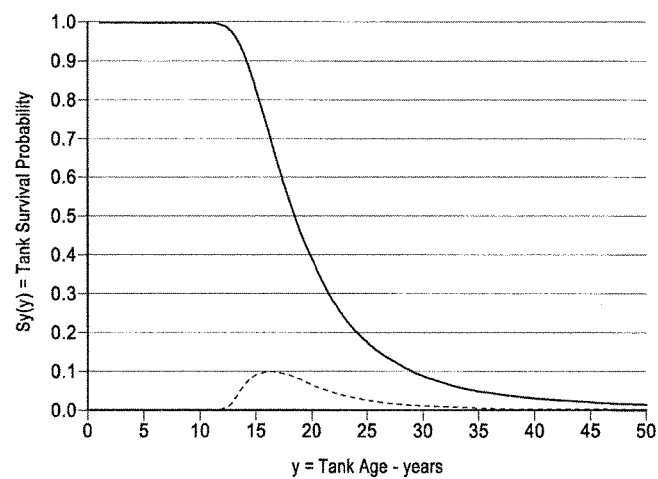

FIG. 41 illustrates $S_Y(y)$ and $s_Y(y)$ for $F_Y(y)$ and $f_Y(y)$ in FIG. 40.

Figure 42:
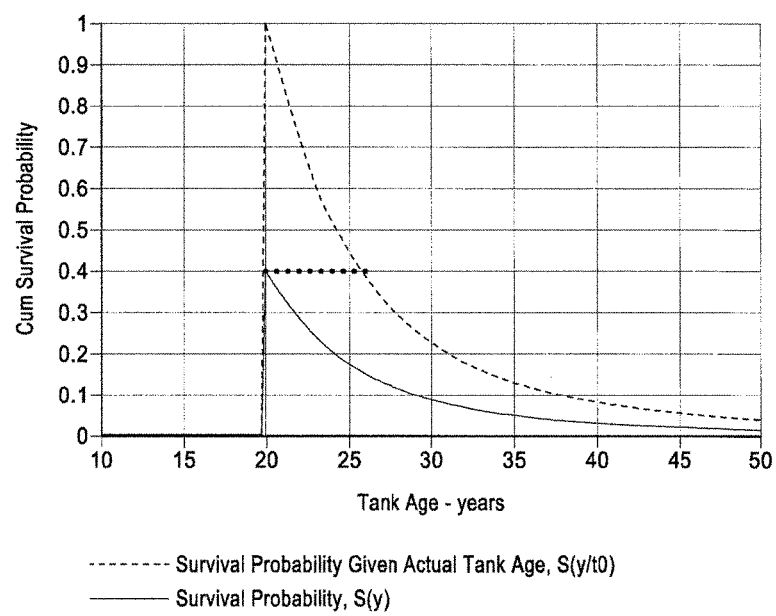

FIG. 42 illustrates $S_Y(y)$ and $S_Y(y/t_0)$ superimposed on $S_Y(y)$ between $y=t_0$ and $y=t_N$, where $S_Y(y=t_N/t_0)=S_Y(y=t_0)$, for $F_X(x)$ in FIG. 39 to illustrate the determination of TNI-ER using Equivalent Risk.

FIG. 43 illustrates the input and output of the Excel worksheet that determines TNI with No Additional Measurements in Step 10.

Figure 44J:
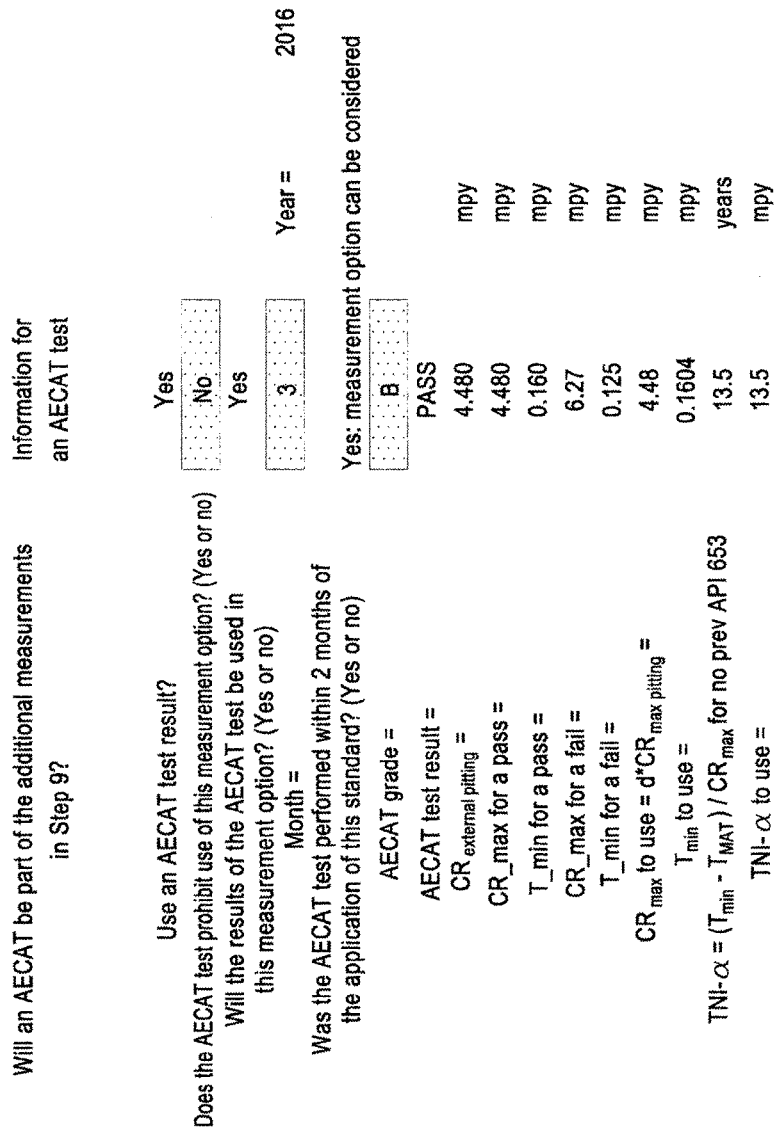

FIG. 44 illustrates the input and output of the Excel worksheet that determines TNI with the results of only an AECAT test in Step 10.

Figure 45J:
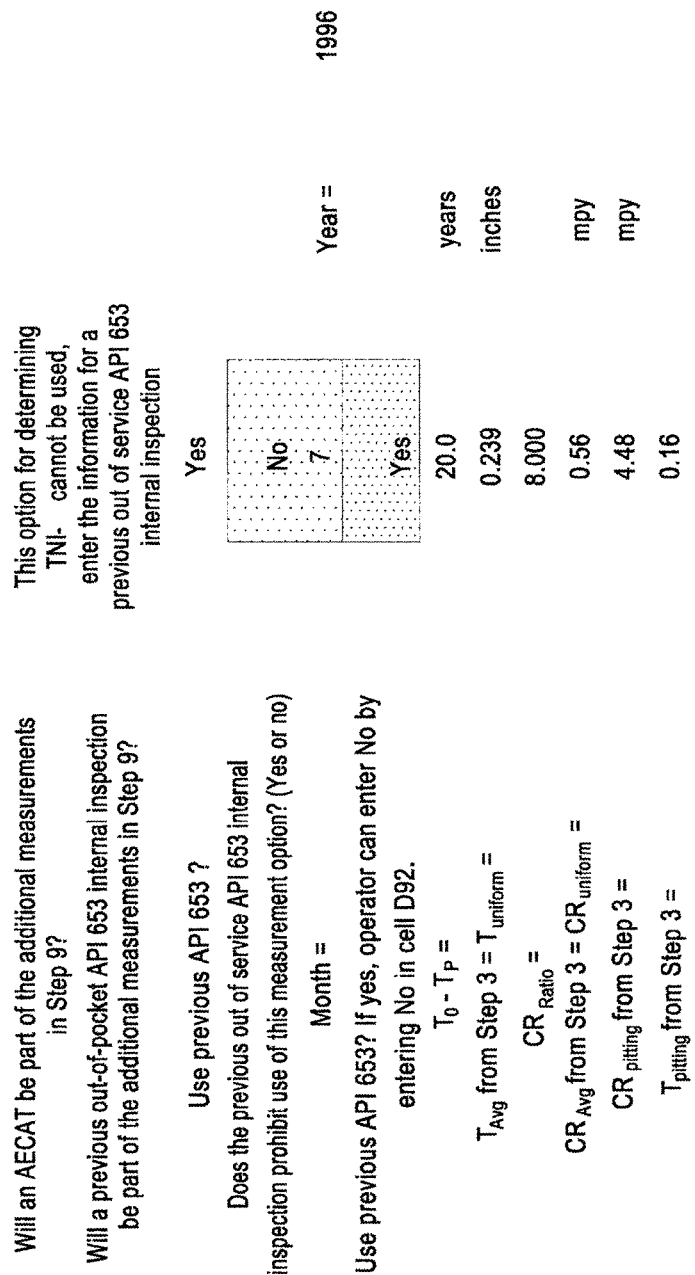

FIG. 45 illustrates the input and output of the Excel worksheet that determines TNI with the results of only a previous out-of-service API 653 internal inspection in Step 10, FIG. 46 illustrates the input and output of the Excel worksheet that determines TNI with the results of both an AECAT test and a previous out-of-service API 653 internal inspection in Step 10.

DESCRIPTION OF THE PREFERRED EMBODIMENT

1. Background

The methods of the present invention are based on the methods and apparatuses taught by Maresca and Maresca, et. al., in U.S. Pat. No. 9,228,932 and at least four patent applications: (1) "A Method for Extending the Time Between Out-of-Service, In-Tank Inspections," (2) "A Method and Apparatus for Determining the Time Between Internal Inspections of a Tank," and (3) "A Method and Apparatus for an In-Service Measurement of the Bottom Thickness and Corrosion Rate of a Tank Bottom," and (4) "A Measurement-based, In-service Method for Updating the Internal Inspection Interval of an AST." The methods of the present invention describe a method and apparatuses for determining the time until the next internal inspection (TNI) by and combining the Bayesian survival probability approach taught in these patents to determine TNI-ER using Equivalent Risk and TNI-α determined from additional measurements of the entire tank bottom for higher survival probability tank bottoms. This specification focuses on accurately, reliably, and safely determining TNI by combining the results of TNI-ER and TNI-α taught in these previous patents and patent applications.

2. Scope

The scope of the methods of the present invention are described below. They are similar to the scope of the methods and apparatuses described in the patent and patent applications by Maresca and Maresca, et. al., listed above.

2.1. This method provides a quantitative in-service, measurement-based method for determining the time (TNI) between (1) the application of this method and (2) the time at which an out-of-service, internal inspection of a steel, field-erected aboveground storage tank (AST) should be performed. This method can be used to check or update the internal inspection interval specified in Section 6.4.2 of API 653 for the next out-of-service internal inspection for either an initial inspection (Section 6.4.2.1) or a subsequent inspection (Section 6.4.2.2). In accordance with API 653, TNI is based upon not exceeding the minimum allowable thickness ($T_{MAT}$) of the tank bottom specified in API 653.

2.2. This method can be used to determine TNI without any additional risk of tank bottom failure during the entire time period defined by TNI. During this entire TNI time period, the risk or probability of tank bottom failure is lower than the risk or probability of tank bottom failure determined at the time of the application of the method. For this method, tank bottom failure is defined by $T_{MAT}$.

2.3. This method was developed for and can be used for ASTs with steel bottoms containing refined petroleum products or water. Refined petroleum products might include, for example, gasoline, diesel, and jet fuels.

2.4. This method can also be used for bulk underground storage tanks (bulk USTs) with vertical walls and a flat steel bottom containing a refined petroleum product, like those owned and operated by Department of Defense (DoD).

2.5. This method provides a step-by-step method that can be implemented for the tank of interest using actual measurements of the condition (thickness, corrosion rate, and integrity) of the bottom (or floor) of the tank made directly in or on the tank of interest at the time of the application of this method.

2.6. This method can be applied at any time during the service life of a tank, including any time between a previous out-of-service internal inspection and the internal inspection interval determined in the previous internal inspection, or any time since the installation of a new tank or the refurbishment or replacement of a tank bottom.

2.7. This method has a number of important applications specified in or directly relevant to internal inspection standards like the one in API 653. A few beneficial examples are indicated below:

2.7.1 This method can be used for checking or updating the internal inspection interval of an AST specified in Section 6.4.2 of API 653 for an Initial Inspection (Section 6.4.2.1) or a Subsequent Inspection (Section 6.4.2.2) at the time it is due for an out-of-service internal inspection to determine if there is any additional service life in the tank bottom.

2.7.2 This method can be used to perform the 10-year re-assessment for those tanks that have previously undergone an out-of-service API 653 internal inspection using a Risk Based Inspection (RBI) method (as required by Section 6.4.2.1.2 and Section 6.4.2.2.2 of API 653).

2.8. The references to API 653 in this method refer to the $5^{th}$ edition, but this method is also applicable to previous editions of API 653 such as the $3^{rd}$ and $4^{th}$ editions.

2.9. This method refers to and is applied in accordance with and in conjunction with API 653. This method can also be applied in accordance with and in conjunction with other industry-accepted practices for an out-of-service, internal inspection that are primarily controlled by the condition of the tank floor applicable standards, like STI SP001 for shop-fabricated steel ASTs. (For convenience and clarity, this method refers to API 653 throughout this method when referring to an out-of-service internal inspection of an AST (or a bulk UST). Any reference to API 653 made in this method, however, can be replaced with a reference to any of the other applicable standards that also require an out-of-service internal inspection in which corrosion of the tank bottom controls the life expectancy of the service life of the tank.)

2.10. This method can be re-applied more than once during the service life of a tank provided that the total service life of a tank does not exceed the maximum internal inspection internals specified in API 653 for an Initial Inspection (Section 6.4.2.1) or a Subsequent Inspection Section 6.4.2.2), which is currently 20 years for a tank without a RPB or 30 years for a tank with a RPB. These maximums can be exceeded if TNI-ER provides more time.

2.11. If TNI determined by this method is greater than 10 years, then this method requires that TNI be limited to 10 years. TNI can be re-assessed at 10 years, however, or any time during this 10-year interval using this method, provided that Section 2.10 is met.

2.12. If the sum of TNI determined by this method and the time ($t_0$) since the tank was initially installed or since the last out-of-service internal inspection exceeds the maximum time limit established in Sections 6.4.2.1 and 6.4.2.2 in API 653 (also stated in Section 2.10 of this standard), then TNI should be limited to the difference in this maximum internal and $t_0$ (TNI=20-$t_0$ for a tank without a RPB and TNI=30-$t_0$ for a tank with a RPB). These maxima can be exceeded if $t_0$ is less than the maxima and TNI is set equal to TNI-ER.

2.13. This method can be applied to both single- and double-bottom tanks.

2.14. For single-bottom tanks, Section 2.5 of this method shall include (1) passing a leak detection integrity test performed with a leak detection method that was evaluated by an independent, third-party using an industry accepted evaluation protocol (see Appendix 14 for a definition of Third-Party Evaluation) like those approved or accepted by one of the following: (*a*) the NWGLDE (see Appendix 14 for a definition of NWGLDE) or (b) an industry recognized evaluation organization; (2) making measurements of the thickness and the average or uniform corrosion rate of the bottom of the tank of interest at one or more locations; and (3) having completed an API 653 external inspection in accordance with the criteria specified in this standard indicating that the tank does not need to be taken out of service for an API 653 internal inspection. Section 2.5 may also include the use of the bottom thickness measurement results made in a previous out-of-service API 653 internal inspection, which (a) were performed in accordance with API 653, (b) meet the criteria for their use specified in this method, (c) has a probability of survival of greater than 50%, and (d) updates proportionally the maximum corrosion rate determined in this previous API 653 internal inspection using the thickness and corrosion measurements made in (2) of this section.

2.15. For double bottom tanks, Section 2.5 of this method shall include (1) passing a leak detection integrity test performed with a leak detection method (a) that was evaluated by an independent, third-party using an industry accepted evaluation protocol like those approved or accepted by the NWGLDE, (b) an industry recognized evaluation organization, (c) a PE, or (d) by passing a leak detection integrity test specified for a single-bottom tank in Section 2.14; (2) making measurements of the thickness and the average or uniform corrosion rate of the bottom of the tank of interest at one or more locations; and (3) having completed an API 653 external inspection within the last 5 years in accordance with the criteria specified in this standard indicating that the tank does not need to be taken out of service for an API 653 internal inspection. Section 2.5 may also include the use of the bottom thickness measurement results made in a previous out-of-service API 653 internal inspection, which (a) was performed in accordance with API 653, (b) meets the criteria for its use specified in this method, (c) has a probability of survival of greater than 50%, and (d) updates proportionally the maximum corrosion rate determined in this previous API 653 internal inspection using the thickness and corrosion measurements made in (2) of this section.

2.16. Any leak detection integrity test that is listed by the NWGLDE or was evaluated by an independent, third-party using a NWGLDE evaluation protocol is approved for use in Section 2.14 (1) or Section 2.15 (1).

2.17. This method recommends that an external inspection shall continue to be performed in accordance with API 653 on a 5-year schedule during the TNI time frame, or if not, this method recommends that TNI be defined by the 5-year anniversary of the last 5-year external inspection performed.

2.18. Additional measurements, as specified in this method, of the thickness and corrosion rate for the entire tank bottom can be used to increase the TNI computed using only the measurements of Sections 2.14 or 2.15. Two measurement methods, used alone or in combination, include (1) an acoustic emission (AE) test of the corrosion activity of the tank bottom showing that no or minimal corrosion activity is present, and/or (2) at least one previous out-of-service internal inspection performed in accordance with API 653 (or other industry accepted standards) that is updated proportionally using the thickness and corrosion measurements in Sections 2.14 or 2.15.

2.19. As stated in Sections 2.14 and 2.15, this method recommends that the condition of the shell (i.e., walls of the tank), roof, bottom-shell joint (previously known as the chime), and other appurtenances should be assessed as part of this method to validate the use TNI based on the corrosion of the tank bottom. This can be accomplished by reviewing a previous or performing a new in-service external inspection of the tank in accordance with (1) API 653, or equivalent standards for the tank of interest, or (2) a method approved by a PE that is no less stringent than (1). If a previous API 653 external inspection is used, it should be current, i.e., within 5 years of the previous external inspection, or this method should not be applied. This method recommends performing a new API 653 internal inspection if the previous external inspection is older than 4 years.

2.20. This method can be used for ASTs containing products other than refined petroleum products or water when the corrosion conditions of the tank bottom are appropriately accounted for, either by using the corrosion data provided in this method for generating the corrosion rate distribution for the tank of interest, if applicable, or by using the alternative method provided in this method for generating a new corrosion rate probability distribution applicable for the product and tank of interest.

2.21. The values stated in inch-pound units are to be regarded as standard.

2.22. This method description does not purport to address all of the safety concerns, if any, associated with its use. It is the responsibility of the user of this method to establish appropriate safety and health practices and determine the applicability of regulatory limitations prior to use.

3.1. This method provides a quantitative method for checking or updating the time until the next out-of-service internal inspections (i.e., internal inspection interval) as used by API Recommend Practice 653 ($3^{rd}$, $4^{th}$, and $5^{th}$ eds.) or by other consensus and/or regulatory standards based on the condition of the bottom of an AST or a bulk UST being considered for an out-of-service internal inspection using an in-service inspection method without requiring the use of nearby tanks, a control tank, or an evaluation of all or most of the tanks in the storage tank facility.

3.2. This method determines the internal inspection interval for the statistical population of tanks for which the tank of interest being evaluated belongs based on in-service measurements of the integrity, thickness, and corrosion rate of the tank bottom.

3.3. This method provides a quantitative procedure for checking and/or updating the time until the next out-of-service internal inspection, TNI, at any time during the life of a tank based on the corrosion and operational conditions of the tank without taking the tank out-of-service.

3.4. This method can be used to determine whether or not a tank scheduled for an out-of-service internal inspection needs to be done when scheduled, or can the inspection be rescheduled to a later time based on an updated determination of internal inspection interval that allows continued service of the tank.

3.5. Section 3.4 can be implemented without increasing the risk or probability of failure of the tank.

3.6. This method can also be used to determine the Initial internal inspection interval for a new tank.

3.7. This method can also be used to perform a 10-year Re-assessment of a tank that used an RBI method to determine the internal inspection interval in API 653 ($3^{rd}$, $4^{th}$, and $5^{th}$ eds).

3.8. This method provides up to five specific measurement, test, and inspection methods for determining the internal inspection interval or time until the tank should be taken out of service for an internal inspection.

2.9 This method can be used to safely and cost effectively minimize the number of out-of-service API 653 internal inspections, which (1) significantly minimizes the potential for environmental pollution that occurs every time an out-of-service internal inspection occurs when a tank is opened to the atmosphere, drained, and cleaned, (2) significantly reduces the actual costs associated with unneeded inspections or pre-mature or unnecessary maintenance or repairs, (3) significantly reduces the loss of the revenue associated with the loss of operational service that occurs when unneeded inspections, maintenance, or repairs are performed, and (4) significantly reduces the avoidance costs associated with undetected leaks and tank bottom failures.

4. Summary of Method

This method is described in six major Activities comprised of 12 Steps. Tables 1 lists and summarizes briefly the activities and specifies the steps associated with each activity. Table 2, which is provided and described in Section 4.2, summarizes how to easily and efficiently implement the method using simple input data and an Excel spreadsheet provided by Vista Precision Solutions, Inc., to perform all of the statistical and mathematical calculations required to determine and output TNI. This use of the Excel worksheet is the recommended approach for implementing this method. Table 3, which is provided and described in Section 4.3, lists and summarizes the 12 individual steps associated with each activity. A detailed description of how to implement each of the 12 steps is in provided in Section 5.

TABLE 1

Summary of the Six Activity, 12-Step Method

| Activity | Activity Title | Steps | Output |
|---|---|---|---|
| 1 | Does the Tank Owner/Operator Want to Use this Method, i.e., What Benefit (or Benefits) Does the Tank Owner/Operator Receive by Applying this Method? | 1 | Do you want to use this method? Yes or No. |
| 2 | Perform In-Service Measurements on the Tank of Interest to Determine If the Tank Meets the Minimum Requirements for the Application of the Method, i.e. Can the Method be Used? | 2, 3 | Do you meet the minimum criteria to use this method? Yes or No. Measure $CR_{max}$ and $T_{min}$ |
| 3 | Determine the Corrosion Rate Distribution, $F_X(x)$, for the Tank of Interest. | 4 | Generate or Select $F_X(x)$ |
| 4 | Determine the TNI based on the Survival Probability of the Tank, $S_Y(y)$, and Equivalent Risk (TNI-ER). | 5-8 | Generate $F_Y(y)$, $S_Y(y)$, and $S_Y(y/t_0)$ from $F_X(x)$, and Compute TNI-ER |
| 5 | Determine the TNI based on additional measurements of the thickness and corrosion across the entire tank bottom (TNI-a). | 9-11 | Determine TNI-α |
| 6 | Determine TNI from TNI-ER and TNI-a, where TNI ≤ 10 years. | 12 | Determine TNI |

These activities and steps presented in Tables 1-3 are summarized in three incremental descriptions in Sections 4.1-4.3 using the following three increasingly detailed flow charts: (1) FIG. 1 (in Section 4.3.1), (2) FIG. X2.1 (in Section 4.3.2), and (3) FIG. X2.2 (in Section 4.3.3). Section 4.3.1 provides a general overview and presents the background for the method. Section 4.3.2 provides a straightforward way to implement this method using an Excel worksheet to perform the calculations. Section 4.3.3 provides a detailed overview of all 12 steps to implement this method. These steps and a detailed procedure for implementing them are presented and described in Section 5. Seven Annexes and 14 Appendices support and illustrate the implementation of this method. They are listed in Tables 4 and 5 in Section 5.

As summarized in Table 2 in Section 4.2, examples of how to implement the method are presented using an Excel spreadsheet to perform all of the statistical and mathematical calculations required to determine and output TNI. This approach is useful to take, because it eliminates the mathematical and calculation complexity of the method before its implementation is explained in detail.

Table 2 summarizes how to implement this method using the tank bottom measurement results made in Steps 2 and 3 of Activity 2 and the Excel spreadsheet. The Excel worksheet is provided as part of this method to perform all of the calculations in Steps 3-9, 11, and 12 that are needed to determine TNI and output the results. If additional measurements of the tank bottom measurements are made or are available, which meet the criteria in Step 10, the Excel worksheet will also include them in the calculation of TNI.

This implementation of the method eliminates the need for a detailed understanding of and the performance of the statistical and mathematical calculations that are needed to implement the method. The Excel spreadsheet is straightforward to use and only requires the input of a number of simple parameters like the age of the tank, the results of a test as a PASS or FAIL, and some in-service tank bottom thickness and corrosion rate measurements. This worksheet approach is described in more detail below in Section 4.2.

4.1 General Overview. Section 6.4.2 of API 653 defines both conventional inspection methods (Section 6.4.2.1.1) and risk based inspection (RBI) methods (Section 6.4.2.1.2) for determining either the initial (Section 6.4.2.1) or the subsequent (Section 6.4.2.2) Internal Inspection Intervals (the time between two successive out-of-service internal inspections or the time between the installation of a tank and the first out-of-service internal inspection) based on the maximum corrosion rate, $CR_{max}$, the minimum thickness, $T_{min}$, and the minimum allowable thickness of the tank bottom, $T_{MAT}$, (as described by Table 4.4 in Section 4.4.6.5 of API 653). Sections 6.4.2.1.1 and 6.4.2.2.1 of API 653 describe the initial and subsequent internal inspection intervals, respectively, for conventional inspection methods, and Sections 6.4.2.1.2 and 6.4.2.2.2 describe the initial and subsequent internal inspection intervals for risk based inspection (RBI) methods.

This method is a measurement-based method that provides a "quantitative and in-service" procedure for checking and/or updating the internal inspection interval determined at the last out-of-service API 653 internal inspection. TNI, the time between (1) the application of this method and (2) the time at which an out-of-service internal inspection, such as that described in API 653 for a steel, field-erected, aboveground storage tank (AST) containing a petroleum product, will be performed without exceeding the minimum allowable thickness ($T_{MAT}$) of the tank bottom in accordance with API 653. This method also determines the time, TNI-ER, to the next out-of-service internal inspection without any additional risk of tank bottom failure. Because of the in-service measurements and the novel use of a Bayesian tank failure/tank survival methodology, during the entire time interval determined by this method, TNI, the risk or probability of tank bottom failure is lower than the risk or probability determined at the time of the application of the method.

This method can be applied directly on the tank of interest. This method and the value of TNI determined using it is very conservative (in terms of accuracy and reliability), because it is implemented using (1) current and actual bottom measurements in the tank of interest and (2) the minimum allowable bottom thickness, $T_{MAT}$, criteria specified in API 653 (either 0.05 in. or 0.10 in., as appropriate or required) when determining the maximum tank bottom corrosion rate, $CR_{max}$, in Step 3 and the cumulative density functions (CDFs) of $F_X(x)$, $F_Y(y)$, $S_Y(y)$, and $S_Y(y/t_0)$, which are used to determine TNI for the tank of interest, in Steps 4-8 (Activities 3 and 4).

$F_X(x)$ is generated for the tank of interest by fitting a Weibull probability distribution to a cumulative frequency distribution (CFD) of applicable corrosion rate data. $F_Y(y)$, $S_Y(y)$, and $S_Y(y/t_0)$ are then generated directly from $F_X(x)$, where (1) $F_Y(y)$ is the CDF of the failure of the tank bottom that is computed directly from $F_X(x)$, (2) $S_Y(y)$ is the CDF of the survival of the tank bottom that is computed directly from $F_Y(y)$, and (3) $S_Y(y/t_0)$ is the Bayesian update of the tank survival CDF that is computed directly from $S_Y(y)$ at the time of the application of this method, $t_0$. Once $S_Y(y)$ and $S_Y(y/t_0)$ have been generated for the tank of interest, TNI can be determined using Equivalent Risk.

$T_{MAT}$ is the minimum bottom thickness at which a tank would be taken out of service for maintenance and repair and is a built-in factor of safety when defining the maximum corrosion rate and the tank failure and survival probability functions. It has long been used by API and the oil and gas industry to indicate when a tank should be taken out of service for maintenance and repairs. $T_{MAT}$ is 0.05 in. for tanks with a release prevention barrier (RPB) and 0.10 in. for tanks without a RPB. $T_{MAT}$ acts as a factor of safety in the determination of TNI, because it is typically between 20% and 40% of the total thickness of a new tank bottom (typically, 0.25 in.).

It is important to note that $F_X(x)$ is generated from corrosion data and that these data could have been used directly to generate and use the cumulative frequency distributions (CFDs) of $F_Y(y)$, $S_Y(y)$, and $S_Y(y/t_0)$ instead of a statistical probability distribution like the Weibull distribution. This would have required transforming these data on a point-by-point basis from $F_X(x)$ to $F_Y(y)$ to $S_Y(y)$ to $S_Y(y/t_0)$. Instead, this method fits a Weibull probability CDF distribution to $F_X(x)$ by a trial and error least squares curve fitting method and then computes $F_Y(y)$, $S_Y(y)$, and $S_Y(y/t_0)$ for this Weibull distribution by using a method mathematical transformation described in Annex A6. Thus, while $F_Y(y)$, $S_Y(y)$, and $S_Y(y/t_0)$ are represented by mathematical functions, they are each fully supported by data.

This method can be applied at any time in the service life of a tank to determine TNI. As indicated in Section 2.7.1, an important time to apply this method is near or at the time when the tank is scheduled for out-of-service internal inspection to check if there is additional service life left in the tank, i.e., the remaining tank bottom thickness is greater than $T_{MAT}$. This schedule would be based on the most recent internal inspection interval determined in the last out-of-service API 653 internal inspection or a previous application of this method. This method can be used to update the internal inspection interval made previously (typically, 10 years, or more earlier) using the TNI determined with this method. As another application, indicated in Section 2.7.2, this method can also be used to perform re-assessment at the 10-year interval required by API 653 for an internal inspection performed using an RBI Method as specified in Sections 6.4.2.1.2 and 6.4.2.2.2 of API 653. There are also a wide range of other applications (not specifically indicated herein) that this method can be used to address.

All of these applications have very substantial environmental, operational, cost-saving and cost avoidance benefits. For example, the environmental risk associated with the potential release of petroleum vapors associated with opening and emptying the tank for an out-of-service internal inspection is eliminated. Also, this method reduces the operational downtime per tank from weeks or months, which is required for an out-of-service API 653 internal inspection, to a day or two, which is required to implement this method. The cost savings associated with the application of this method are real, immediate, and substantial and could be over 80 to 90% of the total cost of an out-of-service API 653 internal, which includes both the inspection and any maintenance or repairs. The cost savings can be calculated from the difference in cost between the application of this method and the performance of an out-of-service internal inspection, before considering the loss of revenue due to the operational downtime required to perform the internal inspection. Finally, this method minimizes avoidance costs such as the eventual cleanup costs associated with a leak that may have gone undetected.

Consistent with API 653, the use of this method to determine TNI is based on an assessment of the risk of failure of the bottom (or floor) of an AST (or an applicable bulk UST). Corrosion of the tank bottom is the most prevalent failure mode of a tank and is difficult to assess because of the lack of access to the tank bottom unless the tank is taken out-of-service, emptied, and cleaned for an internal inspection. Other potential but less common modes of failure are also checked during an out-of-service API 653 internal inspection (e.g., the shell, the roof, appurtenances, etc.), but it is the thickness and corrosion rate of the tank bottom that controls and is used to determine the internal inspection time interval in API 653 (Section 6.4.2). This method provides a quantitative, in-service method to check and update the condition of the tank bottom between out-of-service internal inspections. This method requires that the previous API 653 653 External Inspection be reviewed to determine if there are any potential failure modes not associated with the tank bottom that would preclude applying this method. If a previous API 653 external inspection is used, it should be current, i.e., within 5 years of the previous external inspection, or this method should not be applied. This method recommends performing a new API 653 internal inspection if the previous external inspection is older than 4 years. While not required, this method highly recommends that an API 653 External Inspection be included when applying this method.

This method requires in-service measurements of the integrity, thickness, and corrosion rate of the bottom of an AST (or a bulk UST) at the time, $t_0$, when this method is applied. These measurements can both determine the condition of the tank bottom and be used to generate the survival probability distribution of the tank bottom ($S_Y(y)$). It can also be used to generate the conditional survival probability distribution, $S_Y(y/t_0)$, i.e., the survival probability given that the tank bottom has not failed at the time, $t_0$, of the in-service measurements. $S_Y(y/t_0)$, can be determined directly from $S_Y(y)$; this is described in Annex A7 and illustrated in Appendices 6, 8, and 9. This method determines TNI using Equivalent Risk, which is the time it takes for the conditional survival probability determined from and at the time of the in-service measurements to decrease to the same survival probability as when the in-service inspection was performed as part of this method, i.e., TNI-ER=(y2=$t_N$)-(y1=$t_0$), where $t_N$ is the time when $S_Y(y=t_N/t_0)=S_Y(y=t_0)$. It is important to re-emphasize that the survival probabilities during this entire time interval, TNI-ER, are always higher than at the time of the in-service inspection. This method uses similar Bayesian (i.e., conditional probability) methods like those used by the life insurance industry to compute the survival age of a person given that the person has survived to a certain age, but the survival probability distributions in this method are used very differently. Equivalent Risk is determined by this method where life expectancy is determined by the life insurance industry.

Survival for a tank is determined by whether or not it passes a leak-detection integrity test with a method that adheres to the criteria in this method (see Sections 6, 7, 8, and 10-12). The underlying survival probability distribution, $S_Y(y)$, and the conditional update of this survival probability distribution, $S_Y(y/t_0)$, are determined from the bottom thickness and the bottom corrosion rate measurements made in the tank of interest as part of Step 3 of this method.

This method provides a table of the parameters of the corrosion rate distributions, $F_X(x)$s, for a range of pitting uniform corrosion rates, $CR_{max}$, with means 1 mpy and 18 mpy and a method for determining $F_X(x)$ for the tank of interest using these distributions (see Appendix A12.). The Excel spreadsheet provided with this method can be used to calculate and display the maximum corrosion rate data as a CFD and the CDF fit to this empirical CFD in terms of a three-input Weibull probability distribution with parameters γ, β, and η, where γ, β, and η are parameters that control the location, shape, and scale of the Weibull distribution. $CR_{max}$, is determined from the in-service measurement of the average or uniform corrosion rate, $CR_{avg}$ made in Step 3. As stated above, once $F_X(x)$ is generated, failure, survival, and condition survival probability cumulative density functions $F_Y(y)$, $S_Y(y)$, and $S_Y(y/t_0)$ are mathematically computed and used to determine TNI-ER. $F_Y(y)$, $S_Y(y)$, and $S_Y(y/t_0)$ can be generated by direct mathematical calculation using the values of γ, β, and η that were used to describe $F_X(x)$ by using the equations in Annexes A3, A6, and A7 of this method, or preferably by using the Excel spreadsheet provided. Once $S_Y(y)$ and $S_Y(y/t_0)$ are generated, this method determines the time interval, TNI, between $t_0$, the time at which this method is applied, and $t_N$, the time of the next scheduled out-of-service internal inspection using Equivalent Risk, as described in Annex 7.

The CDF of the tank failure distribution, $F_Y(y)$, is derived directly from the transformation of the empirically derived CFD of corrosion rate distribution, $F_X(x)$, as described in Annex 6, and the CDF of the survival distribution, $S_Y(y)$, is computed by subtracting $F_Y(y)$ from one, i.e., $S_Y(y)=1-F_Y(y)$. In addition to the library of empirically derived functions for $F_X(x)$ in Table X12.2, a table of $F_Y(y)$ and $S_Y(y)$ is provided in terms of γ, β, and η for $CR_{max}$ between 1 and 18 mpy in 1 mpy increments in Table X12.2 of Appendix X12. Each $F_X(x)$ generated by this method was derived from a trial and error least squares fit of a Weibull distributed $F_X(x)$ to the CFD of an extensive corrosion rate data set generated over an 18-year period (see Table X12.1 of Appendix X12 for illustrations of the data from several sites). Appendix X10 illustrates how to use the Excel worksheet to obtain an acceptable fit. The criteria for an acceptable fit is based on a good visual fit to the data with particular emphasis on the best fit being obtained for the smaller corrosion rate data (i.e., longer survival rates) provided that the minimum least squares error for the corrosion rate error in x of ±0.5 mpy, or less, and for the probability of occurrence error in $F_X(x)$ of ±5%, or less. As indicated above, the fits and errors are summarized in Table X12.2 of Appendix X12.

This method uses a Weibull probability distribution to describe $F_X(x)$, because (1) it accurately describes the extreme-valued nature of this empirical CFD distribution, and (2) it is the historical distribution of choice for describing the statistics of survival and reliability problems. Since $F_X(x)$ is used to obtain $F_Y(y)$ and $S_Y(y)$ by mathematical transformation (see Annex 6), $F_Y(y)$ and $S_Y(y)$ are also Weibull distributed.

This method requires that the CFD of the corrosion rate data shall contain at least 50 independent corrosion rate samples. In this method, we have use corrosion rate data obtained for years at over 47 locations throughout the US (see Appendix X.12). The corrosion rate CFD in this method was derived from over 336 independent samples using the corrosion data obtained between 9.6 and 12.1 years after burial. Alternatively, $F_X(x)$ can be generated for the tank of interest using at minimum of 50 independent out-of-service API 653 internal inspection reports for tanks with the same corrosion and operational conditions to determine the information required from the API reports.

As indicated above, this method shall make and use the following measurements (designated in Steps 2 and 3 of Activity 2): (1) a leak detection integrity test with a test result of PASS using a method that meets the criteria specified in this method for single- and double-bottom ASTs (and bulk USTs) and (2) local measurements of the thickness and the corrosion rate of the bottom of the tank measured in at least one location. In addition, this method can use one or more of the additional measurement methods described in Step 10 of Activity 5 to obtain a better determination of the corrosion conditions for the entire tank bottom to improve the accuracy and reliability of the determination of TNI made using the measurements in (1) and (2). These additional measurement methods include: (a) an AE Corrosion Activity Test (AECAT) of the bottom of the tank showing no/minimal active corrosion activity (Grade A or B in [11]) with the additional criterion that there are no local regions of concentrated corrosion activity in the Grade B test result, (b) a previous out-of-service API 653 Internal Inspection with bottom thickness measurements of the entire tank bottom with at least one thickness measurement in proximity to the local measurement made in (2), or (c) a combination of (a) and (b). This method allows for other methods to be used if they meet the criteria required for the use of the measurement methods in (a) and (b). All measurements used in this method that were obtained in Steps 2 and 3 and for the measurements in (a), (b) and (c) in Step 10 shall be completed within a two-month period of to, where to shall be based on the date of the completion of the passing leak detection integrity test.

The in-service measurements made as part of this method in Steps 2, 3, and 10 use sensor and detection measurement systems and methods accepted and used by the petroleum industry for ASTs and the DoD for ASTs and for bulk USTs. The computations to implement this method can be done analytically using the equations in Annexes A3, A5-A7, but this method provides and recommends using the Excel spreadsheet provided with this method to perform the calculations and to display the results of the calculations.

4.2 Implementation Using Table 2—

As summarized in Table 2, this method is very easy to implement using the Excel worksheet provided as part of the method once several simple measurements on the tank of interest are successfully performed. Using the tank bottom corrosion data measured in Step 3, the Excel worksheet outputs TNI-ER in Step 8. If one or more of the additional measurements specified in Step 10 are successfully made, then TNI-α can be determined in Step 11. If both TNI-ER and TNI-α are made, then TNI is derived from them when the probability of survival of the tank bottom is greater than 50%. If the probability of survival is less than 50% or no additional measurements were made to determine TNI-α, then TNI=TNI-ER. Additional measurements beyond Step 8 are not required to determine TNI (from TNI-ER).

TABLE 2

Implementation of this Method with the Provided Excel Worksheet

| Procedure | Description of Procedure |
|---|---|
| 1 | Perform Steps 1, 2, and 3 to obtain input information for Input to the Excel Worksheet. This information includes $CR_{avg}$ at $t_0$, $T_{avg}$ at $t_0$, $T_{avg}$ at $t_P$, $T_{MAT}$, $t_0$, $t_P$. Determine if $T_{avg}$ is thick enough to prevent a breach of the Tank Bottom. |
| 2 | Use Excel Worksheet and Enter the Information from Step 3 and Step 10 if the Integrity Test in Step 3 was a PASS. If the results of the Integrity Test was a FAIL or if $T_{avg}$ is too small to prevent a breach of the tank bottom, then this method recommends an out-of-service API 653 internal inspection. |
| 3 | Output Method Form from Annex A1. |

Alternatively, this method can be applied by first undertaking an extensive data collection and compilation procedure to develop a corrosion rate database to determine $F_X(x)$ instead of using the corrosion rate database and $F_X(x)$'s provided in the method. Also, this method can be applied by solving a variety of complex statistical and mathematical equations provided as part of this method using $F_X(x)$, regardless of how it is generated, and developing the output in graphical and tabular displays following all 12 steps of the 12-step procedure provided herein in Section 5. In essence, the user can develop a special version of the Excel worksheet provided and then use it to implement this method, or the user can use the Excel worksheet provided as part of the method. If the Excel worksheet that is provided with this method is used, all of the calculations in this 12-step procedure will be implemented in the worksheet. If the Excel worksheet is not used, then the 12 step procedure must be implemented on a step-by-step basis as described in detail by this method in Section 13 and summarized briefly in Section 4.3. Use of the Excel worksheet is therefore highly recommended for the most efficient implementation of this method.

If the Excel worksheet provided as part of this method is used, then this method requires only the following quantities, measurements, and test results to determine TNI=TNI-ER based on Equivalent Risk: (1) the age of the tank at the time of the previous out-of-service internal inspection, $t_{P\ age}$, where $t_P = t_{P\ age}$, $-t_{P\ age}$; (2) the age of the tank when this method is applied, $t_{0\ age}$, where $t_0 = t_{0\ age} - t_{P\ age}$, (3) the in-service measurement of the average tank bottom thickness a one or more locations in the tank, $T_{0\ avg}$, at $t_{0\ age}$; (4) the measurement of the average tank bottom thickness, $T_{P\ avg}$ at $t_{P\ age}$, for the entire tank bottom from the UT measurements made during the out-of-service API 653 internal inspection (or new tank bottom thickness) after maintenance and repairs, (5) the measurement of the average bottom thickness, $T_{P\ min}$, at $t_P$, in close proximity to the location of the measurement of $T_{0\ avg}$, made from the previous out-of-service API 653 internal inspection (or new tank bottom thickness) after maintenance and repairs, and (6) a test result of PASS for a leak detection integrity test performed at $t_0$ that meets the criteria of this method.

If additional tank bottom measurements are made using one or more combinations of the specified methods in Step 10, then the following additional information can be entered into the worksheet: (7) the result of a AECAT test as a PASS or FAIL, if such a test is performed, (8) the output of a previous out-of-service API 653 internal inspection of the tank bottom ($T_{P\ avg}$, $T_{P\ min}$, and $CR_{P\ avg}$ from all of the UT measurements of the tank bottom before any maintenance and repairs are made, and (9) the output of the API 653 internal inspection in (8) for the minimum tank bottom thickness, $T_{P\ min}$, and the associated maximum corrosion rate, $CR_{P\ max}$, for the underside (external), topside (internal), and summation (underside plus topside), if such a previous API 653 internal inspection has been performed or is used.

If the tank does not pass the integrity test in Step 2, then this method cannot be used and shall not be applied. If the information in (1)-(6) or if the information in (1)-(9) are entered into the Excel worksheet provided as part of this method, all of the calculations will be performed (in Steps 3-9 and Steps 11 and 12), and the worksheet will output TNI on the method form shown in Annex A.1. The calculations include determining and outputting a table of (1) the uniform or average corrosion rate, $CR_{uniform}$, and the maximum corrosion rate, usually due to pitting, $CR_{max}$, (2) the average and minimum thickness, $T_{0\ avg}$ and $T_{0\ min}$, due to $CR_{uniform}$ and $CR_{max}$, respectively, (3) graphs of he Weibull CDF probability distributions for $F_X(x)$, $F_Y(y)$, $S_Y(y)$, and $S_Y(y/t_0)$ generated for $F_X(x)$ with a $CR_{max}$ for the tank of interest, (4) TNI-ER using Equivalent Risk determined from $S_Y(y)$ and $S_Y(y/t_0)$, and (5) a TNI report on a Standard Form as provided in Annex A1. Example illustrations of the CDFs of $F_X(x)$, $F_Y(y)$, $S_Y(y)$, and $S_Y(y/t_0)$ are provided in Appendices X3-X6. Four example illustrations are provided in Appendix X13 using the Excel worksheet. The different illustrations were due to different sets of additional measurements in Step 10. The four illustrations were made for the following cases: (1) No additional measurements, (2) Only AECAT; (3) only a previous out-of-service API 653 internal inspection, and (4) both (2) and (3). All four cases use the same $F_X(x)$ developed from the uniform and pitting tank bottom thicknesses and corrosion rates determined in Step 3. Appendix X13 shows the input and output of the Excel Worksheet for all four cases. Note, it was assumed that the results of an API 653 external inspection was reviewed or performed and that the results of this inspection did not prohibit the use of this method (i.e., suggest that a potential failure problems exists at another location besides the tank bottom).

4.3 Summary Flow Chart—Overview.

As stated above, the objective of this method is to determine the time interval between the application of this method and the time of the next, out-of-service, internal inspection (TNI). This method can be used to check and/or update the internal inspection interval determined in the previous out-of-service API 653 internal inspection. If a previous API 653 report does not exist, this method can still check and/or update the internal inspection interval. There are many applications of this method, two of the most beneficial are to determine TNI for one or both of the inspection applications indicated in Section 2.7.

This method provides an in-service, measurement-based, 12-step method to determine TNI=$\Delta t_{0-N}$=$t_N$-$t_0$, where TNI and $\Delta t_{0-N}$ are the times to the next out-of-service API 653 internal inspection. When this method is applied in accordance with API 653, the time to perform this out-of-service internal inspection would occur when the remaining tank bottom thickness, $T_0$, is equal to or greater than $T_{MAT}$.

4.3.1 Overview—

Figure 1A:
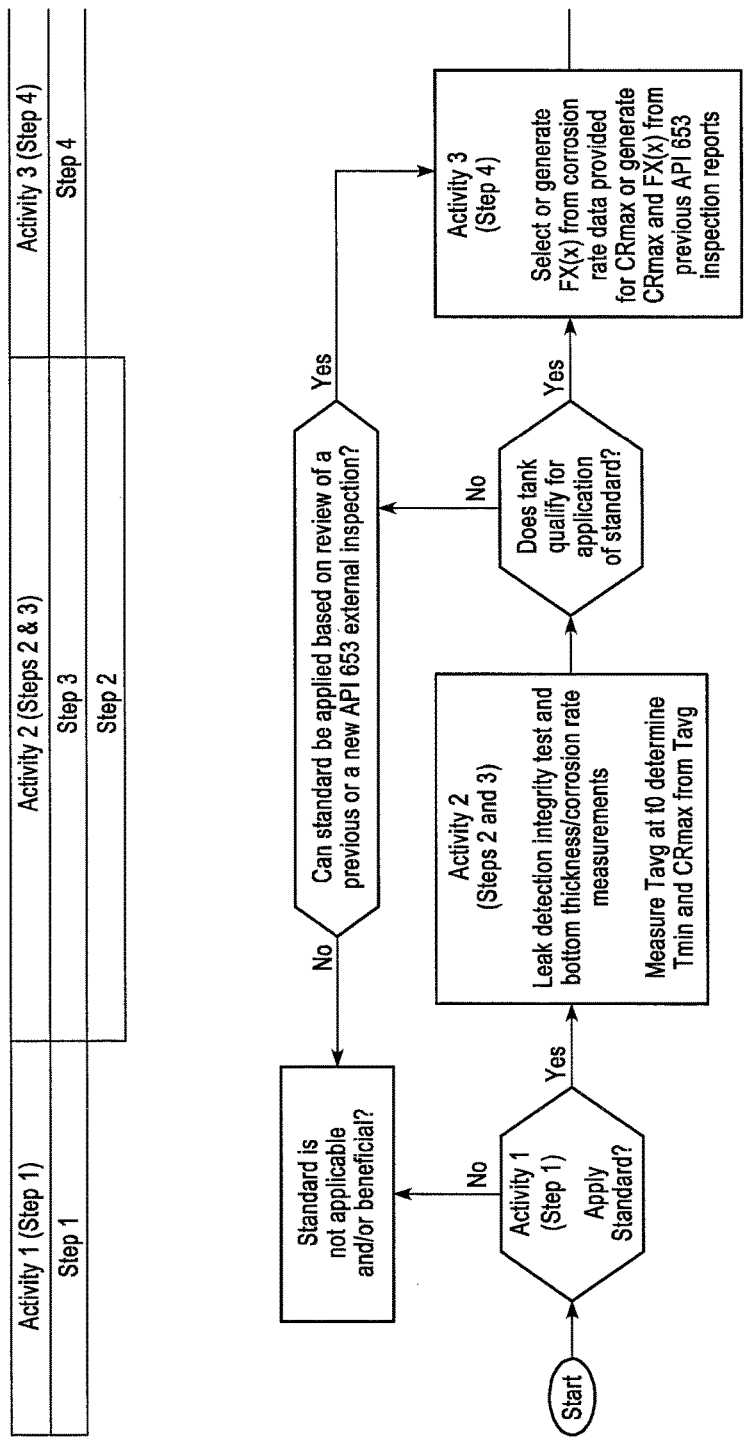
Figure 1B:
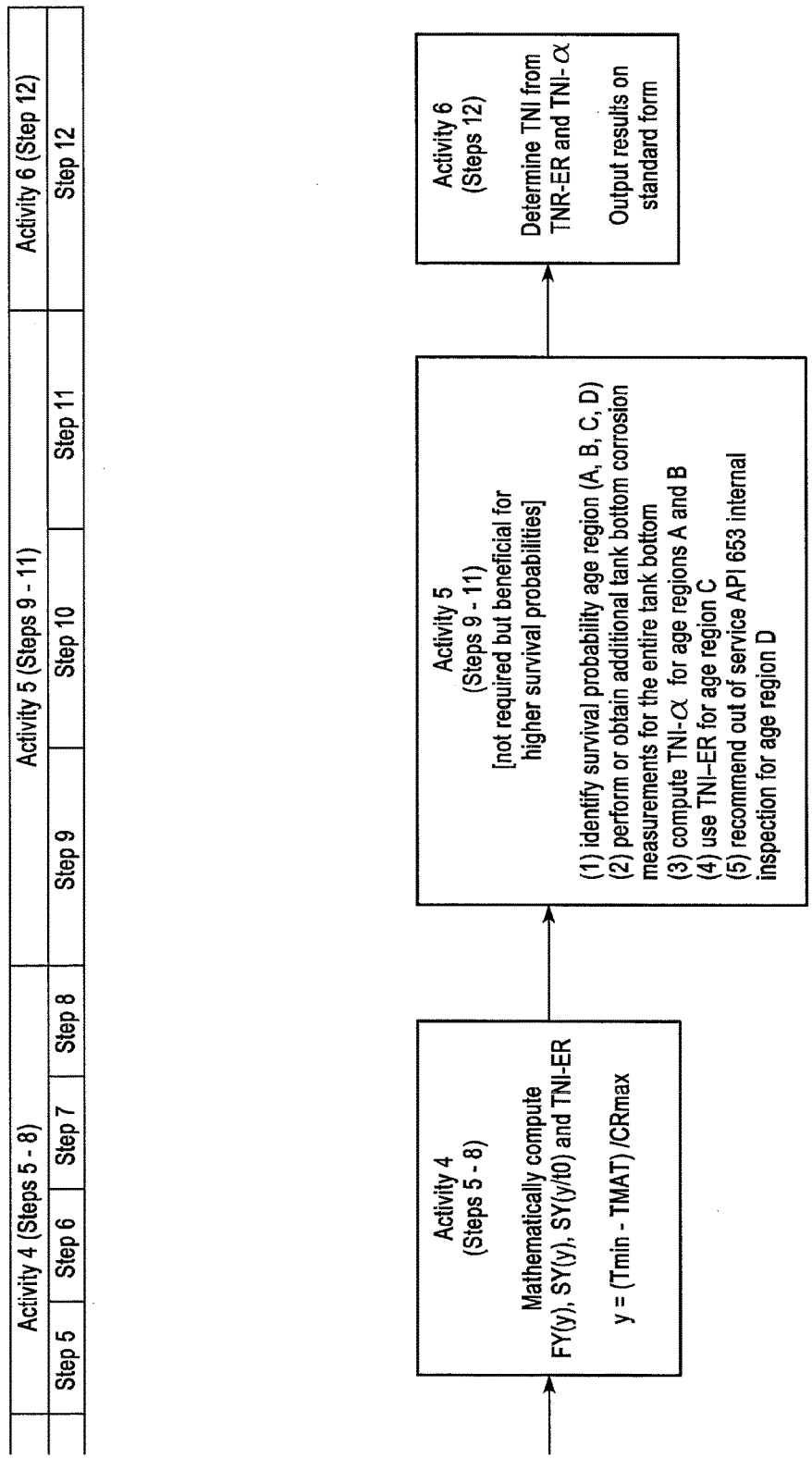

FIG. 1 and FIGs. X2.1 and X2.2 in Appendix X2 present increasingly more detailed flow charts of this 12-step method. FIG. 1 and Table 1 present the 12 step method in six major activities. FIG. X2.1 presents an overview of the six activities and the 12 major steps of the method, where each activity may be comprised of one to four steps. A more detailed flow chart and a tabular summary of the 12-step method are presented in FIG. X2.2 and Table 3. A brief description of each of the six activities and the 12 steps is presented below in this section and Sections 4.3.2 and 4.3.3; a complete description of the 12 steps is presented in Section 13.

As illustrated in FIG. 1 and Table 1, there are six major activities that need to be performed to implement this method, where each activity may contain one or more of the 12 individual steps. The first activity (Activity 1), which is addressed by Step 1, is to determine whether or not the tank operator/owner wants to use this method. This determination, among other things, depends on whether or not there is a beneficial application for updating and/or checking the internal inspection interval computed at the last out-of-service API 653 internal inspection or when the tank was installed. The second activity (Activity 2), which is addressed in Steps 2 and 3, is to determine whether or not this method can be used and involves measurements of the integrity, thickness, and corrosion of the tank bottom in the tank of interest.

If this method is applicable and can be used, then the next activity (Activity 3), which is addressed by Step 4, is to generate a cumulative density function (CDF) of the corrosion rate distribution to which the tank of interest belongs, $F_X(x)$, where x is the corrosion rate from a group of tank bottoms with the same corrosion and operational conditions. $F_X(x)$ is generated by fitting a Weibull CDF to an empirically derived cumulative frequency distribution (CFD) of the corrosion rate data from this group of tank bottoms. This fit is done by trial and error and must have a least squares error of ±0.5 mpy, or less, in corrosion rate and ±0.5%, or less, in cumulative probability of occurrence. While other extreme-valued functions could also have been used, a Weibull distribution is most frequently used for such survival and reliability problems.

The fourth activity (Activity 4), which is addressed by Steps 5-8, is to develop a failure probability distribution for the tank of interest, $F_Y(y)$, and then to generate a survival probability distribution, $S_Y(y)$, and a Bayesian update of this survival distribution, $S_Y(y/t_0)$ for this tank. $S_Y(y)$ and $S_Y(y/t_0)$ are then used to compute TNI-ER, the time to the next out-of-service internal inspection (TNI), based on Equivalent Risk (ER). All of the mathematical calculations required to implement Activities 3 and 4 (Steps 4 through 8) are provided in the equations in Annexes A3, A4, A6, and A7, which are easily performed in the provided Excel spreadsheet. Appendices X3–X9 illustrate the results graphically.

If additional measurements of the thickness and corrosion rate across the entire tank bottom are made or are available, and the probability of survival is greater than 50%, then the fifth set of activities apply (Activity 5). Using these additional tank bottom measurements, Steps 9-11 of Activity 5 can be followed to make a second estimate of TNI, which is denoted in this method by TNI-α. Finally, in the sixth activity (Activity 6), which is addressed by Step 12, TNI is determined from TNI-ER or from the combination of TNI-ER and TNI-α. If the selected TNI≥10 years, then TNI should be set to 10 years and a Re-assessment should be made in 10 years by re-applying this method.

Note that this method cannot be applied unless it can be established that the tank has survived to $t_0$, i.e., unless the tank passes a leak detection integrity test with a test method that meets the minimum requirements of this method. Note also that the maximum time between out-of-service API 653 internal inspections should be no longer than the maximum interval established by API 653. In API 653, this maximum interval is 30 years.

4.3.2 Summary Flow Chart—

The six activities briefly described above using FIG. 1 and Table 1 are described in more detail below using FIG. X2.1.

Activity 1 (Step 1): Does the Tank Owner/Operator want to Use this Method, i.e., What Benefit (or Benefits) does the Tank Owner/Operator Receive by Applying this Method?

Activity 1, which includes only Step 1 of the 12-step method, can be used to determine whether or not the tank operator or owner wants to apply this method (i.e., can the tank owner benefit by applying this method) for (1) checking and/or (2) updating TNI any point in time in the service life of a tank, such as the applications listed in Section 2.7. This method also allows the tank operator or owner to perform an out-of-service, API 653 internal inspection at any time regardless of the TNI, even if there is still useful life in the tank. Even if the tank owner/operator wants to use this method, it cannot be used if the tank bottom does not meet certain specific criteria determined from the in-service measurements of the tank bottom specified in Activity 2, Steps 2 and 3.

Activity 2 (Steps 2 and 3a,b,c): Perform in-Service Measurements on the Tank to Determine if the Tank Meets the Minimum Requirements for the Application of the Method, i.e. can the Method be Used?

Activity 2 is to make specific in-service measurements on the tank of interest to determine whether or not this method can be used, and if the method can be used, to use these in-service measurements to implement this method.

The following three sets of measurements should be made, but only the first two {shall} be made: (1) a leak detection integrity test with a test method/system that meets the criteria specified in this method (required), (2) in-service measurements of the thickness and corrosion rate of the tank bottom at one or more locations in the tank (required), and (3) an in-service API external inspection (highly recommended) in accordance with API 653. Whether or not this method can be used depends on the results of the required in-service measurements of the integrity of the tank bottom (Step 2) and the thickness and corrosion rate (Step 3) measurements that are made as part of this method. This method assumes, in accordance with an out-of-service API 653 internal inspection, that TNI is controlled by corrosion of the tank bottom. While this method does not require that this be performed, it highly recommends performing an API 653 external inspection to help validate the assumption that the tank bottom controls the TNI and that no other part of the tank (e.g., the tank walls) have experienced sufficient corrosion that might invalidate this assumption. This method does require that the previous API 653 653 External Inspection be reviewed to determine if there are any potential failure modes not associated with the tank bottom that would preclude applying this method. If a previous API 653 external inspection is used, it should be current, i.e., within 5 years of the previous external inspection, or this method should not be applied. This method recommends performing a new API 653 internal inspection if the previous external inspection is older than 4 years. While not required, this method highly recommends that an API 653 External Inspection be included when applying this method.

The objective of Step 2 is to determine whether or not the tank bottom has survived to time $t_0$. If the tank has survived to $t_0$, then its overall survival has increased over the original underlying survival probability distribution, ($S_Y(y)$). Passing a leak detection integrity test in accordance with this method addresses this survival requirement.

The objective of Step 3 is to make the measurements of bottom thickness, $T_{avg}$, at one or more locations on the tank bottom, and the corrosion rate, $CR_{avg}$, based on the minimum of the average these thickness measurements (if thickness measurements are made at more than one location) and to use these measurements in generating a corrosion rate distribution, $F_X(x)$, for the tank of interest. If the tank bottom thickness is less than $T_{MAT}$, then this method recommends that the tank be taken out-of-service for an API 653 internal inspection. If not, then the in-tank measurement of the tank bottom thickness can be used to determine $CR_{avg}$. The measurement of $CR_{avg}$ is then used to determine $CR_{max}$ and to select or generate the applicable $F_X(x)$ provided by this method.

$CR_{avg}$ is determined from the average in-service thickness measurements, $T_{0\ avg}$, made in the tank of interest, where $T_{P\ avg}$ was made at approximately the same location of the in-tank measurements made in the previous out-of-service API 653 internal inspection after the repairs and maintenance were complete and the tank was brought back into service.

$$CR_{avg}=(T_{P\ avg}-T_{0\ avg})/(t_P-t_0) \qquad (4.1)$$

$T_{0\ avg}$ is determined from a minimum of 8 (in 4 pairs of 2) and preferably 10 (in 5 pairs of 2) measurements of the bottom thickness at each location, where the second thickness measurement of each pair or replicate is made by lifting the probe off the bottom and then again placing it on the bottom for the second measurement. In general, $T_{P\ avg}$, which is typically determined at the last out-of-service internal inspection, will be comprised over only one or at most several thickness measurements, but this is acceptable because the measurements can be made more accurately and reliably when the tank is out-of-service.

It is assumed that the measurement of $CR_{avg}$ represents the underlying uniform corrosion rate of the tank bottom, $CR_{uniform}$. This assumption is valid, because the thickness measurement sensor systems that might be used to measure thickness cannot measure pitting depth, which usually represents the minimum thickness and the maximum corrosion rate: Other tests to help validate this assumption are described in more detail below. $CR_{max}$, which is used to implement this method and is used select or generate $F_X(x)$, is determined from the maximum pitting or thinning of either the underside (external side) or the topside (internal side) of the tank bottom, or both. This method provides and uses historical corrosion data to develop a relationship between $CR_{max}$ and $CR_{uniform}$ to determine $CR_{max}$. This method also provides an alternative method, described in more detail below, to determine $CR_{max}$ from $CR_{uniform}$. Once $CR_{max}$ is determined, it is used to generate or select $F_X(x)$ for a population of tank bottoms with the same corrosion and operational conditions.

It is important to note that there is no priority for making the measurements of integrity in Step 2 or the thickness and corrosion rate in Step 3. This is also true for performing an API 653 external inspection. Thus, the thickness and corrosion rate measurements made in Step 3 can be made before the integrity measurements in Step 2, and if an external inspection is made, it can also be made before or after these measurements. Such decisions can be made based on cost, environmental, and/or operational impacts.

Activity 3 (Step 4): Determine the Corrosion Rate Distribution, $F_X(x)$, for the Tank of Interest.

Activity 3, which is comprised of Step 4 (and an alternative method to Step 4 using previous out-of-service API 653 internal inspection reports), is to generate a corrosion rate distribution, $F_X(x)$, for a population of tanks with tank bottoms that have the same corrosion and operational conditions as the tank of interest. $F_X(x)$ will be used to generate the tank bottom failure ($F_Y(y)$) and the tank bottom survival ($S_Y(y)$) cumulative distribution functions (CDF). $F_X(x)$ will be developed using empirical corrosion rate data that are fit to a Weibull CDF. As stated above, a Weibull CDF is used, because it accurately describes the corrosion rate data and a mathematical function more easily facilitates the mathematical transformation required to generate $F_Y(y)$, $S_Y(y)$, and $S_Y(y/t_0)$ from $F_X(x)$. A least-squares algorithm is used to fit the corrosion rate data to the Weibull distribution, where the fit must meet minimum least squares error criteria in both x (±0.5 mpy) and $F_X(x)$ (±0.05=±5.0%).

Two general methods of generating $F_X(x)$ for the tank of interest are provided in this method. The first method, which is included as part of the method, is the simplest to use and is the preferred method. $F_X(x)$ for a wide rate of corrosion rate conditions was generated using a comprehensive study performed over 18 years at 47 sites located throughout the lower 48 states of the United States (see Annex A4 and Reference [7]). The second method, which is described in Step 4, is to generate $F_X(x)$ from previous out-of-service API 653 internal inspections that might include the tank of interest. The historical corrosion data provided by this method allow the user to implement this method anywhere in the United States or at other areas which have the same corrosion and operational conditions. If previous out-of-service API 653 internal inspection reports are used, then the corrosion conditions are typically limited to the location of the API 653 reports and the operational conditions of the tank of interest.

Activity 4 (Steps 5, 6, 7, and 8): Determine the TNI based on the Survival Probability of the Tank, $S_Y(y)$, and Equivalent Risk (TNI-ER).

Activity 3 is to generate a tank bottom failure and a survival probability cumulative distribution function, $F_Y(y)$ and $S_Y(y)$, respectively, and then use $S_Y(y)$ to generate $S_Y(y/t_0)$, a Bayesian update of $S_Y(y)$, to make a determination of TNI based on Equivalent Risk, i.e., TNI-ER. The magnitude of TNI-ER is controlled by the Survival Probability Age Region and the method deviation of the survival CDF, where TNI-ER increases as the Age Region and the method deviation increase.

This method generates $F_Y(y)$ from $F_X(x)$, $S_Y(y)$ from $F_Y(y)$, $S_Y(y/t_0)$ from $S_Y(y)$, and TNI from $S_Y(y)$ and $S_Y(y/t_0)$ in Steps 5, 6, 7, and 8, respectively. Step 5 is to generate $F_Y(y)$ from a mathematical transformation of the Weibull corrosion rate probability distribution, $F_X(x)$. This is accomplished in an Excel worksheet, but mathematical equations are also provided to compute $F_Y(y)$ in Annex A6. Step 6 is to generate $S_Y(y)$ from $F_Y(y)$, which is straightforward, because $S_Y(y)$ is obtained by a simple subtraction from one, i.e., $S_Y(y)=1-F_Y(y)$. Step 7 is to generate $S_Y(y/t_0)$, the Bayesian update of $S_Y(y)$, where $S_Y(y/t_0)$ is the probability of survival given that the tank bottom has survived to $t_0$; and $S_Y(y/t_0)$ is computed directly from $S_Y(y)$. Step 8 is to determine TNI-ER=$t_N-t_0$ by finding the time y2=$t_N$ where $S_Y(y2/t_0)$ equals $S_Y(y1)$ at y1=$t_0$. There are a variety of ways to perform the computation, but the spreadsheet facilitates the calculation and also graphically displays the result.

Activity 5 (Steps 9, 10, and 11): Determine the TNI based on additional measurements of the thickness and corrosion across the entire tank bottom (TNI-α).

Activity 5, which is addressed by Steps 9, 10, and 11, can be used to make another estimate of TNI (i.e., TNI-α), but only if (a) Additional Measurements of the thicknesses and corrosion rates across the entire tank bottom are obtained or are made and (b) the survival probability, $S_Y(y)$, at time y=$t_0$ is greater than 50%. Activity 5 provides a method for determining TNI-α, which may be greater than the TNI-ER determined from Equivalent Risk in Step 8. The final determination of TNI will be determined in Step 12 using TNI-ER or the combination of TNI-ER and TNI-α as described in Table 10.

The determination of TNI-α depends on (a) the survival probability age region and (b) the type and number of additional thickness and corrosion rate measurements. There are four survival probability age regions, with Age Regions A and D representing the tails of the survival probability distribution, $S_Y(y)$, and Age Regions B and C representing the central portion of the distribution. The four survival probability age regions are defined below:

Survival Probability Age Region A: $S_Y(y>95\%)$
Survival Probability Age Region B: $50\% \leq S_Y(y) \leq 95\%$
Survival Probability Age Region C: $5\% \leq S_Y(y) < 50\%$
Survival Probability Age Region D: $S_Y(y) < 5\%$ TNI-ER can be determined for Survival Probability Age Regions A, B, and C. If $S_Y(y)$ falls into Survival Probability Age Region D, which is defined by the upper tail of the $S_Y(y)$ distribution where the corrosion rate data used to generate $S_Y(y)$, are typically insufficient to accurately describe the distribution, then this method recommends that an out-of-service API 653 internal inspection be performed. If $S_Y(y)$ is in Survival Probability Age Regions A or B, then TNI-ER may be increased for this higher survival probabilities, as provided by this method, if sufficient thickness and corrosion data can be made or obtained for the entire tank bottom to justify such an increase. If $S_Y(y)$ is in Survival Probability Age Region C, where the probability of survival is less than 50%, then TNI can only be determined using TNI-ER.

It should be noted that the upper and lower tails of $S_Y(y)$ are defined at 95% and 5%, respectively. The percentage used to define the upper and lower tails can be changed to increase the size of Survival Probability Age Regions C and/or A if sufficient corrosion data are available to accurately define the tails of the distribution.

Three methods of acquiring additional information about the thickness and corrosion rate across the entire tank bottom are included and described as part of this method. These three methods include: (1) the results of an AE corrosion activity test (AECAT), which was conducted within the past 2 months, with a Grade A test result or a Grade B test result in which there are no focused locations of corrosion activity and the measurements of the thickness and corrosion rate of the tank bottom ($T_{avg}=T_{uniform}$ and $CR_{avg}=CR_{uniform}$; $T_{rain}$ and $CR_{max}$) made in Step 3 of Activity 2; (2) the results of a tank bottom inspection reported in a previous out-of-service API internal inspection and one or more measurements of the thickness and corrosion rate of the tank bottom ($T_{avg}=T_{uniform}$ and $CR_{avg}=CR_{uniform}$; $T_{min}$ and $CR_{max}$) made in Step 3 of Activity 2; and (3) combined results of (1) and (2) with $T_{min}$ and $CR_{max}$ being used to compute TNI-α.

This method recommends using either or the combination of an AECAT and a previous out-of-service API 653 internal inspection, because the performance of these measurements and the results of the tests are well documented and well understood.

If additional measurements of the thickness and corrosion rate of the entire tank bottom are not made or are not available from previous out-of-service API 653 internal inspection reports, then TNI is determined only from Equivalent Risk in Step 8.

Activity 6 (Step 12): Determine TNI from TNI-ER and TNI-α, where TNI≤10 Years.

Activity 6, comprised of Step 12, determines TNI from the maximum value of TNI-ER and TNI-a for Survival Probability Age Region A, the maximum value of TNI-ER and TNI-α for Survival Probability Age Region B, and TNI-ER for Survival Probability Age Region C. TNI is not determined for Survival Probability Age Region D, although it could if a portion of the tails are better defined and supported by additional data. If the tank falls into Age Region D, this method recommends that an out-of-service API 653 internal inspection be performed by the tank owner/operator. This method limits TNI to 10 years or less, but allows TNI to be updated at 10 years with a maximum of 30 years (in accordance with API 653) by implementing this method to determine if additional service life is available in the tank bottom.

4.3.3 Detailed Summary Flow Chart—

A more detailed Flow Chart than presented in FIG. X2.1 is presented in FIG. X2.2 and described below. The description of the activities and steps below add to the description in Section 4.3.2.

Activity 1 (Step 1): Does the Tank Owner/Operator want to Use this Method, i.e., What Benefit (or Benefits) does the Tank Owner/Operator Receive by Applying this Method?

The flow chart for Activity 1 in FIG. X2.2 shows a more detailed decision process for the tank owner/operator to determine if the tank owner/operator wants to use this method to compute TNI. This flow chart indicates that the method can be applied at any time, including when the tank is ready for a scheduled out-of-service API 653 internal inspection. It also includes the possibility of making the decision to perform an out-of-service API 653 internal inspection.

Activity 2 (Steps 2 and 3a,b): Perform in-Service Measurements on the Tank to Determine if the Tank Meets the Minimum Requirements for the Application of the Method, i.e. can the Method be Used?

The flow chart for Activity 2, comprised of Steps 2 and 3 in FIG. X2.2, shows a more detailed decision process to determine whether or not this method can be used/applied, i.e., does it meet the minimum criteria established in the method for its use? In FIG. X2.2, the in-service measurements and the decision process for each measurement are identified separately. As stated above, the order of performing Step 2 (i.e., the leak detection integrity test) or Step 3 (i.e., the in-service measurements of the thickness and corrosion rate measurements of the tank bottom at one or more locations) is not important providing that the criteria for both steps are met before proceeding to Activities 3 through 6. The order of testing can be determined by cost, operational, environmental, or safety impacts, but both steps should be completed within two months of applying this method at $t_0$, i.e., in the interval between $t_0-2$ months and $t_0$, where t0 is the time when the measurements for both Steps 2 and 3 are completed. A detailed description of the minimum criteria that needs to be met will be described in more detail under each Step in Section 13, which criteria include (1) a PASS for the leak detection integrity test, (2) a bottom thickness that is greater than the minimum allowable thickness, $T_{MAT}$, (where $T_{MAT}$ is 0.05 in. for a tank with a release prevention barrier (RPB) and 0.10 in. for a tank without a RPB), and (3) a corrosion rate that provides for greater than 1 year of service before the minimum allowable thickness criterion is met.

If the tank bottom passes these three criteria, then the tank owner/operator needs to determine whether or not an in-service API 653 external inspection should be performed as part of this method. The external inspection, which is routinely performed at 5-year intervals, provides the tank owner/operator with an assessment of whether or not the visible or accessible parts of the tank require that the tank be taken out-of-service for an API 653 internal inspection based on non-tank-bottom maintenance or repair requirements. While this method does not require that this be performed, it highly recommends performing an API 653 external inspection. This method does require, however, that the previous API 653 653 External Inspection be reviewed to determine if there are any potential failure modes not associated with the tank bottom that would preclude applying this method. If a previous API 653 external inspection is used, it should be current, i.e., within 5 years of the previous external inspection, or this method should not be applied. This method recommends performing a new API 653 internal inspection if the previous external inspection is older than 4 years.

Activity 3 (Step 4): Determine the Corrosion Rate Distribution, $F_X(x)$, for the Tank of Interest.

Activity 3, which is comprised of Step 4, provides, once the tank has met the minimum tank bottom criteria in Activity 2, a method (and an alternative method) for generating a corrosion rate distribution, $F_X(x)$ for the tank of interest. The method is to use the corrosion distributions, $F_X(x)$, provided as part of this method. The uniform or average corrosion rate, $CR_{avg}$, measured in Step 3, is used to determine the maximum $CR_{max}$ due to pitting and excessive local thinning, and $CR_{max}$ is used to select or generate a $F_X(x)$ to use.

Alternatively, the second method is for the tank owner/operator to generate $F_X(x)$ from previous out-of-service API 653 internal inspections for a group of tanks with tank bottoms that have the same operational and mean corrosion conditions (due to pitting and excessive local thinning) as the tank of interest. This alternative method requires at least 50 independent API reports be used, where only one report can be used per tank. The alternative approach requires assembling sufficient API 653 reports to develop FX(x) that accurately describes the operational and corrosion conditions of the tank of interest.

Activity 4 (Steps 5, 6, 7, and 8): Determine the TNI based on the Survival Probability of the Tank, $S_Y(y)$, and Equivalent Risk (TNI-ER).

Activity 4, comprised of Steps 5, 6, 7, and 8, uses the corrosion rate distribution, $F_X(x)$, which was generated for the tank of interest in Step 4 of Activity 3, to generate a tank bottom failure, $F_Y(y)$, and a survival probability distribution, $S_Y(y)$, and then use a Bayesian update of $S_Y(y)$ (i.e., $S_Y(y/t_0)$) to make a determination of TNI based on Equivalent Risk. While these calculations could be viewed as mathematically complicated, Activity 4 is straightforward to implement and is presented similarly in both flow charts shown in FIGs. X2.1 and X2.2. Knowledge of statistics, probability theory, and complex mathematics is not required to implement the method, because an Excel Worksheet is provided as part of this method to do the mathematics and to generate $F_X(x)$, $F_Y(y)$, $S_Y(y)$, and $S_Y(y/t_0)$. TNI-ER=$t_N-t_0$ is then computed directly from $S_Y(y)$ by determining what value of y for $S_Y(y/t_0)$ will have the same value as $S_Y(y=t_0)$, i.e., when $S_Y(y=t_0)=S_Y(y=t_N/t_0)$. The Excel worksheet can be used to generate and output TNI-ER and the four probability CDFs.

The worksheet can be used by entering the following input parameters into the worksheet: (1) the current age of the tank since the last out-of-service bottom inspection of the tank bottom (either a previous API 653 internal inspection or when the tank was new) at the time of the application of this method, $t_{0\ age}$ or $t_0$, (2) the mean (or median) measurement of the bottom thickness, $T_{0\ avg}$, in mpy made in Step 3 as part of this method at $t_{0\ age}$ or $t_0$, (3) the age of the tank when the thickness of the tank bottom was last made, $t_{P\ age}$, where $t_0 = t_{0\ age} - t_{P\ age}$ years and $t_P = t_{P\ age} - t_{P\ age} = 0$ years, (4) the mean (or median) thickness of the tank bottom at $t_{P\ age\ or}$ or $t_P$, at approximately the same location that $T_{P\ avg}$ was made at $t_{0\ age}$ or $t_P$, and (5) the minimum thickness and maximum corrosion rate thickness of the tank bottom at $t_{P\ age}$ or $t_P$, (if this information is available). If no additional measurements of tank bottom thickness or corrosion rates that accurately describe the pitting and thinning across the entire tank bottom is provided as part of Step 10 of Activity 5, the worksheet outputs TNI-ER for TNI. If additional spatial information describing the entire tank bottom is provided in Step 10 that meets the criteria in this method, the worksheet will also compute TNI-α as described in Activity 5, Step 11, and output TNI as indicated by Step 12 of Activity 6.

Activity 5 (Steps 9, 10, and 11): Determine the TNI based on additional measurements of the thickness and corrosion across the entire tank bottom (TNI-α).

Activity 5, which is addressed by Steps 9, 10, and 11, can be used to make a second determination of TNI (i.e., TNI-α), but only if (1) additional measurements of the thickness and corrosion rate across the entire tank bottom are obtained or are made in compliance with the criteria specified in this method and (2) the survival probability at time $t_0$ is greater than 50%. Activity 5 provides a method for determining TNI-α, which may be greater than the TNI-ER determined from Equivalent Risk in Step 8. The flow chart in FIG. X2.2 shows a detailed decision and measurement logic for collecting the additional measurements and using them to compute TNI-α. It is important to note that TNI can always be determined using TNI-ER without any additional tank bottom measurements, and an out-of-service API 653 internal inspection can always be performed at any time regardless of the value of TNI.

This method provides four acceptable methods for determining the maximum corrosion rate, $CR_{max}$, for determining TNI-α, where the method to use is specified in Tables 8 and 10. The details will be described below in Step 10, but a few overview comments about the use of AECAT and previous out-of-service API 653 internal reports summarized above in Section 4.3.2 are made first.

The results of an AE corrosion activity test (AECAT) can be used to extrapolate the results of the corrosion measurements made in Step 3 to the entire tank bottom. AECAT is used 1195 in this method to determine the lack of corrosion across the entire tank bottom, which is a very accurate and reliable measurement, as opposed to determining the presence of corrosion, which may be impacted with a high number of false alarms and missed detections [11]. Previous studies indicate that the AECAT method described herein can be applied to over {55%} of the tanks requiring out-of-service API 653 internal inspections [11]. The results of the thickness and corrosion rate measurements of the tank bottom made in Step 3 can be safely extrapolated to the entire tank bottom if the results of an AECAT test indicate a Grade A test result, or a Grade B test result in which there are no focused locations of corrosion activity. A Grade A test result indicates that no active corrosion activity is occurring in the tank. A Grade B test, after some further processing over that used in [11] to eliminate false alarms, indicates a similar result. Previous studies of {147} ASTs, which were taken out-of-service for an API 653 internal inspection after an AECAT test was completed, showed that tanks with a Grade A or Grade B required no maintenance or repair of the tank bottom. The same study also indicated that over 85% of the tanks taken out-of-service for an API 653 internal inspection did not actually need to be inspected at that time and could have safely remained in operation for many additional years [11].

Once it is determined that there is no active corrosion occurring in the tank (all of the Grade A and the applicable Grade B tanks tested), the thickness and corrosion rate data obtained in Step 3 can be extrapolated to the entire tank bottom. The advantage of this approach is that the results are (1) current, (2) apply to the entire tank bottom, and (3) cover at least 55% and up to 85% of all of the tanks for which this method may be applied.

The results of a tank bottom inspection reported in a previous out-of-service API 653 internal inspection can also be used to make an estimate of the minimum thickness and maximum corrosion rate for the entire tank bottom when adjusted proportionately by the results in Step 3 of this method. This second approach covers over 85% of the tanks for which this method may be applied. This approach uses the thickness and corrosion rate measurements across the entire tank bottom and assumes that the areas of highest corrosion (mainly due pitting and/or extreme thinning), which were identified and measured in the last internal inspection, continue to corrode at the same rate even though these areas were repaired during this last internal inspection. The maximum corrosion rate and the minimum thickness from this previous API 653 internal inspection are then multiplied by the ratio of the average corrosion rate measured in Step 3 and measured in the previous API 653 internal inspection at the same approximate tank-bottom location ($CR_{ratio}$).

There are several ways to use the results of the previous API 653 internal inspection of the tank bottom when determining $T_{min}$ and $CR_{max}$. One way is to use the sum of the underside and topside tank bottom thickness measurements to determine $T_{min}$ and $CR_{max}$, which is typically used when conducting out-of-service API 653 internal inspection and then to update $T_{min}$ and $CR_{max}$ by multiplying by $CR_{ratio}$. Another way is to use the maximum corrosion rate (typically, the underside corrosion rate) and then multiply by the product of $CR_{ratio}$, which is used when an RBI inspection methods is used following API 653. The third way is to multiply $T_{avg}$ and $CR_{avg}$ by a factor that accounts for both the underside and topside corrosion for the measurement made. API 653 suggests that the topside corrosion is 40% of the underside corrosion. The second option is the most representative, because the local spots of high corrosion controlling the computation of $T_{avg}$ and $CR_{avg}$ have been typically been eliminated in the previous out-of-service API 653 internal inspection because of the maintenance and repair of the tank bottom, and furthermore, the areas of maximum underside and topside corrosion are not likely to occur in the same locations. The first and third options are more conservative. In all cases, the application of $CR_{ratio}$ provides an accurate update of the corrosion conditions in the tank since the last API 653 internal inspection.

While this method provides for three methods of measuring the minimum floor thickness and maximum corrosion rate across the entire tank bottom, this method recommends using either the AECAT approach or a combination of the AECAT and the previous API 653 approaches, because they provide the most up-to-date assessments of the tank bottom. Once the spatial measurements of $T_{min}$ and $CR_{max}$ are obtained from any of the methods described herein, the TNI-α can be determined as described in Table 8 of Step 11.

Activity 5 (Step 12): Determine TNI from TNI-ER and TNI-α, where TNI≤10 Years.

Activity 6, comprised of Step 12, determines TNI from a combination of TNI-ER and TNI-α for Survival Probability Age Regions A, B, and C, and this combination is based on the Survival Probability Age Region and the type of Additional Measurements used in determining TNI-α. TNI is not determined for Age Region D, although it could if a portion of the tails are better defined and supported by additional data. If the tank falls into Age Region D, this method recommends that an out-of-service API 653 internal inspection be performed by the tank owner/operator. Stated differently, TNI is equal to TNI-ER unless additional measurements of thickness and corrosion rate across the entire tank bottom are sufficient to make it possible to determine TNI-α and to use it in determining TNI. Tables 9 and 10 summarize how to combine TNI-ER and TNI-α in each survival age region to determine TNI. This method limits TNI to 10 years or less, but allows TNI to be updated at 10 years by using this method. This method limits the total time between out-of-service internal inspections to 30 years, which is in accordance with API 653.

TNI-α is used in this method, because TNI-ER will tend to be short for the high survival probability regions (Age Regions A and B), because the tank has not survived long enough relative to its total expected service life to have experienced many of the potential failure mechanisms that might prematurely shorten the life of a tank.

If TNI-ER<1 year or TNI-α<1 year, this method recommends that the tank owner/operator perform an out-of-service API 653 internal inspection, but this decision is up to the tank owner/operator.

4.4 Summary of Each Step.

Each of the 12 steps is briefly summarized below. These steps, which are summarized in Table 3 and FIG. X3.2, are explained in more detail in Section 13 and in the Annexes A1-A7 and Appendices X1-X13.

Activity 1 (Step 1): Does the Tank Owner/Operator want to Use this Method, i.e., What Benefit (or Benefits) does the Tank Owner/Operator Receive by Applying this Method?

Step 1—Determine Whether or not the Tank Owner/Operator Wants to Use this Method, and if so, What Benefit (or Benefits) does the Tank Owner/Operator Receive by Applying this Method?

As indicated above, there are a wide range of benefits that might justify the use of this method by the tank owner/operator if the time to the next out-of-service API 653 internal inspection, TNI, at any time in the service life of a tank can be checked and/or updated. This includes, as stated previously, by applying this method at the time of a scheduled out-of-service API 653 internal inspection or to address the 10-year re-assessment for RBI methods. In addition to those mentioned, there are many more reasons that might benefit a tank owner/operator. For example, the TNI might be used to establish the TNI for a newly installed or a newly repaired tank, where the corrosion rate is unknown or not reliably known. As another example, this method might be used to assess the status of each tank in a facility during a sale of such facility. TNI might also be used to prioritize and manage the tank inspection, maintenance, and repair program in a facility based on tanks with the shortest TNI, i.e., highest risk of corrosion.

Activity 2 (Steps 2 and 3): Perform in-Service Measurements on the Tank to Determine if the Tank Meets the Minimum Requirements for the Application of the Method, i.e. can the Method be Used?

Step 2—Conduct a Leak Detection Integrity Test to Determine Whether or Not the Tank has Survived to the Time of Application of this Method, $t_0$.

Steps 2 and 3 are used to make specific in-service measurements on the tank of interest to determine whether or not the tank meets the minimum requirements for application of this method. As stated above, Steps 2 and 3 can be performed in any order. The specific objective of Activity 2 is to obtain the tank bottom data necessary to determine if specific criteria are met so that a Bayesian update of the survival distribution, $S_Y(y/t_0)$, can be generated.

TABLE 3

Summary of the 12-Step Method

| Step | Step Title | Activity | Output |
|---|---|---|---|
| 1 | Determine Whether or not the Tank Owner/Operator Wants to Use this Method, and if so, What Benefit (or Benefits) Does the Tank Owner/Operator Receive by Applying this Method? | 1 | Do you want to use this method? Yes or No. |
| 2 | Conduct a Leak Detection Integrity Test to Determine Whether or Not the Tank of Interest has Survived to the Time of Application of this Method, $t_0$. | 2 | A PASS means the tank has survived and is eligible to apply this method. |
| 3a | Measure the Thickness ($T_{uniform}$) and the Uniform Corrosion Rate ($CR_{uniform}$) of the Tank Bottom at One or More Locations and Determine the Maximum Corrosion Rate ($CR_{max}$) and Minimum Thickness, $T_{min}$, of the Tank Bottom to Use in Generating $F_X(x)$. | 2 | Measure $CR_{avg}$ & $T_{avg}$ at $t_0$ |
| 3b | Determine the Maximum Corrosion Rate ($CR_{max}$) from $CR_{avg}$ to Use in Generating $F_X(x)$. | 2 | Determine $CR_{max}$ & $T_{min}$ from $CR_{avg}$ & $T_{avg}$ at $t_0$ and Determine if $T_{avg} \geq T_{MAT}$. If $T_{avg} \geq T_{MAT}$, tank has survived and is eligible to apply this method |
| 4 | Generate a Corrosion Rate Distribution, $F_X(x)$, of the Tank Bottom for the Tank Being Evaluated based on a Population of Tanks Located in the Same Corrosion and Operational Environments. | 3 | Generate $F_X(x)$ |
| 5 | Generate a Tank Failure or Life Expectancy Probability Distribution CDF, $F_Y(y)$, for the Tank of Interest. | 4 | Mathematically compute $F_Y(y)$ |

TABLE 3-continued

Summary of the 12-Step Method

| Step | Step Title | Activity | Output |
|---|---|---|---|
| 6 | Generate a Tank Survival Probability Distribution CDF, $S_Y(y)$, for the Tank of Interest. | 4 | Mathematically compute $S_Y(y) = 1 - F_Y(y)$ |
| 7 | Generate the Bayesian Survival Probability Distribution $S_Y(y/t_0)$. | 4 | Mathematically compute $S_Y(y/t_0)$ from $S_Y(y)$ |
| 8 | Determine the Time to the Next Internal Inspection (TNI-ER) based on Equivalent Risk. | 4 | Determine TNI-ER using Equivalent Risk based on $S_Y(y/t_0)$ |
| 9 | Determine if Additional Thickness and Corrosion Rate Information of the Entire Tank Bottom be Made and Used to Improve TNI-ER? | 5 | Identify Survival Age Region and Determine if additional measurements of the entire tank bottom can be made, are available, or are qualify for use |
| 10 | Determine the Minimum Bottom Thickness and the Maximum Corrosion Rate for the Entire Tank Bottom Using One of Three In-service Measurement Methods. | 5 | Perform or use the measurements of the entire tank bottom to generate $CR_{max}$ & $T_{min}$ |
| 11 | Determine the Time to the Next Internal Inspection (TNI-α) based on Measurements of the Minimum Thickness and Maximum Corrosion Rate for the Entire Tank Bottom Made in Step 10. | 5 | Determine TNI-α from the Additional Thickness and Corrosion Rate Information for Entire Tank Bottom |
| 12 | Determine TNI from TNI-ER and TNI-a}, where TNI ≤ 10 years. | 6 | Determine TNI from TNI-ER and TNI-a using Table 10 |

To determine whether or not the tank has survived to an age of to, the tank shall perform and PASS a Leak Detection Integrity Test with a test method that meets the criteria in this method. If the tank has survived to $t_0$, then the underlying survival probability CDF, $S_Y(y/t_0)$, can be generated. Different test methods, which are in accordance with this method, can be used for single-bottom and double-bottom ASTs and bulk USTs.

There is a wide range of in-tank and ex-tank leak detection integrity systems for testing ASTs and bulk USTs. The in-tank methods include mass-based leak detection systems, including the LRDP, and systems that measurement liquid level and temperature as a function of liquid depth. One type of mass-based leak detection systems uses a reference tube, which is place vertically in the tank and is allowed to fill up with product. The differential pressure (i.e., the differential height changes) is monitored once the valve allowing the reference tube to fill with product is closed. Another type of mass-based leak detection systems is a bubbler differential pressure measurement system. The ex-tank systems include tracer systems, including those systems that place a unique liquid tracer in the product in the tank and monitor for its presence underneath the tank or monitor for the constituents that naturally exist in the product. The ex-tank systems also include electrical resistivity tomography (ERT) systems where an array of electrodes is place around the tank, where some of the electrodes may be located at prescribed depths and the presence of any product in the soil beneath the tank is detected electrically. These systems are typically used to determine the integrity (i.e., the presence of a leak) in a single-bottom tank, but can be used for double-bottom tanks as well.

There is also a wide range of leak detection integrity systems for double-bottom tanks. Some of these systems monitor for the presence of the accumulation of the liquid in a sump or the gaseous vapors that are present due to a product release in the interstitial space between the two bottoms. Other systems monitor for pressure changes in the interstitial space between the two bottoms if this space is sealed s0 that any increase or decrease in pressure can be monitored. The most common systems place the interstitial space under a small negative pressure. A hole in the bottom in contact with the soil will show an increase in pressure to atmospheric pressure, and a hole in the bottom in contact with the product in the tank will show an increase in pressure until the pressure in the interstitial space is the same as the pressure at the bottom of the product in the tank. Vista Precision Solution's Double-Bottom Pressure Decay Method monitors the pressure changes in a sealed double bottom.

Step 3a—Measure the Thickness ($T_{uniform}$) and the Uniform Corrosion Rate ($CR_{uniform}$) of the Tank Bottom at One or More Locations and Determine the Maximum Corrosion Rate ($CR_{max}$) and Minimum Thickness, $T_{min}$, of the Tank Bottom to Use in Generating $F_X(x)$.

The tank owner/operator {shall} make in-service, in-tank measurements of the bottom thickness and the corrosion rate at one or more locations on the tank bottom to use in generating or selecting a corrosion rate CDF, a tank failure CDF, and a tank survival CDF. The bottom thickness measurements should be made with a sensor system with a precision and accuracy of at least 0.010 in. The mean (or median) of a minimum of 8 to 10 thickness measurements at one location is used. If the measured thickness is less than $T_{MAT}$, then this method recommends that an out-of-service API 653 internal inspection be performed. Unless one or more of the 8 to 10 thickness measurements at the location with the smallest mean (or median) is greater than {3 to 5} method deviations than the mean (or median), this method assumes that this value is produced by uniform corrosion such that $T_{uniform}=T_{avg}$ and $CR_{uniform}=CR_{avg}$. Use of the median is most representative of uniform corrosion.

There is a wide variety of methods that have been used to measure the thickness of the tank bottom. These include ultrasonic thickness (UT) sensing systems, magnetic flux systems, a combination of UT and magnetic flux systems, EMAT systems, and LRUT systems to name a few. U.S. Patent Application by Maresca, et. al. entitled "A Method and Apparatus for an In-Service Measurement of the Bottom Thickness and Corrosion Rate of a Tank Bottom," describes a UT measurement approach whereby the UT sensing probe is inserted into the product in the tank and place on the bottom of the tank.

Step 3b—Determine the Maximum Corrosion Rate ($CR_{max}$) from $CR_{avg}$ to Use in Generating or Selecting $F_X(x)$.

The next step is to make an estimate of the maximum corrosion rate due to pitting or localized thinning, $CR_{max}$, from the uniform corrosion rate, $CR_{uniform}$, measured in Step 3a. Four methods are provided below to generate $CR_{max}$ from $CR_{uniform}$.

Method 1.

Use historical corrosion data provided by this method that provides a mathematical relationship between uniform corrosion, $CR_{uniform}$, and the maximum corrosion rate due to pitting, $CR_{max}$.

Method 2.

Use the corrosion rates measured in a previous API 653 internal inspection report and updated proportionately by the bottom thickness and the corrosion rate measurements made in Step 3 of this method.

Method 3.

Use an identical approach to Method 1 by developing a CDF from the corrosion rates of a population of tank bottoms with the same corrosion and operation conditions using previous out-of-service API 653 internal inspection reports. The measurements required will be the bottom thickness and corrosion rate at approximately the same location as the one used to collect these measurements in Step 3a of this method and the minimum thickness and the maximum external and internal corrosion rate results for each API 653 tank. The corrosion results from a minimum of 50 different tanks with the same corrosion and operational conditions shall be used.

Activity 3 (Step 4): Determine the Corrosion Rate Distribution, $F_X(x)$, for the Tank of Interest.

Step 4—Generate a Corrosion Rate Distribution, $F_X(x)$, of the Tank Bottom for the Tank of Interest being Evaluated Based on a Population of Tanks Located in the Same Corrosion and Operational Environments.

A CDF of the corrosion rates, $F_X(x)$, needs to be generated for a population of tanks with the same corrosion and operational conditions. This method provides two methods for generating $F_X(x)$: (1) Use of $F_X(x)$ as a function of $CR_{max}$ developed from 18 years of corrosion data and provided by this method ([11] and Annex A4), and (2) Use of an $F_X(x)$ developed from previous out-of-service API 653 internal inspections obtained for tanks with the same corrosion and operational conditions. A minimum of 50 independent corrosion samples comprising the corrosion and operational conditions that would be experienced by the tank of interest is needed to generate $F_X(x)$ for both cases. For the latter, 50 independent out-of-service API 653 internal inspections shall be used, where only one inspection report can be used per tank. For both methods a least squares fit of a Weibull CDF with an empirically derived CFD of the corrosion data is used to develop $F_X(x)$. A trial and error fit is used to minimize the error in x and y, where any error of ±0.5 mpy in corrosion rate and of ±0.05=±5% in corrosion probability will suffice. The trial and error fit begins with a visual fit to the corrosion data that best captures the data and also meets the minimum least squares error criteria.

Activity 4 (Steps 5 Through 9): Determine the TNI Based on the Survival Probability of the Tank, $S_Y(y)$, and Equivalent Risk (TNI-ER).

Step 5—Generate a Tank Failure or Life Expectancy Probability Distribution CDF, $F_Y(y)$, for the Tank of Interest.

The cumulative distribution function (CDF) of the tank failure CDF ($F_Y(y)$) is computed directly from $F_X(x)$ in Step 4 using a method mathematical transformation. This transformation is described in Annex A6.

Step 6—Generate a Tank Survival Probability Distribution CDF, $S_Y(y)$, for the Tank Being Evaluated.

The cumulative density function (CDF) of the survival probability distribution ($S_Y(y)$) is computed directly from $F_Y(y)$ in Step 5 using the equation $S_Y(y)=1-F_Y(y)$.

Step 7—Generate the Bayesian Survival Probability Distribution $S_Y(y/t_0)$.

$S_Y(y/t_0)$ is computed directly from $S_Y(y)$ generated in Step 6 using a method mathematical formula to generate conditional probabilities from an underlying probability function. This calculation is described in Annex A7.

Step 8—Determine the Time to the Next Internal Inspection (TNI-ER) based on Equivalent Risk.

The Time to the Next Internal Inspection (TNI-ER) is determined from $S_Y(y)$ and $S_Y(y/t_0)$ using Equivalent Risk. And is equal to $y2-y1=t_N-t_0$, which is defined when $S_Y(y1=t_0)=S_Y(y2=t_N/t_0)=[S_Y(y1=t_0)]^2$.

Activity 5 (Steps 9 Through 11): Determine the TNI Based on Additional Measurements of the Thickness and Corrosion Across the Entire Tank Bottom (TNI-α).

Step 9—Determine if Additional Thickness and Corrosion Rate Information of the Entire Tank Bottom be Made and Used to Improve TNI-ER?

Two decisions must be made. The first is determine whether or not measurements of the thickness and corrosion rate for the entire tank bottom can or needs to be made, and if so, can a deterministic determination of TNI-a be made. The second is to determine the survival probability age region of the tank for which the method is being applied.

Step 10—Determine the Minimum Bottom Thickness and the Maximum Corrosion Rate for the Entire Tank Bottom Using One of Three In-service Measurement Methods.

This method provides four methods for making a measurement of the minimum thickness, $T_{min}$, and the maximum corrosion rate, $CR_{max}$, for the entire tank bottom. These four methods are described in Section 5.

Step 11—Determine the Time to the Next Internal Inspection (TNI-α) based on Measurements of the Minimum Thickness and Maximum Corrosion Rate for the Entire Tank Bottom Made in Step 10.

Compute the time to the next out-of-service inspection, TNI-α, using the minimum thickness and maximum corrosion rate determined in Step 10. This is accomplished using Tables 8-10.

Activity 6 (Step 12): Determine TNI from TNI-ER and TNI-α, where TNI≤10 Years.

Step 12—Determine TNI from TNI-ER and TNI-α, where TNI≤10 Years.

Determine the time to the next out-of-service API 653 internal inspection (TNI=$\Delta t_{0-N}=t_N t_0$) from the combination of TNI-ER and TNI-α determined as a function of the Survival Probability Age Region and the determination of the maximum corrosion rate, $CR_{max}$, as determined using Tables 8-10. This method recommends that an out-of-service API 653 internal inspection should be performed for Survival Probability Age Region D. This method limits TNI to 10 years or less, but allows TNI to be updated at 10 years by re-applying this method provided that the total time between internal inspections is less than a maximum of 30 years (in accordance with API 653).

5. Procedure

Figure 2:
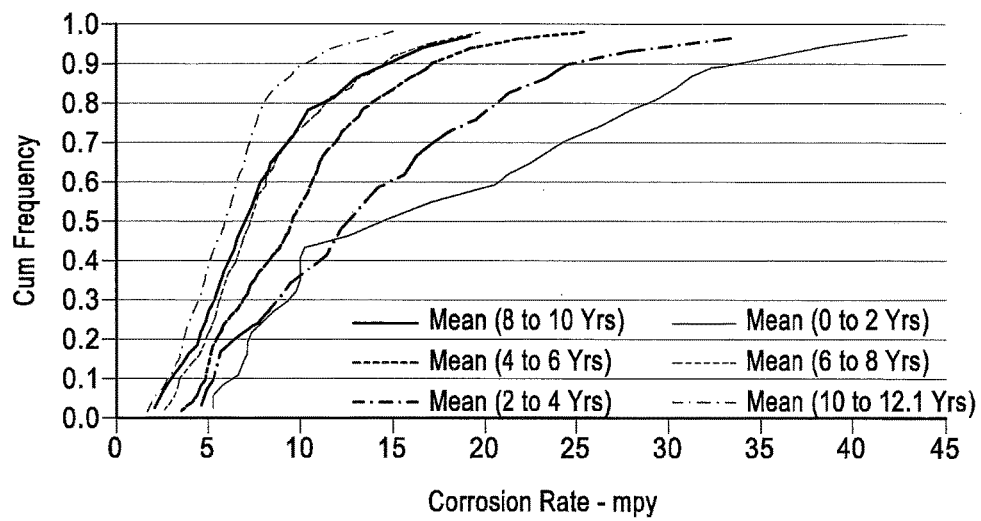
Figure 3:
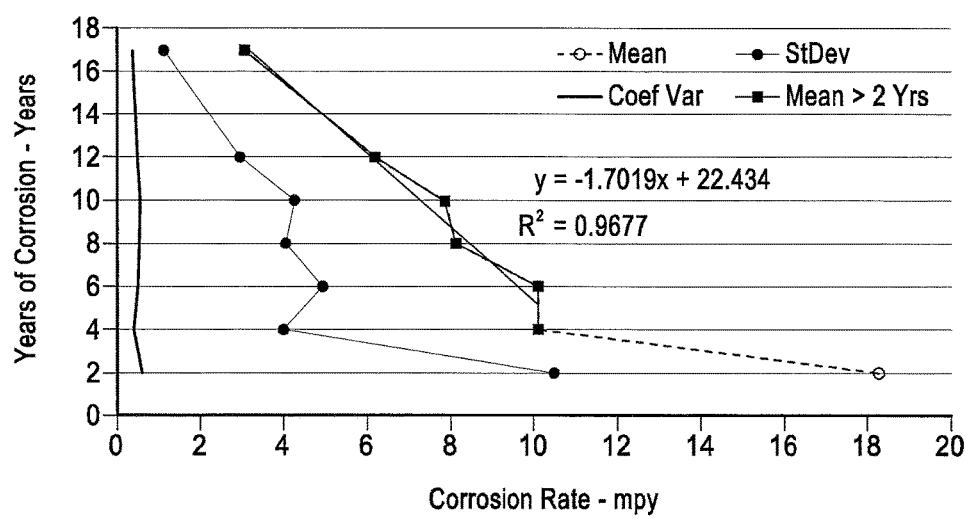

As illustrated in FIGS. 1-3, FIGs. X2.1 and X2.2, and Tables 1 and 3, there are six major activities comprised of 12 steps that shall be considered when using this method. Section 4 presented an overview of these activities and steps. Below, the individual steps to implement this method are described in detail.

There are seven Annexes and fourteen Appendices included in this method. These annexes and appendices are listed in Tables 4 and 5. An Excel Worksheet is provided as part of this method to perform all of the mathematical and statistical calculations, to display the results graphically, and to output the results in a method form. As summarized below and previously in Table 2, Section 4.2, Annex A2, and Appendices 10 and 11, with five straightforward entries, all of the calculations that are required to implement this method are performed and the results are output graphically and on a method form. Annex A1 is a method form that is used for reporting the output of this method, and Annex A2 and Appendices X10-X12 describe how to use the Excel Worksheet attached a tool to this method. Illustrations of the input and output of the Excel worksheet for five cases are presented in Appendix X13. Appendix X2 describes the activities and steps in two flow charts. Annexes A3 and A5-A8 present the mathematical equations used in the Excel worksheet. Annex X4 provides a description of the corrosion data provided as part of this method. Appendix X1 gives the rationale for this method and Appendices X3-X8 and X11 and X13 present illustrations of the output results.

TABLE 4

List of the Annexes supporting the calculations and illustrating the output of this method.

Annexes

| | |
|---|---|
| Annex A1. | Method Form for Reporting the TNI Results of this Method |
| Annex A2. | How to Use the Excel Worksheet to Generate $F_X(x)$, $F_Y(y)$, $S_Y(y)$, $S_Y(y/t_0)$, TNI-ER, TNI-α, and TN |
| Annex A3. | Equations for Generating Weibull CDFs for $F_X(x)$, $F_Y(y)$, $S_Y(y)$, $S_Y(y/t_0)$, and TNI-ER |
| Annex A4. | Description of the Corrosion Data Used to Develop $F_X(x)$ |
| Annex A5. | General Approach for Developing $F_X(x)$ from a CFD of Tank Bottom Corrosion Rates |
| Annex A6. | Mathematical Transformation of $F_Y(y)$ from $F_X(x)$ |
| Annex A7. | Equations for Computing TN-ER from $S_Y(y)$ and $S_Y(y/t_0)$ |

TABLE 5

List of the Appendices supporting the calculations and illustrating the output of this method.

Appendices

| | |
|---|---|
| Appendix X1. | Rationale |
| Appendix X2. | Flow Charts Illustrating the Implementation of the Method |
| Appendix X3. | Illustration of $F_X(x)$ and $f_X(x)$ for a $CR_{max}$ of 6 mpy |
| Appendix X4. | Illustration of $F_Y(y)$ and $f_Y(y)$ for $F_X(x)$ in Appendix X3 |
| Appendix X5. | Illustration of $S_Y(y)$ and $s_Y(y)$ for $F_Y(y)$ and $f_Y(y)$ in Appendix X4 |
| Appendix X6. | Illustration of $S_Y(y)$ and $S_Y(y/t_0)$ for $F_X(x)$ in Appendix X3 Used to Compute TNI-ER |
| Appendix X7. | Illustration of Three Different Weibull CDFs for $F_X(x)$ in Appendix X3 |
| Appendix X8. | Illustration of Survival Age Regions (A, B, C, and D) |
| Appendix X9. | Illustration of TNI-ER for Different Survival Age Regions for $F_X(x)$ in Appendix X3 |
| Appendix X10. | Use of the Excel Worksheet for Developing $F_X(x)$ from a CFD of Tank Bottom Corrosion Rate |
| Appendix X11. | Use of the Excel Worksheet for Developing $F_X(x)$ for the Tank of Interest |
| Appendix X12. | $F_X(x)$'s of the Tank Bottom Corrosion Rates that can be Used to Implement this Method |
| Appendix X13. | Illustration of the 12-Step Method |
| Appendix X14. | Mathematical Symbols |

The figure in the Appendix X3 presents a graphical illustration of the output result of this method for the probability density function, $f_X(x)$, and the cumulative distribution function, $F_X(x)$, for a $CR_{max}$ of 6 mpy; Appendices X4-X6 present graphical illustrations of $F_Y(y)$, $S_Y(y)$, and $S_Y(y/t_0)$ for this $F_X(x)$. Appendix X7 presents graphical illustrations of three different CDFs of $F_X(x)$. Appendices X8 and X9 present graphical illustrations of $F_Y(y)$, $S_Y(y)$, and $S_Y(y/t_0)$ for different survival probability age regions. Appendix X9 presents graphs of $S_Y(y/t_0)$ superimposed on $S_Y(y)$ between $y=t_0$ and $y=t_N$ where $S_Y(y=t_N/t_0)=S_Y(y=t_0)$, which illustrates the determination of TNI-ER using Equivalent Risk for different survival probability age regions. All of the displays in the Annexes and Appendices can be generated with the Excel worksheet described in Annex X2 with Appendices X10-X12 showing how to generate or select $F_X(x)$ to use in the Excel worksheet; example illustrations are presented in Appendix 5.

5.1 Overview of the 12-Step Method

The overall goal of this method is to compute the time to the next out-of-service API 653 internal inspection of the tank bottom ($TNI=t_0-t_N$) from an in-service inspection of the tank bottom of the tank at any time in the service life of a tank. TNI is based on the appropriate combination of two potential determinations of TNI, one in Step 8 (TNI-ER) and one in Step 11 (TNI-α. The first (TNI-ER) is based on Equivalent Risk, which is determined from the survival probability distribution of the tank bottom at $y1=t_0$, $S_Y(y1)$, and the Bayesian update of this survival probability distribution at $y2=t_N$, $S_Y(y2/t_0)$. The second TNI (TNI-α) is based on additional measurements of the minimum thickness and maximum corrosion of the entire tank bottom. This second estimate is not needed to implement this method, but is usually beneficial in terms of a larger TNI for tanks when the survival probabilities are greater than 50% and is particularly meaningful for Survival Probability Age Region A, where y is generally 10 years or less and $S_Y(y)$ is typically greater than 95%. The measurements of TNI-α are justified for high survival probabilities, because most of the out-of-service API 653 internal inspections are performed at high survival probabilities, especially when they are performed at 10-year intervals in the Probability Survival Age Region A, which typically use deterministic measurements of bottom thickness across the entire tank floor like, but more comprehensive than those used to determine TNI-α.

This method is applied individually to each tank being considered for inspection. In-service measurements of the thickness, corrosion rate, and integrity of the tank bottom are required to implement this method. To implement this method, a cumulative distribution function (CDF) of the survival probability of the tank bottom, $S_Y(y)$, needs to be generated from a population of tanks to which the tank of interest belongs, i.e., a population of tanks with statistically the same corrosion and operational characteristics as the tank of interest. Once $S_Y(y)$ is determined for this population of tanks, a Bayesian update, $S_Y(y/t_0)$, can be generated and used to compute TNI-ER.

This method generates $S_Y(y)$ directly from a simple calculation involving the cumulative distribution function (CDF) of the tank failure probability distribution, $F_Y(y)$, $S_Y(y)=1-F_Y(y)$. $F_Y(y)$ is determined from a mathematical transformation of the corrosion rate distribution, $F_X(x)$, to which the tank of interest belongs. The mathematical transformation of $F_X(x)$ to $F_Y(y)$ is described in Annex A6. To facilitate the mathematical computations, $F_X(x)$ is determined by fitting a Weibull CDF distribution to the empirical cumulative frequency distribution (CFD) of corrosion rates used to generate $F_X(x)$. A Weibull distribution was selected, because it is frequently used to accurately and reliably describe failure, survival, and reliability problems similar to the type of problem addressed in this method. This method provides a wide range of CDFs of $F_X(x)$ that can be used to implement this method. The in-service measurements of corrosion rate in Step 3 are used to accurately and reliably select (Annex A4 and Appendix X11) $F_X(x)$ to use when applying this method. Alternatively, Annexes A5 and Appendix X10 provide a method to generate $F_X(x)$ using both the data from [7] and from previous out-of-service API internal inspection reports.

Failure of the tank bottom in this method can be defined in a number of ways. It can be defined when the tank bottom actually fails (e.g., due to a hole or crack in the bottom). For out-of-service API 653 internal inspections, however, failure is defined when the thickness of the tank bottom has corroded to a minimum allowable thickness ($T_{MAT}$) that is defined by API 653 (either 0.05 in. when a release prevention barrier (RPB) is present, or 0.10 in. when a RPB is not present). When $T_{MAT}$ has been reached, maintenance, repair, refurbishment, or replacement of the tank bottom must be considered. This method recommends defining failure of the tank bottom as described by $T_{MAT}$ in API 653. For most ASTs and bulk USTs, which typically have a tank bottom thickness of 0.25 in., $T_{MAT}$ provides a very large built-in factor of safety when generating $F_X(x)$, $F_Y(y)$, $S_Y(y)$, and $S_Y(y/t_0)$ and determining TNI.

This method generates $F_X(x)$ from a comprehensive corrosion database developed by the National Bureau of Standards (NBS) over an 18-year period at 47 locations throughout the United States [7] (see Annex A4) and then uses in-service measurements of the minimum thickness and the maximum corrosion rate of the tank bottom made as part of this method to select or generate the appropriate $F_X(x)$ to generate $F_Y(y)$, $S_Y(y)$, $S_Y(y/t_0)$, and TNI. This method uses the in-service measurement of the uniform corrosion rate of the tank bottom, $CR_{avg}$, to determine the maximum corrosion rate of the tank bottom, $CR_{max}$, based on this 18-year historical database to use in selecting $F_X(x)$. $CR_{max}$ is based on replicate measurements of the maximum pitting depth of the tank bottom. $CR_{max}$ is usually 6 to 8 times greater than $CR_{avg}$, the uniform corrosion rate of the tank bottom. In some cases, $CR_{max}$ is even larger than 6 to 8 times greater than $CR_{avg}$. $F_X(x)$ is then selected or generated based on $CR_{max}$ for a population of tanks with the same corrosion and operational conditions and is then used to generate $F_Y(y)$, $S_Y(y)$, and $S_Y(y/t_0)$.

This method describes three methods to generate $CR_{max}$: (1) use of the empirical corrosion models provided in this method that relates $CR_{max}$ to $CR_{avg}$, (2) use of bottom thickness and corrosion rate measurements made for the entire tank bottom from a previous out-of-service API 653 internal inspection on the tank under consideration and updated using measurements of $CR_{avg}$ (or $CR_{max}$) made as part of the method, and (3) use of the statistical distributions (CDFs) obtained for from at least 50 independent, out-of-service API 653 internal inspection reports that are representative of the corrosion and operational conditions of the tank to be inspected. The first two methods are preferred and allow the most straightforward application of the method. The third method is also viable, but this method requires a significant effort to achieve.

Once $CR_{max}$ is determined for the tank of interest, a distribution, $F_X(x)$, is selected from a database of $F_X(x)$'s as a function of $CR_{max}$ that is provided in this method (see (1) or (2) above) or is calculated as described in Appendix 11. Alternately, $F_X(x)$ can be generated from a large number of previous out-of-service API 653 internal inspections (see (3) above) with the same corrosion and operational characteristics as the tank of interest. Once $F_X(x)$ is obtained, $F_Y(y)$, $S_Y(y)$, and $S_Y(y/t_0)$ can be generated directly by mathematical calculation. This method describes in detail how to generate $F_X(x)$, $F_Y(y)$, $S_Y(y)$, and $S_Y(y/t_0)$ and provides both a mathematical solution (Annexes A3 and A5-A7) and an Excel spreadsheet solution.

There are three ways to define $CR_{max}$. $CR_{max}$ can be determined from (1) the sum of the maximum values of the underside (external) and topside (internal) corrosion rates ($CR_{max} = CR_{max-underside} + CR_{max-topside}$), (2) the maximum value of the corrosion rate made from tank bottom thickness measurements, regardless of whether or not the corrosion is underside or topside corrosion, and (3) the use of a multiplier of 1.4 on the corrosion rate determined in (2) to account for the underside and topside corrosion coinciding as in (1). When an out-of-service API 653 internal inspection is being performed, the first approach is used, even if the maximum external and maximum internal corrosion locations are different. In this method, the most realistic estimate of the minimum thickness and maximum corrosion rate for the tank is used, regardless of whether or not it occurs internally or externally. In most instances, the maximum corrosion rate is due to external or underside corrosion of the tank bottom in direct contact with the backfill or soil beneath the tank bottom. The multiplier in (3) is determined from as described in API653.

The $CR_{max}$ provided in this method was developed from the CFDs of the maximum pitting external corrosion rates, $CR_{max}$-underside, obtained from 8 replicate samples at 5 specific times after installation in an 18-year study at 47 locations throughout the continental US as a function of the underlying uniform corrosion rates [7]. The corrosion rate data used in this method was obtained in the time interval between 9.6 and 12.1 years (approximately 10 years) after the samples were initially buried. The study showed that the probability distribution of $CR_{max}$, $F_X(x)$, due to maximum pitting is Weibull distributed and that the mean $CR_{max}$ is typically at least 6 to 8 times higher than the mean uniform corrosion rate, $CR_{uniform} = CR_{avg}$.

13.1 12-Step Method

A detailed description of the 6-activity, 12 step method, which is summarized in Table 3 (and FIG. X2.2), is described in detail below. It should be noted that this 12-step method can be briefly summarized and implemented very efficiently if this method is followed using the Excel worksheet provided with this method. The use of the Excel worksheet is described in Annex A2 and Appendices X10 and X11 and its use is illustrated in Appendix X13. The tank owner/operator can compute TNI-ER using the Excel spreadsheet once the tank passes a leak detection integrity test and makes eight to ten tank bottom measurements of corrosion at one location in the tank. TNI-α can contribute to the calculation of TNI if (1) the survival probability is greater than 50% (Survival Probability Age Regions A and B) and (2) either an AECAT test is performed and/or a previous out-of-service API 653 internal inspection exists, where the results of an AECAT test performed in Step 10 show no or minimal corrosion activity and/or $T_{min}$ and $CR_{max}$ computed in this previous API 653 internal inspection is adjusted by the ratio of the corrosion rates measured as part of this method in Step 3 at the same approximate location in the previous API 653 internal inspection are entered into the Excel worksheet. The Excel worksheet will help generate the corrosion rate probability distribution $F_X(x)$ for the tank of interest, compute TNI, TNI-ER, and TNI-α for this tank, output graphs of the probability distributions $F_X(x)$, $F_Y(y)$, and $S_Y(y)$, and output a graph of $S_Y(y)$ and $S_Y(y/t_0)$ between $y1=t_0$ and $y2=t_N$. This summary assumes that all of the measurements are made within industry accepted standards as described in this method.

Activity 1 (Step 1): Does the Tank Owner/Operator want to Apply this Method?

Step 1—Determine Whether or not the Tank Owner/Operator Wants to Use this Method, and if so, What Benefit (or Benefits) does the Tank Owner/Operator Receive by Applying this Method?

The objective of Step 1 is to determine whether or not there is a need or benefit for applying this method. This method can be used to (1) check, and/or (2) update the time to the next out-of-service API 653 internal inspection, TNI, at any time in the service life of a tank. This method identifies two types of important potential applications (see Section 2.7) that were described and discussed in more detail in Section 4.

It should be noted that this method allows the tank operator/owner to perform an out-of-service API 653 internal inspection at any time regardless of the magnitude of TNI. Also, if the tank owner/operator decides not to apply this method and the tank is scheduled for an out-of-service API 653 internal inspection, then this method recommends that such an inspection be performed.

This method can be considered for use if:
(1) The tank is a field erected AST or a bulk UST with vertical walls and a flat bottom containing petroleum or water products that would require an out-of-service internal inspection;
(2) One of the general needs or requirements in Sections 2.7 is being addressed;
(3) The maximum time interval stated in API 653, since the last out-of-service internal inspection is not exceeded (currently 30 years in API 653);
(4) The internal inspection is controlled by the corrosion of the bottom or floor of the tank, rather than being controlled by other parts of the tank like the roof, the shell, or internal appurtenances.

Items (1) Through (3) can be Addressed Easily. Item (4) is Addressed in Steps 2 and 3.

Activity 2 (Steps 2 and 3): In-Service Measurements of Corrosion to Determine if this Method can be Used?

Step 2—Conduct a Leak Detection Integrity Test to Determine Whether or not the Tank of Interest has Survived to $t_0$.

The overall objective of Steps 2 and 3 is to determine whether or not the tank meets the minimum requirements for application of this method. Steps 2 and 3 can be performed in any order, but the requirements in both steps need to be met to apply this method. Operational, environmental, and cost impacts are valid reasons for determining which step is implemented first.

The objective of Step 2 is to determine whether or not the tank of interest has survived to $t_0$. If the tank has survived to $t_0$, then the Bayesian update, $S_Y(y/t_0)$, of the underlying survival probability CDF, $S_Y(y)$, can be generated and used to compute TNI-ER.

A Leak Detection Integrity Test (also called a Precision Tank Test, a Tank Tightness Test, or a Tank Integrity Test) is conducted to determine whether or not the tank has survived. The test can be performed with an in-tank or an ex-tank leak detection system provided that it meets the criteria specified in this method. Survival is determined by whether or not the tank has integrity, i.e., whether or not it is leaking, and survival is assessed in this method by whether or not the tank PASSes the leak detection integrity test. Step 2 requires the conduct of a leak detection test with a test method for a single-bottom or a double-bottom AST or bulk UST in accordance with the apparatus, calibration, personnel, and test method performance criteria in Sections 6, 7, 8, and 10 of this method. For single-bottom tanks, the tank shall PASS a test with a Leak Detection Integrity Test using a test method that has been evaluated for performance by an independent, nationally recognized, third-party. Any method (1) listed by or (2) evaluated in accordance with (1) the NWGLDE or (2) a national recognized method qualifies. For double-bottom tanks, the tank shall PASS a test with a Leak Detection Integrity Test using a test method that (1) meets the method for a single-bottom tank or (2) has been evaluated by or used by a SME or PE in accordance with industry practice or nationally recognized standards. If the tank FAILs (i.e., does not PASS) a leak detection test, this method recommends, after checking and verifying the leak detection result, that the tank should be taken out-of-service and internally inspected following API 653. If the test result is an INCONCLUSIVE, then the evaluation or manufacturer's method for re-testing should be followed, which usually means performing another leak detection test with the same or different method.

If the tank PASSes a leak detection test, it meets the first criteria to be a candidate for application of this method, because the tank bottom still has life remaining. However, until further measurements of the tank bottom thickness and corrosion rate are made, it is not known how much life remains. Passing a leak detection test provides up to a {1-year} period to make this assessment unless the $T_{avg}$ or $T_{min}$ due to pitting made in Step 3 is less than $T_{MAT}$. If $T_{avg}$ or $L_{min}$ are less $T_{MAT}$, then this method recommends that an out-of-service API 653 internal inspection be performed.

The sole purpose of the leak detection integrity test is to determine whether or not the tank has survived to its present age and has remaining life. How much life remaining will depend on the bottom thickness and the corrosion rate measurements made in Step 3 (and/or Step 10).

Step 3—Measure the Thickness ($T_{meas}$) and the Corrosion Rate ($CR_{Meas}$) of the Tank Bottom at One or More Locations and Determine the Maximum Corrosion Rate ($CR_{max}$) to Use in Generating $F_X(x)$.

The objective of Step 3 is to measure the mean (or median) tank bottom thickness at one or more locations in the tank and to use the smallest mean (or median) thickness from any of the measurement locations, $T_{avg}$, in determining the mean (or median) corrosion rate, $CR_{avg}$. $CR_{avg}$ is then used to determine the maximum corrosion rate, $CR_{max}$, which is used in selecting or generating the corrosion rate distribution, $F_X(x)$, to which the tank belongs. $CR_{max}$ can be determined from $CR_{avg}$ using the empirical relationship ($CR_{ratio \{uniform\ to\ pitting\}}$) provided in this method that relates the maximum corrosion rate in a tank (due to pitting) to the uniform corrosion rate in a tank. This method assumes that $CR_{avg}$ is representative of the uniform corrosion rate of the entire tank bottom, $CR_{uniform}$. This assumption is very reasonable and is verified as part of the method. This method provides three empirical methods, which are described below, for determining $CR_{max}$ from the measured $CR_{uniform}$.

This method provides an empirical relationship relating $CR_{max}$ and $CR_{uniform}$ in Annex A4 ($CR_{ratio \{uniform\ to\ pitting\}}$) for each corrosion rate, x, in the $F_X(x)$, where $F_X(x)$ was generated as a function of the age of the tank and the geographical region (climate and soil conditions). A similar empirical relationship can be generated if $F_X(x)$ was generated from previous out-of-service API 653 internal inspection reports for a group of tanks with the same corrosion and operational conditions. If a previous out-of-service API 653 internal inspection report exists (Step 10), this empirical relationship can also be generated directly from this report by taking the ratio of $CR_{avg}$ measured in Step 3 and in the previous API 653 report and multiply it by the $CR_{max}$ determined in the previous API 653 report. Finally, $CR_{max}$ can be determined by multiplying $CR_{max}$ determined by $CR_{ratio}$ above by 1.4 to account for topside or internal corrosion of the tank bottom.

The in-service measurement of the mean (or median) bottom thickness, $T_{avg}$, and the average corrosion rate, $CR_{avg}$, have three purposes. First, as stated above, they are used to generate $F_X(x)$ and then $F_Y(y)$, $S_Y(y)$, and $S_Y(y/t_0)$ for use in determining TNI-ER. Second, they are used as a first check to determine if the tank bottom has sufficient thickness to allow the use of this method. Third, they are used as part of the method for determining the thickness and corrosion rate for the entire tank bottom when additional measurements of the tank bottom are available from an AECAT test result and/or a previous API 653 internal inspection report.

The tank bottom thickness measurements, $T_{i,j}$, where i=1, 2, ..., n are locations, and j=1, 2, ..., 8, ..., N are the number of sensor thickness measurements made at each location, should be with a sensor system with a precision and bias of at least 0.010 in., respectively. The measurements can be made at any convenient tank opening and shall be made on the tank bottom and not on a strike plate or other protective plate covering the bottom. The mean, median, minimum, maximum, and method deviation should be determined from a minimum of eight, and preferably 10 independent, bottom thickness measurements made at each location. Replicate thickness measurements should be made, where the replicates are non-overlapping so that measurement independence can be maintained. Small location differences of 1 to 6 in., or more, are recommended. This method recommends a square or rectangular sampling pattern with two measurements made in the center of the square or rectangle and with two measurements made at each corner of the square or rectangle. If an in-tank thickness sensor is used, it should be lifted from or near the bottom and placed back on or near the bottom for each measurement. If the measured mean (or median) thickness, $T_{avg}$, is greater than the minimum allowable thickness, $T_{MAT}$ (0.10 in. for a tank with a release prevention barrier (RPB) or 0.050 in. for a tank without a RPB), then the tank meets the first criterion for application of this method. If not, this method should not be applied and an out-of-service API 653 internal inspection is recommended by this method.

The measurements of bottom thickness, $T_{i,j}$, are made at time $t_0$ to determine the mean (or median) bottom thickness, $T_{avg\ at\ t0}$, at $t_0$. The mean (or median) corrosion rate, $CR_{avg}$, is determined from the change in the mean (or median) thickness since the last time, $t_P$, that measurement of bottom thickness was measured at approximately the same location in the tank. The mean (or median) corrosion rate, $CR_{avg}$, is determined using Eq. (5.1).

$$CR_{avg} = <CR_{avg\ at\ t0}> [(T_{avg\ at\ t0} - T_{avg\ at\ tP})]/[t_0 - t_P] \tag{5.1}$$

where $t_P$ was either the point in time when the tank was initially installed or when the tank was last taken out-of-service for an API 653 internal inspection. The measurement of thickness, $T_{avg\ at\ tP}$, may be comprised of only one measurement, because the thickness at $t_P$ measured while the tank was out-of-service is considered highly reliable in comparison to an in-service measurement made with fuel in the tank.

As stated above, if bottom thickness measurements are made at multiple locations, i.e., the location with the smallest mean (or median) thickness, $T_{min}$, should be used to obtain the maximum corrosion rate, $CR_{max}$.

In most instances, measurements of $t_{i,j}$ that are made to determine $T_{avg}$ and $CR_{avg}$ will be determined at only one location, i=1, and will be comprised of j≥8 independent measurements. The replicate thickness measurements made at each location should be checked to assess whether or not the thickness measurements are produced by uniform corrosion over time or whether or not one or more of the thickness measurements are produced by non-uniform (i.e., higher) corrosion activity. Analysis of UT thickness measurements in out-of-service API 653 internal inspection reports indicate that if the bottom is subject to only uniform corrosion activity, then each pair of replicate measurements and all of the thickness measurements of $T_{i,j}$ should be within three method deviations, S, of the mean thickness, $T_{avg}$.

At each bottom thickness measurement location, i, two measurement checks will be made. The first check is to determine the validity of each of the thickness measurements, and the second check is to determine if uniform corrosion exists or is the location is a region of local pitting or higher corrosion activity. Both checks are done by comparing each of the individual thickness measurements to the mean (or median) thickness measured at each location, i, to determine whether or not they are within {±5} method deviations of the mean (or median).

Two checks are made at each location. First, the replicate measurements at each location, I, should be compared to determine if measurements were appropriately sampled. The measurements are valid if the absolute value of the difference in the two measurements is less than $(3*S_{i,j})$. If this test fails, a second replicate set of measurements should be made. Second, at each location, i, the $abs[(T_{i,j}-T_{avg})]$ is computed for j=1 to N and is compared to $(5*S_{i,j})$; if $abs[(T_{i,j}-T_{avg})]>(5*S_{i,j})$, then the check fails. If the check fails for the first N thickness measurements, it is assumed that one (or more) of the thickness measurements was improperly made. If it fails a second time after repeating the N thickness measurements, then $T_{avg}$ should not be assumed to be equal to $T_{uniform}$ and should not be used to compute $CR_{max}$. If this check is failed twice, a second location for the measurement should be made to determine $T_{uniform}$ and $CR_{max}$. In the unlikely event that the $CR_{max}$ determined from $T_{uniform}$ is less than the $CR_{max}$ determined using the minimum thickness, $T_{min\ i,j}$, then $T_{avg}$ used in Step 3 to compare to $T_{MAT}$ should be $T_{min\ i,j}$ and $T_{min\ i,j}$ should be used to determine $CR_{max}$. {This also applies to Steps 10 and 11 if additional tank bottom thickness measurements across the entire tank bottom are used to estimate TNI-α.}

If thickness measurements do not fail the check at location i=1, but the $CR_{avg}$ determined from $T_{uniform}$ is {2} mpy or greater, it is highly probable that the $T_{avg}$ computed at the first location does not actually represent the underlying uniform corrosion rate and probably is indicative of a region of higher corrosion due to a region of pitting or excess thinning of the tank bottom. If this occurs, then it is highly recommended that the mean (or median) thickness be determined by a second set of measurements at another location on the tank bottom. If this second set of measurements is less than {2} mpy, then the corrosion rate determined from this second location should be used to determine $F_X(x)$, $F_Y(y)$, $S_Y(y)$, and $S_Y(y/t_0)$. The use of the second location for obtaining $T_{avg}$ and $CR_{avg}$ is used, because the empirical relationship used to compute $T_{min}$ and $CR_{max}$ is based on uniform corrosion.

This method shall use a bottom thickness measurement sensor that has a precision and bias of 0.010 in., or better, after averaging (or taking the median) of 8 to 10 measurements, or more.

In summary, Step 3 requires

Use of a sensor system that will measure the thickness of the bottom steel plate to within 0.010 in.;

Collection of 8 to 10 (4 to 5 replicate samples) independent thickness measurements of the tank bottom by moving the probe and making at least four non-overlapping measurements at one or more locations;

Calculation of the mean, median, method deviation, minimum, and maximum at each location;

Comparison of the replicate pairs of thickness measurements if $CR_{avg}$≤{2} mpy to determine if the difference is less than $3*S_{i,j}$; if not repeat measurement at that location. If $CR_{avg}$>{2} ropy, or if the second set of measurements does not pass the criterion, change locations and repeat the measurements.

Comparison of the individual thickness measurements to the mean (or median) if $CR_{avg}$≤{2} mpy to determine if the difference is less than $5*S_{i,j}$; if not repeat measurements at that location. If $CR_{avg}$>{2} mpy, or if the second set of measurements do not pass the criterion, change locations and repeat the measurements.

Computation of $CR_{max}$ from $T_{uniform}$ as indicated in Step 3b, where $T_{uniform}$ is determined from the location where $T_{avg}$ is the smallest.

Use of $CR_{avg}$ in Step 3b as indicated in Step 3b to determine $CR_{max}$ to use in selecting $F_X(x)$.

Step 3b—Determine the Maximum Corrosion Rate ($CR_{max}$) from $CR_{avg}$ to Use in Generating $F_X(x)$.

The next step is to make an estimate of the maximum corrosion rate due to pitting and thinning of the tank bottom, $CR_{max}$, from the uniform corrosion rate, $CR_{uniform}=CR_{avg}$, measured in Step 3a. Three methods are provided to generate $CR_{max}$ from $CR_{uniform}$ as listed below. These Methods are also used to compute $F_X(x)$ in Step 4.

Method 1.

Use of historical corrosion data in [7] that is provided by this method and provides a relationship ($CR_{ratio\ \{max\ pitting\ to\ uniform\}}$) between the mean uniform corrosion, $CR_{uniform}$ and the maximum corrosion rate, $CR_{max}$, due to pitting/thinning of the tank bottom as a function of the age of the tank, $t_0$, and the geographical, climate, and soil conditions: $CR_{ratio\ \{max\ pitting\ to\ uniform\}}=CR_{max\ pitting}/CR_{uniform}$). Thus, $CR_{max\ pitting}$ can be determined from a measurement of $CR_{uniform}$. $CR_{max}$ is then determined from $CR_{max}=CR_{ratio\ \{max\ pitting\ to\ uniform\}}*CR_{uniform}$.

Method 2.

Use of the mean uniform corrosion rate and the maximum underside and topside corrosion rates measured in a previous API 653 internal inspection report and updated by the ratio of the mean uniform corrosion rate measurements made as part of this method in Step 3 and the mean corrosion rate measured in the previous API 653 internal inspection report. Thus, $CR_{max}=CR_{max\ tP\ (prev\ API653)}*(CR_{avg\ at\ t0}/CR_{avg\ tP\ (prev\ API653)})$ Method 3.

Use of historical corrosion data generated as part of this method of the bottom thickness measurements from 50 or more out-of-service API 653 internal inspection reports for the same corrosion and operational environments. Method 1 and 3 are identical except for the use of different corrosion data sets to computed $CR_{ratio\ \{max\ pitting\ to\ uniform\}}$, $CR_{max\ pitting}$, and $CR_{uniform}$.

Method 1.

FIG. X12.1 and Table X12.2 provide the mean corrosion rate ratio of the measured maximum pitting on the replicate samples to the measured uniform corrosion rate, $CR_{ratio\ \{max\ pitting\ to\ uniform\}}$ developed from the 18-year corrosion study used in this method [7]. The mean was calculated from 20% to 90% of the corrosion rate CDFs to minimize the extreme value effects of the tails of the distribution and to best represent all of the data in each group. The median value for all of the data is also provided and is in close agreement to the mean. The mean $CR_{ratio}$ for the CDFs from 0 to 4 mpy, 4 to 8 mpy, and 8 to 12 mpy is 5.1, 8.4, and 6.1, respectively. The highest values were for the middle range of the corrosion rates (4 to 8 mpy), which is probably due to a larger number of samples in this group.

This study measured the uniform corrosion rate, $CR_{uniform}$, the corrosion rate due to the maximum pit penetration depth, $CR_{max\ pitting}$, and the ratio, $CR_{ratio\ (max\ pitting\ to\ uniform)}$, of the maximum pitting penetration (measured with a calipers) to the uniform corrosion (measured by weight) on the same buried sample using the average of replicate samples collected for 4 different steel alloys and two different sample sizes as a function of geographical location (47 locations throughout the United States) as a function of burial time (at six different time periods over an 18-year period). Table X12.2 was generated from the Weibull CDF fit to the empirically generated CFDs of the maximum corrosion rate data used to generate three $F_X(x)$s in Step 4 obtained 9.6 to 12.1 years after burial after partitioning the data by subgroups of the mean maximum corrosion rate (0 to 4 mpy, 4 to 8 mpy, and 8 to 12 mpy). The maximum corrosion rate was determined from the 16 samples at each location. Table X12.3 presents the parameters of the three Weibull distributions for $F_X(x)$ that were generated for these three subgroups and the parameters of the Weibull distributions that were used to define the $F_X(x)$ nearest each nearest to each of these three distributions to the nearest 1 mpy.

$CR_{max}$ can be determined by using the maximum measured $CR_{max\ pitting}$ that is determined from the mean $CR_{uniform}$. For this data set, $CR_{max\ pitting}$, and, therefore, $CR_{max}$, is representative of the underside (or external) corrosion, which is typically the location of the largest corrosion rates measured for tank bottoms. It is possible for some tanks that the topside corrosion may be larger than the underside, but our analyses indicates that it is unlikely that it is any larger than the value of $CR_{max\ pitting}$ determined using this data set.

In API 653, a formula is used for estimating the corrosion rate in the tank bottom when using RBI methods when no corrosion rate information is available. The base underside/external corrosion rate in this formula is given in API 653 is 5 mpy and the base topside/internal corrosion rate in Eq. ({1}) is 2 mpy. This formula recognizes and indicates that the underside corrosion is typically significantly larger than the topside corrosion. This formula suggests, on average, that the underside corrosion is 1.4 (i.e., 7/5) times larger than the topside corrosion (7/5=(5+2)/5=1.40).

If the tank owner/operator wants to be extremely conservative or wants to be consistent with how the maximum corrosion rate is usually determined from tank bottom thickness measurements during an out-of-service API 653 internal inspection, $CR_{max}$ can be determined by summing the maximum underside and topside corrosion rates. This is very conservative, because it assumes that the locations of the maximum internal and external corrosion overlap. If this latter approach is taken, then $CR_{max}$ determined using the dataset provided by this method needs to be increased to account for the topside/internal corrosion. The average values of the ratio of the underside and topside corrosion rates in Eq. (1) are used to account for the topside corrosion in this method by multiplying the measurement of $CR_{max\ pitting}$ by 1.4 (7/5=(5+2)/5=1.40). When determining $F_X(x)$ and when determining $F_Y(y)$, $S_Y(y)$, and $S_Y(y/t_0)$ from $F_X(x)$, this method recommends using only the maximum pitting depth (i.e., a multiplier of 1.0 and not 1.4), because this is a realistic and conservative estimate of the maximum corrosion rate expected.

This approach (of using 1.0 as the multiplier) is highly conservative, because the method used to generate $CRatio_{max\ pitting\ to\ uniform}$ from $CR_{max\ pitting}$ and $CR_{uniform}$ measured in the study used a weight-based method of determining the uniform corrosion rate, $CR_{uniform}$, versus the less accurate operational thickness measurement methods used to make a measurement of $CR_{uniform}$. $CRatio_{max\ pitting\ to\ uniform}$ is at least a factor of 2 to 3 greater than it would be if "thickness measurements" versus "weight measurements" were used in measuring $CR_{uniform}$ in the study. Also, the large number of diverse locations used in this study allows for the possibility of extreme values of pitting to occur.

Method 2:

If a previous out-of-service API 653 internal inspection exists with the maximum underside and topside corrosion rate and the bottom thickness measurements in the proximity of the bottom thickness measurements made in Step 3 as part of this method, then Method 2 can be applied. $CR_{max}$ is determined by multiplying the maximum corrosion rate determined in the previous out-of-service API 653 Internal Inspection, $CR_{max\ tP\ (prev\ API653)}$ and the ratio of $CR_{Avg}$ measured as part of this method and the measurement of $CR_{avgtP\ (prev\ API653)}$ at the previous out-of-service API 653 Internal Inspection before any maintenance or repairs of the tank bottom were made.

$$CR_{max}=CR_{max\ tp(prev\ API653)}*(CR_{Avg}/CR_{avg\ tp(prev\ API653)}) \quad (5.2)$$

$CR_{max}$ determined in Eq. ({5.2}) is then used to generate $F_X(x)$, $F_Y(y)$, $S_Y(y)$, and $S_Y(y/t_0)$ in Step 4. $CR_{max}$ determined in Eq. ({5.2}) by determining $CR_{max\ tp\ (prev\ API653)}$ by summing the maximum internal and external corrosion if the locations of the maximum internal and external corrosion overlap, or if the tank owner wants to be highly conservative. Regardless of which method is used to generate $CR_{max}$, the resulting $CR_{max}$ (either underside only or the sum of the underside and topside) should be very conservative, because the sources of the highest regions of corrosion should have been eliminated as part of the maintenance and repair activities during that previous API 653 internal inspection.

There will be differences in the CDFs generated for $F_X(x)$, $F_Y(y)$, and $S_Y(y)$ using the corrosion data in Method 1 and the corrosion data results in Method 2, because the CDFs generated in Method 1 represent a wide range of corrosion data throughout the United States and the CDFs generated in Method 2 will represent the corrosion data for the specific tank of interest.

Method 3:

Method 3 can be implemented using a similar approach to Method 1 by developing $CR_{max}$ and $F_X(x)$ from a large enough sample of previous out-of-service API 653 internal inspection reports that were obtained with the same corrosion and operational conditions. This method recommends that a minimum of 50 API 653 reports shall be used. To be independent, only one API 653 inspection report for each tank shall be used. If more than one API 653 report exists, the most recent one should be used, but comparison of previous reports should be performed to ensure that the corrosion between API 653 inspections is consistent and does not prohibit the use of this option.

As in Method 1, a decision must be made on whether or not to use the maximum underside corrosion rate alone or to sum the maximum underside and topside corrosion rates. If the "sum" is used, Method 3 directly provides this information. In Method 1, a multiplier of 1.4 is used to include the "sum." Our analyses in preparing this method suggests that the maximum underside and topside corrosion should be summed when using Method 3, but not when using Method 1, because the uniform corrosion rate determined using a thickness sensor (Method 3) versus a weight-based method (Method 1) tends to overestimate $CR_{uniform}$ and therefore, underestimates $CR_{max}$.

There will be differences in the CDFs generated for $F_X(x)$, $F_Y(y)$, and $S_Y(y)$ using the corrosion data in Method 1 and the corrosion data results in Method 3, because the CDFs generated in Method 1 represent a wider range of corrosion data throughout the United States and the CDFs generated in Method 3 will typically represent more localized corrosion data for the specific tank of interest in a more local geographical area.

Summary.

The first two methods for computing $CR_{max}$ are preferred, because they allow the most straightforward and least expensive application of this method. Method 3 can be used, but will typically require generation of $F_X(x)$ for each tank of interest.

Activity 3 (Step 4): Determine $F_X(x)$

Step 4—Generate a Corrosion Rate Distribution, $F_X(x)$, of the Tank Bottom for the Tank of Interest Based on a Population of Tanks Operating in the Same Corrosion and Operational Environments.

A CDF of the corrosion rates, $F_X(x)$, is selected or generated for a population of tanks that operate in the same corrosion and operational environment as the tank of interest. This method provides two methods for generating $F_X(x)$: (A) Use of $F_X(x)$ as a function of $CR_{max}$ developed from 18 years of corrosion data provided by this method, and (B) Use of $F_X(x)$ developed from a minimum of 50 independent, previous out-of-service API 653 internal inspections obtained where the tank experiences the same corrosion and operational conditions. This method recommends using Method A, because it is easier to implement, accurate, and conservative.

The Excel worksheet provided with this method provides the mathematical tools for performing a trial and error curve fit to the corrosion rate data used in this method and tabulated in Table X12.1 or corrosion rate data from the appropriate 50 out-of-service API 653 internal inspection reports. Appendix X10 illustrates such a curve fit for a $CR_{max}=6$ mpy. A minimum of 50 independent corrosion samples comprising the corrosion and operational conditions that would be experienced by the tank of interest is needed to generate $F_X(x)$ for both Methods A and B above. For both methods a least squares fit of a Weibull CDF with an empirically derived CFD of the corrosion data is used to develop $F_X(x)$. A trial and error fit is used to minimize the errors in corrosion rate, x, and in probability of occurrence, $F_X(x)$, where any error less than or equal to ±0.5 mpy in x and less than or equal to ±0.05=±5% in $F_X(x)$ will suffice. It is important to note that the least squares fit with the minimum error in x and $F_X(x)$ might not be the best or most useful fit, because the upper and lower tails of the distribution, which have the least impact on the determination of TNI and which contain the least amount of data, might bias the error. In this method, the fit is weighted towards the central and higher corrosion probabilities.

Any of the methods used to generate $CR_{max}$ in Step 3b can be used to select or generate $F_X(x)$ using either Methods A or B in this step. Once $F_X(x)$ is selected or generated the CDFs of $F_Y(y)$ in Step 5, $S_Y(y)$ in Step 6, and $S_Y(y/t_0)$ in Step 7 are computed mathematically and are then used to mathematically compute TNI-ER in Step 8 from $S_Y(y)$ evaluated at $y=t_0$ and $S_Y(y/t_0)$ evaluated at $y=t_N$ where $S_Y(y=t_N/t_0)=S_Y(y=t_0)$. This method provides (a) mathematical expressions for $F_X(x)$, $F_Y(y)$, $S_Y(y)$, and $S_Y(y/t_0)$ in Annexes A.3, A.5-A.7, and (b) an Excel worksheet that performs the calculations and outputs graphical displays of these functions and the results. This method recommends that tank failure and tank survival be determined using the Minimum Allowable Thickness, $T_{MAT}$, to define corrosion rate and tank age, where $T_{MAT}=0.05$ in. for a tank with a RPB and $T_{MAT}=0.10$ in. for a tank without an RPB (in accordance with API 653).

As illustrated in Appendix X3, the CFD of the corrosion rate data, $F_X(x)$, is extreme-valued. While a number of extreme-valued CDF distributions could be used to describe the corrosion rate data, this method uses a Weibull CDF probability distribution to fit the corrosion rate data. This Weibull probability distribution is then transformed, as described in Step 5 and Annex A6 to generate $F_Y(y)$. A Weibull distribution is historically used to describe failure, survival, and reliability problems like this one. Three-parameter Weibull distributions are generated from least squares fits of the empirically derive cumulative frequency distributions, CFDs, of corrosion rates over a wide range of corrosion conditions. (Note: A normal probability distribution, which is typically used to describe many populations, does not fit the corrosion rate data well and is not used to generate $F_X(x)$. Even if were used, when $F_X(x)$ is transformed to generate $F_Y(y)$, the result would still be an extreme-valued function.)

Method A: $F_X(x)$ Provided by this Method Based on Historical Corrosion Data.

Once $CR_{max}$ is determined for the tank in Step 3b, a CDF probability distribution, $F_X(x)$, is selected or generated from a database of $F_X(x)$'s provided by this method as a function of the mean (or median) $CR_{max}$ (see (1) above) and is summarized in Tables X12.2 and X12.3. Alternatively, $F_X(x)$ can be generated from a large number of previous out-of-service API 653 internal inspections (see (3) above) that are generated in the same way as the $F_X(x)$ provided in this method. Once $F_X(x)$ is obtained, $F_Y(y)$, $S_Y(y)$, and $S_Y(y/t_0)$ can be generated directly by mathematical manipulations. This method describes in detail how to generate $F_X(x)$, $F_Y(y)$, $S_Y(y)$, and $S_Y(y/t_0)$ and provides a mathematical solution and an Excel spreadsheet solution.

Table X12.3 provides $F_X(x)$ for tank bottoms with a maximum corrosion rate between 2 and 18 mpy in terms of the three parameters $\gamma$, $\beta$, and $\eta$ defining the appropriate Weibull distribution meeting the least squares error of $\leq \pm 0.5$ mpy in x and $\leq \pm 0.05$ in $F_X(x)$. FIG. X3.1 in Appendix X3 illustrates $F_X(x)$ for a $CR_{max}$ of 6 mpy. Appendices X4 and X5 present illustrations of $F_Y(y)$, $S_Y(y)$, and $S_Y(y/t_0)$ for this $F_X(x)$. Appendix X6 presents a figure of $S_Y(y/t_0)$ superimposed on $S_Y(y)$ between $y=t_0$ and $y=t_N$, where $S_Y(y=t_N/t_0)=S_Y(y=t_0)$, to illustrate the determination of TNI-ER using Equivalent Risk. The attached Excel spreadsheet can be used to compute $F_X(x)$ for the range of maximum corrosion rates between 2 and 18 mpy in 1 mpy increments by inputting the three parameters of the Weibull distribution summarized in Table X12.3. For different corrosion rates than in table, $F_X(x)$ can be generated as described in Appendix 12 using the closest set of values in Table X12.3 as a start.

$CR_{max}$ provided in this method was developed from the CFDs of the maximum corrosion rates, $CR_{max-external}$, using Method 1 in Step 3b. Method 1 determined $CR_{max}$ from the maximum underside/external pitting depth obtained at 47 locations throughout the continental United States 9.6 to 12.1 years after sample burial. The $F_X(x)$s were calculated for this time interval, because this is the minimum time required to perform an out-of-service API 653 internal inspection and would represent the most conservative determination of TNI-ER for the tank of interest. If the tank owner/operator wanted to be more conservative, they could use the sum of the internal and external corrosion to compute $CR_{max}$ by multiplying the corrosion rate determined in this study by 1.4.

$F_X(x)$ Generated from Previous Out-of-Service API 653 Internal Inspections for Tanks Operating in the Same Corrosion and Operational Environment.

The corrosion rate data used to generate $CR_{max}$ in Step 3b from previous out-of-service API 653 internal inspection reports can also be used to generate, $F_X(x)$. Table 6 should be used and filled out when generating $F_X(x)$ from these previous out-of-service API 653 internal inspection reports. It tabulates $CR_{mean}$, $CR_{max}$, and the ratio $CR_{max}/CR_{mean}$ shall be tabulated for each tank for (1) internal corrosion, (2) external corrosion, and (3) total corrosion and used to generate a Weibull CDF of $F_X(x)$ for a mean or median $CR_{max}$. $CR_{avg}$ is equal to the uniform corrosion rate of the tank bottom, $CR_{mean\ uniform}$, and $CR_{max}$ is equal to the maximum pitting or thinning at any location on the tank bottom. A Weibull CDF of $F_X(x)$ shall be generated for the total corrosion rate by summing the underside/external and the topside/internal corrosion rate in accordance with API 653. Appendix X10 describes the trial and error method used to perform the curve fitting and provides several illustrations of how to perform the curve fitting. Table 7 summarized the curve fits for $F_X(x)$.

TABLE 6

Summary of the Corrosion Data from the Out-of-Service API 653 Internal Inspection Reports used to Generate $F_X(x)$ for a Population of Tanks Operating in the Same Corrosion Environment as the Tank Being Evaluated

| Number | $CR_{mean-uniform}$ (mpy) | $CR_{max-int}$ (mpy) | $CR_{max\ ext}$ (mpy) | $CR_{max-sum}$ (mpy) | $CR_{max\ int}/CR_{mean-unif}$ (mpy/mpy) | $CR_{max\ ext}/CR_{mean-unif}$ (mpy/mpy) | $CR_{max\ sum}/CR_{mean-unif}$ (mpy/mpy) |
|---|---|---|---|---|---|---|---|
| 1 | | | | | | | |
| 2 | | | | | | | |
| 3 | | | | | | | |
| . | | | | | | | |
| . | | | | | | | |
| . | | | | | | | |
| N ≥ 50 | | | | | | | |

TABLE 7

Summary of the Weibull CDF of the Maximum Internal, External, and Total Corrosion Rates, $F_X(x)$, developed from Previous Out-of-Service API 653 Internal Inspection Reports for a Population of Tanks Operating in the Same Corrosion Environment as the Tank Being Evaluated

| Type of CR | Median $CR_{max}$ (mpy) | Mode or Peak $CR_{max}$ (mpy) | StDev of $CR_{max}$ (mpy) | COV | $\gamma$ | $\beta$ | $\eta$ | MSE-X = CR | MSE-Y = $F_X(x)$ |
|---|---|---|---|---|---|---|---|---|---|
| Internal | | | | | | | | | |
| External | | | | | | | | | |
| Total | | | | | | | | | |

Activity 4 (Steps 5 Through 9): Determine TNI-ER

Step 5—Generate a Tank Failure Probability Distribution CDF, $F_Y(y)$, for the Tank of Interest.

The cumulative density function (CDF) of the tank failure probability distribution, $F_Y(y)$, to which the tank of interest belongs, is computed directly from $F_X(x)$ in Step 5 by a well-established mathematical transformation, which is described in Annex 6. (Note that $F_Y(y)$ could also be called the life expectancy probability distribution.) The CDF is used in this method to describe the probability distributions rather than using the CFD of the empirical data, because it accurately describes the CFD and facilitates the statistical computations to determine TNI-ER. The probability density function (PDF), $f_Y(y)$, however, better illustrates graphically the non-symmetrical and extreme-valued nature of the distribution (e.g., FIG. X3.1), as compared, for example, to a symmetrical normal distribution.

The tank failure distribution, $F_Y(y)$, can be developed in a number of ways. In this method, $F_Y(y)$ is generated from corrosion rate data, and more specifically, the Weibull CDF, $F_X(x)$, generated from the corrosion rate data. As indicated above, two Methods (Methods A and B) can be used to generate $F_X(x)$. Alternatively, $F_Y(y)$ could be developed directly from a population of tanks with the same corrosion and operational conditions that have actually failed. Such data to develop $F_Y(y)$ based on actual tank failures are difficult to obtain and do not include the factor of safety provided by $T_{MAT}$. The use of corrosion rate data is much easier to obtain and use, and the use of $T_{MAT}$ in defining tank failure with such data is conservative and is consistent with industry practice. To be clear, the tank has not actually failed once the minimum allowable thickness, $T_{MAT}$, has been reached, but good industry practice recommends that maintenance and repair be done at that time to avoid the potential of future problems. While this method recognizes the validity of the alternative methods of generating $F_Y(y)$, only the approach using either Method A or Method B is used. Both require a corrosion rate distribution, $F_X(x)$, to be developed from a minimum of 50 independent corrosion rate samples. This method recommends the use of Method A.

In order to compute $F_Y(y)$ from $F_X(x)$ using Method A (or Method B) requires a mathematical transformation involving two random variables to develop a PDF (and a CDF) for a random variable, Y=tank bottom age at failure, $y_i$, which itself is a function, $Y=g(X)$, of another random variable, X=corrosion rate of the tank bottom, $x_i$, where $x_i=y_i/T_{MAT}$, and i=1 to n, where n≥50 and n=number of independent corrosion rate samples. A description of this transformation is presented in Annex A6. This transformation is not simply a calculation of tank age from corrosion rate and the measured bottom thickness. While not intuitive, the resulting PDF (and CDF) of $F_Y(y)$ will always be non-symmetrical probability function even if $F_X(x)$ is a symmetrical probability function.

The density function, $f_Y(y)$, can be generated from the corrosion rate density function $f_X(x)$; the cumulative density function, $F_Y(y)$, is obtained from $f_Y(y)$ by integrating $f_Y(y)$ from 0 to infinity. The most computationally straightforward approach is to develop $f_X(x)$ from $F_X(x)$, where both $f_X(x)$ and $F_X(x)$ are Weibull distribution functions. Once the parameters γ, β, and η of the Weibull probability distribution are derived from $F_X(x)$, $f_X(x)$ can be computed directly from the definition of $f_X(x)$. This can be easily seen from the definitions of $f_X(x)$ and $F_X(x)$.

$$f_X(x)=(\eta/\beta)[(x+\gamma)/\beta^{(\eta-1)}][EXP\{-((x+\gamma)/\beta)^\eta\}] \quad (5.3)$$

and $$F_X(x)=1-EXP\{-((x+\gamma)/\beta)^\eta\} \quad (5.4)$$

Once $f_X(x)$ has been determined, $f_Y(y)$ can be determined from $$f_Y(y)=f_X(g^{-1}(y))*abs[d(g^{-1}(y))/dy] \quad (5.5)$$

where $$f_Y(Y)=(\eta/\gamma)[(x+\gamma)/\beta)^{(\eta-1)}][EXP\{-((x+\gamma)/\beta)^\eta\}] \quad (5.6)$$

and $$F_Y(y)=1-EXP\{-((x+\gamma)/\beta)^\eta\} \quad (5.7)$$

The companion Excel worksheet provided by this method solves these equations and outputs graphs of these probability distributions. FIG. X4.1 in Appendix X4 illustrates such a computation graphically.

Step 6—Generate a Tank Survival Probability Distribution CDF, $S_Y(y)$, for the Tank Being Evaluated.

The cumulative density function (CDF) of the survival probability distribution ($S_Y(y)$) is computed directly from $F_Y(y)$ in Step 5 using the equation $S_Y(y)=1-F_Y(y)$. This is straightforward, because $S_Y(y)$ is obtained by subtracting each value of $F_Y(y)$ from 1.0 for all values of y. The companion Excel Worksheet referred to in this method can be used to compute $S_Y(y)$. FIG. X5.1 in Appendix A5 illustrates such a computation graphically.

Step 7—Generate the Bayesian Survival Probability Distribution $S_Y(y/t_0)$.

Step 7 is to generate $S_Y(y/t_0)$, the Bayesian update of $S_Y(y)$, where $S_Y(y/t_0)$ is the probability of survival given that the tank bottom has survived to an age of $y=t_0$. The sole purpose of the leak detection integrity test performed in Step 2 is to determine whether or not the tank has survived to its present age, $t_0$, so that $S_Y(y/t_0)$ and TNI-ER can be determined. Given that the test result of the integrity test is a PASS, $S_Y(y/t_0)$ can computed directly from $S_Y(y)$. Annex A7 shows how to compute $S_Y(y/t_0)$ from $S_Y(y)$. The Excel spreadsheet provided as part of this method performs the calculation and presents the results both numerically and graphically.

Step 8—Determine the Time to the Next Internal Inspection (TNI-ER) Based on $S_Y(y)$ and $S_Y(y/t_0)$ based on Equivalent Risk.

The Time to the Next Internal Inspection (TNI-ER) that is made using Equivalent Risk is determined from the CDF of survival from $S_Y(y)$ at $t_0$ and the conditional cumulative probability of survival at a future time, $t_0$+TNI-ER, where $S_Y(y=(t_0+TNI-ER)/t_0)=S_Y(y=t_0)$. If the probabilities of survival are the same at two different times and the tank is scheduled for an out-of-serviced API 653 internal inspection at a given probability of survival, $S_Y(y=t_0)$, then the inspection can be performed at either time, $t_0$ or $t_0$+TNI, because the risk or probability of survival (or failure) is the same (i.e., Equivalent Risk).

Step 8—Determine the Time to the Next Internal Inspection (TNI-ER) using Equivalent Risk.

The Time to the Next Internal Inspection (TNI-ER)=$y_2$-$y_1$=$T_N$-$t_0$ is determined from $S_Y(y)$ and $S_Y(y/t_0)$ using Equivalent Risk, where TNI-ER is the difference in age when the conditional survival probability at $y_2=T_N$ (i.e., $S(y_2/y_1)=S(t_N/t_0)$) given that the tank has survived to age $y_1=t_0$ is the same as the unconditional probability at age $y_i$. If the probabilities of survival are the same at two different times and the tank is scheduled for an out-of-service API 653 internal inspection at a given probability of survival, $S_Y(y=y_1=t_0)$, then the inspection can be performed at either time, $t_0$ or $t_0$+TNI-ER, because the risk or probability of survival (or failure) is the same (i.e., Equivalent Risk). Eq. (A7.6) in Annex A7 indicates that conditional probability at age $y_2$, $S(y_2/y_1)$, is equal to the unconditional probability at age $y_1$, $S(y_1)$, when the unconditional probability at age $y_2$, $S(y_2)$ is equal to the square of $S(y_1)$, i.e., $[S(y_1)]^2$. Thus, $S(y=t_N/t_0)=S(y=t_0)$ when $S(y=t_N)=[S(y=t_0)]^2$ and TNI-ER=$t_N$–$t_0$.

As an illustration, assume that the Survival distribution, $S_Y(y)$, is described by a Weibull Distribution with $\gamma=0$, $\beta=2$, and $\eta=25$ and the tank operator/owner wants to determine the time to the next out-of-service API 653 internal inspection based on equivalent risk, TNI-ER, given that it has been $y_1=t_0=20$ years since the last inspection and given that the tank has passed an integrity test at $y_1=t_0=20$ years. The survival probability at 20 years is $S_Y(y_1=20 \text{ yrs})=0.5273$ and the square of the survival probability at 20 years is $S_Y(y_1=20 \text{ yrs})^2=(0.5273)^2=0.2780$. The age at $y=y_2$ can be determined from the Weibull tables ($y_2=28.2840$), or it can be computed directly using the inverse function of the Weibull Survival Distribution, $S^{-1}(y_2)=\eta*\text{EXP}[\ln(-\ln(S_Y(y_2))/\beta]=25*\text{EXP}[\ln(-\ln(0.278037)/2]=25*1.131371=28.284$. TNI-ER=$y_2$–$y_1$=28.2840–20=8.2840 years.

The Excel worksheet attached as part of this method will compute TNI-ER=$y_2$–$y_1$=$T_N$–$t_0$ directly. As stated above, the Excel spreadsheet will yield TNI-ER once the following parameters are entered into the spreadsheet:

(1) the current age of the tank in years since the last out-of-service bottom inspection of the tank bottom (either a previous API 653 internal inspection or when the tank was new) at the time of the application of this method, $t_{0\ age}$, where $t_0=t_{0\ age}$, $-t_{P\ age}$.

(2) the mean measurement of the bottom thickness, $T_{min}$, in inches, determined in Step 3 of this method at $t_{0\ age}$, (3) the age of the tank in years when the thickness of the tank bottom was last made, $t_{P\ age}$, where $t_P=t_{P\ age}$, $-t_{P\ age}=0.0$ and (4) the mean thickness of the tank bottom at $t_{P\ age}$.

The Excel worksheet solves this equation for TNI-ER and outputs a numerical value and a plot of $S(y/y_1)$ superimposed on $S(y)$ and covering the region from $y_1$ to $y_2=t_0$ to $t_N$. If no additional bottom thickness and corrosion rate information are available or are obtained as part of this method, then output of TNI-ER is equal to TNI. If addition bottom information is available or is obtained, the worksheet will also compute TNI-$\alpha$ as described in Activity 5, Steps 9-11, and then output TNI based on both TNI-ER and TNI-$\alpha$, Step 12.

It should be noted that the TNI-ER for tanks computed using Equivalent Risk increases with decreasing survival probability, $S_Y(y)$, which accounts for the fact that as the tank ages, it is no longer subject to many of the failure mechanisms that may have impacted younger tanks. The opposite is also true, i.e., the Equivalent Risk decreases with increasing survival probability, which accounts for the fact if a tank is young, the impact of certain failure mechanisms, like excessive tank bottom corrosion, may not have yet occurred or have been detected. Thus, the TNI-ER computed when $S_Y(y)<50\%$ is greater than when $S_Y(y)>50\%$. This result seems counterintuitive, but it is correct. When the tank or tank bottom is relatively new, it may not have survived long enough to experience one or more of the tank bottom failure mechanisms that might shorten the serviced life of a tank. However, once the tank has aged through one or more of these failure mechanisms without experiencing failure, it will have a longer service life expectancy, i.e., the longer the tank survives, the longer the tank will survive. Table X9.1 illustrates how TNI-ER changes for different ages and survival probabilities based on the graphical illustrations in FIGs. X9.1-X9.4 in Appendix X9.

The tank owner/operator can take advantage of a higher survival probability if additional measurements of the thickness and corrosion rate of the entire tank bottom are made and used in computing TNI. Steps 9 through 11 describe methods of determining TNI-$\alpha$ when additional information about the entire tank bottom is available or is obtained as part of this method and how it can be used in determining TNI with TNI-ER.

Activity 5 (Steps 9 Through 11): Determine TNI-$\alpha$

Step 9—Determine if Additional Thickness and Corrosion Rate Information of the Entire Tank Bottom be Made and Used to Improve TNI-ER?

Steps 9, 10, and 11, can be used to make another estimate of TNI (i.e., TNI-$\alpha$), but only if (1) additional measurements of the thickness and corrosion rate across the entire tank bottom are obtained or made and (2) the survival probability at time $t_0$ is greater than 50%. Step 9 determines whether or not measurements of the thickness and corrosion rate for the entire tank bottom are available or can be made, and if so, can they be used to make a determination of TNI. The determination of TNI-a made in Steps 9 through 11 from additional in-service tank bottom measurements takes advantage of the higher survival probabilities of $S_Y(y)$.

The flow chart in FIG. X2.1 shows a detailed decision and measurement logic for collecting the additional measurements and using them to compute TNI-$\alpha$. It is important to note that TNI can always be determined using TNI-ER without any additional tank bottom measurements, and an out-of-service API 653 internal inspection can always be performed regardless of the survival probability region.

If additional measurements of the thickness and corrosion rate across the entire tank bottom are available (e.g., from a previous out-of-service API 653 internal inspection) or can be made (e.g., using an Acoustic Emission Corrosion Activity Test (AECAT)), then the survival probability age region at $t_0$ needs to be determined to assess whether or not the additional measurements that can be used to compute TNI-$\alpha$ can be used to help determine TNI. The survival probability distribution is divided into four Survival Probability Age Regions for this purpose. They are illustrated in FIGs. X8.1 and X8.2 in Appendix 8 and are defined as follows:

Survival Probability Age Region A: $S_Y(y)>95\%$
Survival Probability Age Region B: $50\% \leq S_Y(y) \leq 95\%$
Survival Probability Age Region C: $5\% \leq S_Y(y) \leq 50\%$
Survival Probability Age Region D: $S_Y(y)<5\%$ If the age of the tank at $t_0$ is in Survival Probability Age Region D, then this method shall not be used and this method recommends that an out-of-service API 653 internal inspection be performed. Survival Probability Age Region D is defined by a 5% tail. If the age of the tank at $t_0$ is in Survival Probability Age Regions A or B, then in Step 12, the TNI-$\alpha$ that is determined in Step 11 can be used with the TNI-ER determined in Step 8 to determine TNI. TNI-ER is determined for Survival Probability Age Regions A, B, and C. While TNI-ER could be determined for Survival Probability Age Region D, it is difficult to accurately define the tails of the distribution accurately enough to be reliable enough to determine TNI-ER for this region where the probability of tank or tank bottom failure is very high.

The 5% and 95% survival probabilities are used to develop the Survival Probability boundaries for Survival Probability Age Regions A and D, because it is difficult to obtain enough data to accurately model the tails of the distribution. The user of this method may use smaller tails like 2.5% and 97.5%, if it can be demonstrated that the tails of the CDF are supported by data. This method recommends using the Survival Probability Age Regions as defined in this step.

Step 10—Determine the Minimum Bottom Thickness and the Maximum Corrosion Rate for the Entire Tank Bottom Using One of the Three In-service Measurement Methods.

If additional measurements of the thickness or corrosion rate are available or can be measured for the entire tank bottom, then a second estimate of TNI can be made (TNI-α). This method provides three acceptable methods for determining the minimum thickness, $T_{min}$, and maximum corrosion rate, $CR_{max}$, for the entire tank bottom to use in determining TNI-α. Once $T_{min}$ and $CR_{max}$ are known for the entire tank bottom, TNI-α can be computed for $T_{MAT}$ using the general formula $$TNI\text{-}\alpha = (T_{min} - T_{MAT})/CR_{max} \qquad (5.8)$$

where $T_{min}$ and $CR_{max}$ can be determined from (a) the maximum corrosion anywhere on the tank bottom, whether due to underside/external and topside/internal corrosion, or (b) the sum of the maximum underside/external and topside/internal corrosion even if they do not coincide. There are two ways to address (b). First, when a previous out-of-service API 653 internal inspection exists (b) can be determined directly from the API 653 report. Second, when only measurements of the tank bottom exist, it is assumed that $T_{min}$ and $CR_{max}$ are controlled by underside/external corrosion and $T_{min}$ and $CR_{max}$ are multiplied by 0.71 and 1.4, respectively, to account for underside/external and topside/internal corrosion coinciding.

This method includes three methods of extrapolating the bottom thickness and corrosion measurements made in Step 3 to the entire tank bottom.

(1) Spatial Method 1—AECAT: an Acoustic Emission Corrosion Activity Test (AECAT) indicating no or minimal corrosion activity as indicated in [11] for tanks Graded A and B, when Grade B does not indicate any concentration of localized corrosion activity, so that the measurement of bottom thickness and corrosion rate at one or only a few locations on the tank bottom can be assumed to be representative of the entire tank bottom.

(2) Spatial Method 2—A Previous API 653 Internal Inspection: a previous out-of-service API 653 Internal Inspection, or equivalent, (a) with tank bottom thickness measurements across the entire tank bottom that include pitting and localized regions of extreme thinning and (b) with some of the tank bottom thickness measurements made in proximity to the local bottom thickness measurements made in Step 2 of this method. These previous API 653 internal inspection measurements will be adjusted proportionally by the ratio of the current and previous measurements of the thickness or corrosion rate of the tank bottom.

(3) Spatial Method 3—Both AECAT and A Previous API 653: Spatial Methods 1 and 2 in combination.

(1) Spatial Method 1—AECAT: Studies with a large number of tests (e.g., ~150) indicate that if an AE Corrosion Activity Test (AECAT) is performed, and if the result indicates little or no corrosion, i.e., Grade A or Grade B when no localized regions of high corrosion activity exist, then there is no or minimal active corrosion of the tank bottom and the results of these studies indicate that no maintenance or repair of the tank bottom is necessary. This result was determined from the out-of-service API 653 internal inspections performed on the tanks in the test study [11] immediately after perform the AECAT test. Thus, if the AE Corrosion Activity Test is graded as an A (or a B with no local regions of high corrosion activity), then $T_{avg}$ and $CR_{avg}$ determined at one location (or only a few locations) in the tank in Step 3 can be assumed to be representative of uniform corrosion across the entire tank bottom and can be used to compute TNI-α using Eq. {(5.8)}. If the tank owner/operator wants to be very conservative, $T_{avg}$ and $CR_{avg}$ can be computed assuming the minimum thickness and the maximum corrosion rates from the underside/external and the topside/internal coincide. $T_{avg}$ and $CR_{avg}$ is obtained by multiplying $T_{avg}$ determined in Step 3 by 0.71 and by multiplying $CR_{max}$ in Step 3 by 1.4. If the AE results do not show no or very low corrosion activity, i.e., Grades of C, D, or E, then TNI-α cannot be computed using the AECAT measurements.

It is important to note that the objective of the AE Corrosion Activity Test is NOT to determine the presence or the level of the corrosion activity. Rather, the objective is to determine when corrosion activity is NOT present. The studies indicate that this is a highly reliable measurement for AECAT [11].

(2) Spatial Method 2—A Previous API 653: Spatial Method 2 uses the results of a previous API 653 out-of-service internal inspection to determine TNI-α, but corrects the maximum corrosion rate and minimum thickness from the previous internal inspection by the ratio of the local measurement of the corrosion rate of the bottom made in Step 3 and the previous API 653 measurement of corrosion rate made at approximately the same location.

(3) Spatial Method 3—Both AECAT and A Previous API 653: The approach for using Spatial Method 3, the results of an AECAT test indicating no or very low corrosion activity in combination with $T_{min}$ and $CR_{max}$, which is determined from a previous out-of-service. AOI 653 internal inspection, has the advantage over the use of only a previous out-of-service API 653 internal inspection in Spatial Method 2, because it provides an up-to-date assessment of the corrosion activity condition of the tank bottom. While a previous out-of-service API 653 internal inspection will provide more detailed measurements of bottom thickness across the entire tank bottom, these thickness measurements are almost always obtained at least 10 years earlier in time and are only indicative of what to expect based on the previous and unrepaired condition of the tank bottom. Since any areas of severe corrosion identified during the previous API 653 inspection were repaired, including removing the source of the corrosion, only the other areas should be relevant for future forecasts. This method, however, uses the worst case condition found in this previous API 653 inspection to estimate the minimum thickness, $T_{min}$, and the maximum corrosion rate, $CR_{max}$, at $t_0$.

When Spatial Methods 2 or 3 are used, the thickness and corrosion rate can be determined from a previous out-of-service API 653 internal inspection from the minimum thickness, $T_{min}$, and the maximum corrosion rate, $CR_{max}$, computed from it, by assuming that the topside/internal and underside/external corrosion from anywhere in the tank bottom are added together under the assumption that the worst case condition occurs when the underside/external and topside/internal corrosion occur at exactly the same location. This method recommends following this approach when using the results from previous API 653 internal inspections to computed $T_{min}$ or $CR_{max}$. This method gives the tank owner/operator the option, however, to use either the minimum thickness due to underside/external or the combination of underside/external and topside/internal corrosion when using the historical corrosion data provided in this method.

Step 11—Determine the Time to the Next Internal Inspection (TNI-α) Based on Measurements of the Minimum Thickness and Maximum Corrosion Rate for the Entire Tank Bottom Made in Step 10.

This method provides three acceptable methods for determining TNI-α in Survival Probability Age Regions A and B based on any one the three measurements of $T_{min}$ and $CR_{max}$ made in Step 10. If the additional measurements provided in Step 10 are acceptable, then the objective of Step 11 is to compute time to the next out-of-service inspection, TNI-α, using these methods. Table 8 summarizes TNI-α derived as a function of (1) corrosion rate, (2) the type or types of the Spatial Method(s) used and the results of the Spatial Method(s) to determine TNI-α, and (3) the Survival Probability Age Region where TNI-α can be used.

If the age of the tank at the time, $t_0$, falls into Survival Probability Age Region D, then this method shall not be used and this method recommends that an out-of-service API 653 internal inspection be performed. If the age of the tank falls into Survival Age Region A or B and additional tank bottom measurements are obtained that meet the criteria in this method in Step 10, then TNI-α can be determined and used in the appropriate combination with TNI-ER when determining TNI in Step 12.

TNI-α will be between 1 year and 10 years. If the TNI-α determined through the calculations is greater than 10 years, it will be limited to 10 years. Additional life may be present in the tank bottom, but this needs to be verified by re-performing this method. This 10-year re-assessment is consistent with API 653 for RBI methods. If the age of the tank falls into Survival Probability Age Region C, which means the survival probability is less than or equal to 50%, then TNI-α cannot be used as part of this method and TNI is determined solely by TNI-ER.

Six measurement cases or scenarios are described below for determining TNI-α for various combinations of Spatial Methods 1, 2, and 3. Table 8 summarizes the determination of TNI-α and how $CR_{max}$ is defined for each of the six cases. $CR_{max}$ is defined in terms of (a) the maximum corrosion rate due to underside/external pitting determined in Step 3b, (b) an estimate of determining the maximum corrosion rate due to underside/external and topside/internal pitting determined in Step 3b by multiply $CR_{max}$ in (a) by 1.4, (c) the maximum pitting determined in a previous out-of-service API 653 internal inspection after adjusting the maximum corrosion rate measured in this previous API 653 inspection by the ratio of the corrosion rates, $CR_{avg}$, measured in Step 3b and at the same approximate location in the previous API 653 inspection, and (d) by the average of the determinations made in (b) and (c). This determination of TNI-α in Cases 1 through 6 is only valid for use with this method in Survival Probability Age Regions A and B.

TABLE 8

Summary of the Determination of TNI for Methods 1-3

| Case | Method | Results AECAT | Previous API 653 | CRmax (mpy) | TNI-α (mpy) |
|---|---|---|---|---|---|
| 1 | 1 | Pass—No Active Corrosion | No | $1.0*CR_{ext}$ or $1.4*CR_{ext}$ | Yes for Age Regions A & B |
| 2 | 1 | Fail—Active Corrosion | No | $1.4*CR_{ext}$ | N/A |
| 3 | 1 | No AECAT Test | No | $1.4*CR_{ext}$ | N/A |
| 4 | 2 | No AECAT Test | Yes | Avg{Adj[$CR_{int}$ + $CR_{ext}$]; $1.4*CR_{ext}$}** | Yes for Age Regions A & B |
| 5 | 3 | Pass—No Active Corrosion | Yes | Min{Adj[$CR_{int}$ + $CR_{ext}$]; $1.0*CR_{ext}$} | Yes for Age Regions A & B |
| 6 | 3 | Fail—Active Corrosion | Yes | Max {$1.4*CR_{ext}$; Adj[$CR_{int}$ + $CR_{ext}$]} | Yes for Age Regions A & B |

*Max TNI = 10 years; Min TNI = 1 year because Tank meets min qualifications for use of this method Case 1.

Case 1 summarizes TNI for an AECAT test result in which no active corrosion was measured and in which a previous out-of-service API 653 internal inspections is not available. For Case 1, the tank owner/operator can use either the $CR_{max}$ measured in Step 3 using only the underside/external maximum pitting corrosion rate measurement measured by the corrosion data set provided as part of this method, or if the tank owner/operator wants to be very conservative, they can assume that the maximum underside/external and topside/internal corrosion rates occur at the same identical location and are added together. This is accomplished by multiplying the underside/external corrosion rate, $CR_{max}$, by 1.4, which is a ratio between the baseline underside (5 mpy) and the topside (2 mpy) corrosion rate used in API 653. TNI-α is determined for the AECAT tank bottom measurements in this step (Step 10) using Eq. ({5.8}). This method recommends using $1.0*CR_{max}$.

Case 2.

Case 2 summarizes TNI for an AECAT test result in which active corrosion was measured and in which a previous out-of-service API 653 internal inspections is not available. Because the AECAT indicates active corrosion, $T_{min}$ and $CR_{max}$ cannot be determined for the entire tank bottom and TNI-α cannot be computed. This method recommends using $1.4*CR_{max}$.

Case 3.

Case 3 summarizes TNI for the case where an AECAT test was not performed and where a previous out-of-service API 653 internal inspection is not available. The results for Case 3 are identical to those for Case 2. This method recommends using $1.0*CR_{max}$.

Case 4.

Case 4 summarizes TNI for the case where an AECAT test was not performed and where a previous out-of-service API 653 internal inspection is available. $T_{min}$ and $CR_{max}$ can be computed directly from the previous out-of-service API 653 internal inspection and then adjusted for the level of corrosion that occurred between times $t_P$ and to using the ratio of the measurements of the corrosion rate, $CR_{avg}$ or $CR_{max}$, measured in Step 3 at $t_O$ and at the same approximate location in the previous API 653 internal inspection measured at $t_P$. The determination assumed that the maximum underside/external corrosion rate is added to the maximum topside/internal corrosion rate from the previous API 653 report. This method recommends using the average of the maximum corrosion rate determined in Step 3 with a multiplier of 1.4 on $CR_{max}$ (i.e., $1.4*CR_{max}$) and the adjusted maximum corrosion rate determined in the previous API 653 internal inspection (Adj $[CR_{underside}+CR_{topside}]$= Adj $[CR_{ext}+CR_{int}]$).

Case 5.

The results for Case 5 are identical to Case 4 except an AECAT test was performed and no active corrosion activity was detected. This method recommends using the minimum of the maximum corrosion rate determined in Step 3 with a multiplier of 1.0 on $CR_{max}$ (i.e., $1.0*CR_{max}$) and the adjusted maximum corrosion rate determined in the previous API 653 internal inspection (Adj$[CR_{underside}+CR_{topside}]$=Adj $[CR_{ext}+CR_{int}]$).

Case 6.

Case 6 is similar to Case 4 except the AECAT test that was performed showed active corrosion activity. For Case 6, the $CR_{max}$ used to compute TNI-α is determined from the maximum of $1.4*CR_{max}$ measured in Step 3b and the adjusted maximum corrosion rate determined in the previous API 653 internal inspection (Adj $[CR_{underside}+CR_{topside}]$=Adj $[CR_{ext}+CR_{int}]$).

Cases 4 through 6 illustrate how TNI is more conservatively determined as the number and quality of the results from additional tank bottom measurement methods described in Step 10 decrease, i.e., TNI-α becomes smaller. There is tank owner/operator choice in determining TNI-a for some of the cases specified in this method, because of the options available to the tank owner/operator when determining $CR_{max}$. The tank owner/operator can always use a more conservative option (i.e., a greater corrosion rate and/or a smaller bottom thickness). This method allows this flexibility because the $CR_{max}$ determined from $CR_{max\ pitting}$ using the corrosion study data provided as part of this study is typically the most conservative estimate of $CR_{max}$ and typically produces the largest corrosion rates.

Activity 6 (Step 12): Determine TNI from TNI-ER and TNI-α, where TNI≤10 Years.

Step 12—Determine TNI from TNI-ER and TNI-α, where TNI≤10 Years.

The objective of Step 12 is to determine the time to the next out-of-service API 653 internal inspection (TNI=$\Delta t_{0-N}$) based on the appropriate combination of TNI-ER and TNI-α, where TNI shall be ≤10 years and $\Delta t_{N-P}$ shall be ≤30 years (or as specified in API 653). TNI-ER is determined in Step 8, and TNI-α is determined from one or more of the three Spatial Methods described in Step 11.

TNI, which is summarized in Tables 9 and 10, is determined from the appropriate combination of TNI-ER and TNI-α. Table 9 presents an overview for each Survival Probability Age Region, and Table 10 presents a detail summary on how to compute TNT from TNI-ER and TNI-α for the six cases described in Step 11. TNI is dependent on the Survival Probability Age Region, the maximum corrosion rate, and whether or not additional tank bottom thickness and corrosion rate measurements were made for the entire tank bottom, and if additional measurements of the tank bottom were made, the number and type of Spatial Methods used and the results for each Spatial Method used.

If the age of the tank at the time, $t_O$, falls into Survival Probability Age Region D, then TNI should not be computed and this method recommends that an out-of-service API 653 internal inspection be performed. If the age of the tank falls into Survival Age Region A or B and additional tank bottom measurements were obtained in Step 11, then TNI-α can be used in combination with TNI-ER, as summarized in Table 10, to determine TNI. If the age of the tank falls into Survival Age Region C, which means the survival probability is less than or equal to 50%, then TNI-α cannot be used and TNI is determined by TNI-ER.

As stated above, TNI will be limited to between 1 year and 10 years. If TNI is greater than 10 years, it will be limited to 10 years. A 10-year re-assessment can be performed using this method to determine if there is additional service in the tank bottom, or an out-of-service API 653 internal inspection can be performed. This 10-year re-assessment is consistent with the practice in API 653 for risk-based methods. The total time between out-of-service API 653 internal inspections ($t_N$–$t_P$) cannot be any longer than that specified in API 653, which is 30 years.

Table 10 describes how to combine TNI-ER and TNI-α for each of the six possible cases or possible test results for Spatial Methods 1, 2, and 3. As an illustration, TNI in Table 10 for Case 4 indicates that TNI is determined from Max {TNI-ER; Avg[TNI-ER; TNI-α]}, which is the maximum value of either TNI-ER or the average of TNI-ER and TNI-α. As stated in Step 11, TNI is the longest and $CR_{max}$ is the smallest as the number and reliability of the test results using Spatial Methods 1, 2, and 3 increase.

TABLE 9

Computation of the Time to the Next Out-of-Service API 653 Internal Inspection (TNI)

| Survival Age Region | Integrity Test Result | TNI-ER | TNI-α | TNI |
|---|---|---|---|---|
| A | PASS | Max {TNI-ER; 1 yr} | TNI-α | Combination of TNI-ER & TNI-α (1 to 10 yrs) |
| B | PASS | Max {TNI-ER; 1 yr} | TNI-α | Combination of TNI-ER & TNI-α (1 to 10 yrs) |
| C | PASS | TNI-ER | N/A | TIN-ER (1 to 10 yrs) |

TABLE 9-continued

Computation of the Time to the Next Out-of-Service API 653 Internal Inspection (TNI)

| Survival Age Region | Integrity Test Result | TNI-ER | TNI-α | TNI |
|---|---|---|---|---|
| D | PASS or FAIL | API 653 Internal Inspection Recommended | N/A | API 653 Internal Inspection Recommended |

TABLE 10

Summary of the Determination of TNI for Spatial Methods 1 to 3

| Case | Method | Results AECAT | Previous API 653 | CRmax (mpy) | TNI-ER (mpy) | TNI-α (mpy) | TNI* (mpy) |
|---|---|---|---|---|---|---|---|
| 1 | 1 | Pass-No Active Corrosion | No | $1.0*CR_{ext}$ or $1.4*CR_{ext}$ | Yes | N/A | TNI-ER |
| 2 | 1 | Fail-Active Corrosion | No | $1.4*CR_{ext}$ | Yes | N/A | N/A |
| 3 | 2 | No AECAT Test | No | $1.4*CR_{ext}$ | Yes | N/A | TNI-ER |
| 4 | 2 | No AECAT Test | Yes | $\text{Avg}\{\text{Adj}[CR_{int} + CR_{ext}]; 1.4*CR_{ext}\}$ | Yes | Yes for Age Regions A&B | $\text{Max}\{\text{TNI-ER}; \text{Avg}[\text{TNI-ER}; \text{TNI-α}]\}$ |
| 5 | 3 | Pass-No Active Corrosion | Yes | $\text{Min}\{\text{Adj}[CR_{int} + CR_{ext}]; 1.0*CR_{ext}\}$ | Yes | Yes for Age Regions A&B | $\text{Max}\{\text{TNI-ER}; \text{TNI-α}\}**$ |
| 6 | 3 | Fail-Active Corrosion | Yes | $\text{Max}\{1.4*CR_{ext}; \text{Adj}[CR_{int} + CR_{ext}]\}$ | Yes | Yes for Age Regions A&B | $\text{Min}\{\text{TNI-α}; \text{Avg}\{\text{TNI-ER}; \text{TNI-α}\}$ |

*Max TNI = 10 years; MM TNI = 1 year because Tank meets min qualifications for use of this method
**Minimum for Modified Grade C

6.0 Apparatus

Five different types of in-service tank measurement, test, and inspection methods, which are in accordance with the precision and bias of this method, may be used to provide the data to implement this method: (1) a leak-detection integrity test; (2) tank bottom thickness measurements at one or more tank bottom locations; (3) an acoustic emission (AE) corrosion activity test (AECAT); (4) an API 653 external inspection; and (5) the thickness measurements and corrosion rates from a previous out-of-service API 653 internal inspection of the tank bottom. Each of these types of measurements has potential sources of interference that need to be addressed to meet the precision and bias criteria in Section 16. This method requires the use of the first two measurement sensor systems in Activity 2, Steps 2 and 3. The previous out-of-service API 653 internal inspection used to address (5) does not have to be used when implementing this method, but if available, and if it meets the criteria specified in this method, it should be used.

This method does not require the use of a specific type of leak detection integrity method or system, a specific type of tank bottom thickness measurement sensor or sensor technology, or a specific type of AE sensor or AE Corrosion Activity Test method or system. This method does require that the methods or sensor systems used to test the tank for integrity, for bottom thickness, and for corrosion rate meet a specified level of demonstrated performance. If this level of performance is met, then TNI determined by this method can be used.

6.1 Leak Detection Integrity Methods or Systems:

Only leak detection integrity test methods that meet the following criteria shall be used to test the tank for leaks, where a leak in the tank bottom represents a lack of tank bottom integrity (i.e., no more service life).

6.1.1 Single-bottom ASTs (and bulk USTs) shall be tested for integrity using only leak-detection integrity tests methods that have been evaluated for performance by an independent third-party following one of the method evaluation protocols developed by or accepted by the U.S. EPA, the NWGLDE, a nationally recognized evaluation organization, a recognized industry standards organization, or a national consensus standards organization. Both in-tank and ex-tank methods are acceptable.

6.1.2 Double-bottom tanks shall be tested for integrity using only leak detection methods that have either (1) been approved by and performed under the supervision of a PE or a person certified by a recognized industry standards organization or a national consensus standards organization, or (2) been evaluated for performance by an independent third-party following one of the standard evaluation protocols developed by or accepted by the U.S. EPA, the NWGLDE, a nationally recognized evaluation organization, a recognized industry standards organization, or a national consensus standards organization. Both in-tank and ex-tank methods are acceptable.

6.1.3. The individual measurement systems comprising the leak detection integrity methods for both single- and double-bottom ASTs must be calibrated annually according to the manufacturer's specification.

6.1.4 For all single-bottom tanks, the results of the performance evaluation shall be documented in a report prepared by an independent, third-party evaluator following the guidelines specified in the evaluation protocol.

6.1.5 The leak-detection integrity test method for single-bottom tanks shall be operated in accordance with the evaluation report to achieve the evaluated performance. For most methods used to test ASTs, this means that the test method should be operated to achieve a probability of detection ($P_D$) of 95%, or greater, against a specified leak rate (LR) and a probability of false alarm ($P_{FA}$) of 5%, or less.

6.1.6 The leak detection integrity test method for double-bottom tanks shall be operated in accordance with the instructions of PE, or in accordance with an evaluation report to achieve the desired level of performance.

6.1.7 Any leak detection method that is currently listed by the NWGLDE or has been evaluated for performance by Ken Wilcox & Associates, or another equivalent nationally recognized evaluation organization, can be used to perform a leak-detection integrity test.

6.2 Bottom or Floor Thickness Measurement Sensor System:

The tank bottom thickness measurements shall be shall be performed with a sensor system that is capable of measuring the thickness of the tank bottom floor plate with a precision of 0.010 in. and a bias of 0.010 in. Averaging or combining multiple measurements using standard statistical methods can be used to meet or improve upon the precision and bias of the sensor system.

6.3 AE Sensors Used in an AE Corrosion Activity Test (AECAT):

There are a number of different types and brands of acoustic sensors and acoustic methods for measuring the corrosion activity of the bottom of a tank. A corrosion activity test is comprised of AE sensors placed on the external shell of the tank or submerged in the product in the tank, where the coverage achieved at one or more measurement locations is sufficient to detect corrosion activity at any location on the tank bottom. The acoustic measurement array should be comprised of one or more sensors, and generally, a minimum of three positions on the tank wall or on the submerged array, where each sensor should have sufficient SNR to detect corrosion activity over a designated area covering the tank bottom. Preferably, at least one of the three sensors should be at a different elevation than the other two sensors. The number and SNR shall be demonstrated before or after each test through a simple calibration test showing that the system can detect a calibration signal with sufficient SNR to achieve an SNR of 10 dB when detecting corrosion activity signals. As with the leak detection methods, the data processing algorithms required to detect the presence of the corrosion activity are usually considered proprietary.

6.4 API 653 External Inspection:

The API 653 external inspection should be performed following the requirements for external inspections in API 653 by a certified API 653 inspector. The external inspection should be performed within 5 years of the application of this method and within each succeeding 5-year period to continue to use the results of the method during the TNI time period determined by this method.

6.5 API 653 Internal Inspection:

In addition to the four types of measurements, tests, and inspections specified in sections 6.1-6.4, this method may use the thickness measurements made over the entire tank bottom from a previous out-of-service API 653 internal inspection, where these measurements should be updated by the ratio of the average bottom thickness obtained with the current in-service measurement of bottom thickness in Step 3 and a previous bottom thickness obtained from the previous API 653 Report in the same approximately location as the current measurement.

7.0 Interferences

Each of the measurements and tests used to assess the condition of the tank bottom has potential sources of interference that need to be addressed to obtain the performance specified by the manufacturer. Section 10 describes whether or not these sources of interference affect the measurement, and if they do, how these sources of interference are addressed.

7.1 Leak-Detection Integrity Test:

The survival of a tank at $t_0$ is determined by whether or not the tank bottom has integrity. Integrity is assessed by PASSing a leak-detection integrity test in accordance with the criteria specified in this method. The test methods used to assess tank bottom integrity in ASTs (and bulk USTs) require that a number of sources of interference, which may impact the results, be compensated for or addressed as part of the test method, because these sources of interference may be as large, or larger than the leak to be detected. These sources of interference, or instrumentation system and ambient background noise, as they are also referred, may produce false alarms or missed detections. Each type of method will be affected by different sources of interference or noise. The third-party evaluation protocol is designed to evaluate the method under a wide range of interferences or noise. The third-party performance report indicates how well this was accomplished.

As an illustration, the thermal expansion/contraction of the liquid product in the tank, or the thermal expansion the tank walls, the measurement sensors, and the mounting systems are all examples of sources of interference for testing ASTs using an in-tank method like a volumetric or a mass-based leak detection method. As another illustration, external methods of leak detection, which are based on the analysis of the liquid product or tracers in the liquid product that escapes from a hole in the bottom of the tank, may be degraded by the presence of liquid product already present in the backfill and soil beneath the tank. As part of this method, each important interference source shall be addressed and a determination shall be made as to whether or not these sources of interference affect the measurement. How well the leak detection method does in addressing these interferences is determined by the performance of the method when testing an AST in the presence of such interferences. Performing a third-party evaluation of performance using an evaluation protocol that includes a wide range of these interferences during the evaluation is one way to address how well the method does in addressing these interferences. Another way is to use an evaluation protocol approved by the US EPA, or accepted by the NWGLDE or a nationally recognized evaluation organization, because such interferences are included in these evaluation protocols.

7.2 Tank Bottom Thickness Measurement:

There are many types of sensors that can measure the thickness of the bottom steel plate of the tank. Coatings, liners, sludge, sediment, water, uneven bottom surfaces, or pitting may impact the precision and bias of the bottom thickness measurements. For each type of sensor system, the sources of interference shall be addressed and a determination shall be made as to whether or not these sources of interference adversely affect the measurement. How well the bottom thickness sensor systems address these sources of interference is determined by the precision and bias of the sensors when evaluated under such interferences.

7.3 AE Corrosion Activity Test:

There are many types of acoustic sensors and acoustic methods for measuring the corrosion activity of the tank bottom. The sources of interference for this measurement method shall be described and a determination shall be made as to whether or not these sources of interference affect the measurement, and if they do, how these interferences are addressed. Each AE Corrosion Activity Test (AECAT) shall include the use of a calibration signal that insures the AE has sufficient signal-to-noise ratio (SNR) in the presence of these sources of interference to detect the corrosion activity.

This signal can be generated in the product or on the external wall of the tank. The calibration method will be described and used as part of the AE method.

7.4 The external and internal inspections performed as part of this method shall be in accordance with API 653 and the criteria specified in this method. Only complete and properly performed and reported inspections shall be used.

8. Personnel Qualifications 8.1 The assessment method described in this method for determining TNI shall only be performed by personnel who have been trained to implement this method and who are under the supervision of either a Certified API 653 Inspector, a professional engineer (PE), or a subject matter expert (SME).

8.2 The personnel performing a leak-detection integrity test shall be trained in the use of the method by the testing company or under the supervision of a professional Engineer (PE), or a subject matter expert (SME).

8.3 An API 653 External Inspection of an AST shall be performed only by personnel who are certified by and have successfully completed an API training class to become a certified inspector, or an equivalent.

8.4 The tank bottom or floor thickness measurements shall be shall be performed by personnel who are certified by NACE, API, or other equivalent professional organizations in the specific bottom measurement system being used, or personnel who are trained by and work under the supervision of a Certified API 653 Inspector, a PE, or a SME.

8.5 Only out-of-service API 653 Internal Inspection Reports that (a) are performed by a certified API 653 inspector, (b) include and report sufficient tank bottom thickness measurements that indicate the underlying mean (or median) and minimum bottom thickness of the entire tank bottom due to localized uniform corrosion, pitting, or thinning, and (c) include and report one or more thickness measurements in close proximity to the bottom thickness measurement made in Step 2 of this method (i.e., usually on the same welded bottom plate or adjacent plates) shall be used. The minimum thickness and maximum corrosion rate determined in the previous API 653 internal inspection shall be updated proportionally to the current in-tank measurement of the bottom thickness by the ratio of the bottom thickness measurements made at the location of the bottom thickness measurements made in Step 2 of this method.

9.0 Hazards

Sensors, sensor system, electronic system, data acquisition systems, and/or computers shall meet the appropriate safety methods in accordance with the storage tank facility safety requirements.

10.0 Sampling, Test Specimens, and Test Units 10.1 Leak Detection Integrity Methods or Systems:

An AST with a single-bottom shall be tested for integrity following the testing protocol specified in the independent third-party evaluation report. The output of the leak detection integrity test will be a Pass or a Fail using one or more thresholds to declare a leak at the specified level of performance. For in-tank volumetric, mass-based, and tracer test methods, the leak detection test will be operated as indicated by the third-party evaluation report to detect a specified leak rate where the system is operated to have a $P_D \geq 95\%$ and a $P_{FA} \leq 5\%$. For other systems, the threshold will be specified in the third-party evaluation report. The data collected and the analysis performed to obtain the test result will follow the protocol in the third-party evaluation report.

An AST with a double-bottom shall be tested for integrity following the testing protocol specified by the manufacturer and approved by a PE The data collected and the analysis performed to obtain the test result will follow the protocol specified by the manufacturer or developer of the method and approved by a PE If a tank with a double-bottom is tested for integrity with a third-party evaluated method, the test should be performed following the same procedure as described for single-bottom tank tests.

10.2 Bottom Thickness Measurement Sensor System:

A minimum of four, and preferably 5, independent replicate measurements of the thickness of the tank bottom shall be made in at least one location on the bottom of the tank; these replicate measurements result in a total of 8 and preferably 10 bottom thickness measurements at each location. (If a spatial sensing system (i.e., not a point measurement system is used, then a total of 8 to 10 measurements at one location will suffice.) The mean, median, maximum, minimum, and standard deviation shall be computed. The thickness of the bottom plate shall be determined by the mean or median provided all of the individual data points are within three, and no more than five, standard deviations the from the mean value. If not, the outlier points should be removed when determining the mean provided that a minimum of eight thickness measurements are used; if not, the thickness measurements shall be repeated. If the same result occurs, the thickness measurements should be made at another location. The objective is to determine the average tank bottom thickness, i.e., uniform corrosion rate of the tank.

10.3 AE Corrosion Activity Test (AECAT):

An AE Corrosion Activity Test shall be performed following the manufacturer's testing protocol. Most test protocols require AE measurements to be made at a specified product level as a percentage of capacity, use a waiting period of 6 to 12 h or longer, and to collect 30 min to 1 h of AE data. The level of active corrosion of the bottom of the tank is determined from the number and spatial distribution of the individual corrosion activity impulsive signals that are detected and located on the bottom or floor of the tank.

The results are graded from A to E following [11]. Grade A indicates that there is no active corrosion activity of the tank bottom and that no maintenance or repair of the tank bottom is required. Grade B indicates some active corrosion activity may be occurring, but no maintenance or repair of the tank bottom is required. The AECAT test result is a pass if a Grade A result is achieved. A Grade B test result is also a pass provided that the AECAT test does not indicate the presence of localized or spot corrosion, as evidenced by a local accumulation of corrosion activity noise hits on the tank bottom. Under special circumstances, Grade C results can also be used if a previous out-of-service API 653 internal inspection report is available and meets the criteria specified below.

Grade C can only be used if the method is implemented meeting the following six criteria. First, the AECAT test does not indicate the presence of localized or spot corrosion, as evidenced by a local accumulation of corrosion activity noise hits on the tank bottom. Second, the tank bottom has a minimum of five (5) years of thickness remaining before the minimum allowable thickness, $T_{MAT}$, is reached when computed using the mean corrosion rate due to pitting, $<CR_{max}>$, of the distribution used for $F_X(x)$, i.e., $[(T_{P\ min} - T_{MAT}) - ((t_0+5)* <CR_{max}> T_{P\ min})] \geq 0$. Third, a previous out-of-service API 653 internal inspection that meets the criteria specified in this method in Step 9 is available and is used. Fourth, the second criteria is met using the maximum corrosion rate determined in the API 653 internal inspection. Fifth, in the opinion of a PE, the results of the previous out-of-service API 653 internal inspection tends to minimize the results of the Grade C AECAT test result. Sixth, a PE approves the use of a Grade C test result.

10.4 API External Inspection:

If an external inspection of the tank is performed, it shall be performed following the requirements for external inspections in API 653. The number and type of measurements are specified in API 653.

10.5 Out-of-Service API 653 Internal Inspection:

If a previous out-of-service API 653 internal inspection report has been performed that meets the criteria specified in Step 9, it shall be used to compute TNI-α and TNI unless (1) the report or the inspection was determined by a Certified API 653 Inspector, a PE, or an SME to be poor, inadequate, or not sufficiently reliable to use in this method; (2) the bottom thickness measurements and corrosion rates were not made in the approximate location of the measurements made in Step 2 as part of this method; or (3) the measurements of the minimum thickness and maximum corrosion rate reported in the API 653 report cannot be justified by the measurements presented in the report.

11 Preparation of Apparatus 11.1 Leak Detection Integrity Method or System:

The leak-detection integrity system used to determine whether or not the bottom of the tank has integrity shall be prepared (and implemented) in accordance with the third-party evaluation report and the manufacturer's recommendations.

11.2 Bottom Thickness Measurement Sensor System:

The sensor system used to make thickness measurements of the bottom of the tank shall be prepared (and implemented) in accordance with the manufacturer's recommendations.

11.3 AE Corrosion Activity Test (AECAT):

The AE Corrosion Activity Testing System used to determine whether or not active corrosion is occurring on the bottom of the tank shall be prepared (and implemented) in accordance with the manufacturer's recommendations.

11.4 In-Service API 653 External Inspection:

The sensor systems used to make the measurements in an API 653 External Inspection shall be prepared (and implemented) in accordance with API 653 and the manufacturer's recommendations.

12 Calibration and Standardization

Each of the sensors or measurement systems used in the implementation of this method shall be calibrated on an annual basis in accordance with the manufacturer's specification to verify the measurement sensors comprising the total measurement system are in compliance with the precision and bias specified by the manufacturer and as required by this method.

12.1 Leak Detection Integrity Method or Test System:

The tank sensors comprising the leak detection integrity method or system shall be calibrated on an annual basis in accordance with the manufacturer's specifications. (NOTE: Calibration is required whenever the sensors are removed from service for maintenance or repair.)

12.2 Bottom Thickness Measurement Sensor System:

The tank bottom thickness measurement system shall be calibrated on an annual basis in accordance with the manufacturer's specifications to determine the precision and bias of the thickness measurements. In addition, a field calibration check of the tank bottom thickness measurement sensor should be performed during each application of this method to ensure the sensor is functional.

12.3 AE Sensors Used in a AE Corrosion Activity Test (AECAT):

The AE sensors shall be calibrated on an annual basis in accordance with the manufacturer's specifications. The AE sensors used during the implementation of this method should be check in the field to insure the AE sensors are responding with a minimum SNR as specified in Section 6.3. For AE tests performed with AE sensors mounted on the walls, a #9 lead in a mechanical pencil shall be broken to insure each sensor could detect an impulsive corrosion pulse occurring anywhere from the bottom of the tank with an SNR≥70 dB. For AE tests performed with AE sensors mounted on an array that is submerged in the liquid product, a mechanical clicker, which is submerged in the product, shall be used to insure each sensor could detect an impulsive corrosion pulse anywhere from the bottom or floor of the tank with an SNR≥70 dB or an SNR capable of detecting any active corrosion activity.

13. Calculation or Interpretation of Results

The output of this method is TNI, i.e., the time until the next out-of-service API 653 internal inspection should be performed. The value of TNI is based on the condition of the tank bottom. This method is based on in-service measurements performed within well-accepted industry practice. When $T_{MAT}$ is used to determine TNI, which is the recommended approach of this method, TNI is very conservative and has a built-in factor of safety. This method limits TNI to 10 years or less, but allows TNI to be updated at 10 years by re-assessing TNI. This method limits the total time between out-of-service API 653 internal inspections to 30 years, which is currently used by and in accordance with API 653. TNI can be calculated by using the equations in this method or by using the Excel spreadsheet provided by this method.

14. Report

The output of this method is the time interval, $TNI=\Delta t_{0-N}$, can be reported to the tank owner/operator using the Method Form in Annex 1. For some of the applications of this method, the tank owner/operator may want a more detailed description of the work that follows the type of report prepared when performing an internal or external inspection in accordance with API 653.

15. Precision and Bias

The sensor systems and the measurement, test, and inspection methods used to implement this method shall meet the performance requirements specified by the manufacturers and verified by an annual calibration. In addition, the tank bottom thickness sensor systems used to implement this method shall have a precision of 0.010 in., or less, and a bias of 0.010 in., or less, as verified by the manufacturer's specification and an annual calibration. The precision and bias of the bottom thickness measurements made in Step 2 and, in Step 10, if a previous out-of-service API 653 internal inspection report is used, is described below and shall be reported.

As illustrated by Eqs. (15.1) and (15.2), the output of this method, TNI, could be determined from the thickness measurements of the tank bottom and the corrosion rate determined from them as illustrated in Eq. (15.1).

$$TNI=(T_{min\ 0}-T_{MAT})/CR_{max} \quad (15.1)$$

where $$CR_{max}=[(T_P-T_{min\ 0})/(t_P-t_0)] \quad (15.2)$$

In this method, the full range or distribution, $F_X(x)$, of maximum corrosion rates, $CR_{max}$, that could occur for the tank of interest in Eq. (15.2), from the very smallest to the very largest, is used to estimate TNI-ER, instead of only one value. Step 4 describes two methods of determining, $F_x(x)$, but both methods require measurement of the tank bottom thickness at two points in time, $T_P$ after repairs and $T_{min\ 0}$ for uniform and maximum corrosion rate due to pitting, for the tank floor at $t_0$, to determine $CR_{max}$. For simplicity, in this method, the precision and bias will be specified in terms of the precision and bias of making these bottom thickness measurements as if only one value of $T_P$ and $T_{min\ 0}$ were required. This method requires that the bottom thickness measurement sensor system used to measure bottom thickness and corrosion rate at $t_0$ and $t_P$ have a precision of 0.010 in., or less, and a bias of 0.010 in., or less, where the actual precision and bias of these sensors is dependent upon the manufacturer's specification or the annual calibration of these sensors, and how many measurements are averaged together when making bottom thickness measurements at each location.

The precision and bias of $T_P$ and $T_{min\ 0}$ required by this method were specified to insure that even if $CR_{max}$ determined from measurements of $T_{min\ 0}$ and $T_P$ had a three standard-deviation (SD) error in both precision and bias, the resulting maximum corrosion rate would not be large enough to exceed $T_{MAT}$ during the entire TNI period, where $T_{MAT}$ is the thickness at which tank bottom failure is defined. As defined by API 653, the smallest value of $T_{MAT}$ is 0.050 in. If the AST does not include a release prevention barrier, then $T_{MAT}$ is 0.10 in.

Eq. (15.3) defines the one SD error in the difference term of $T_P - T_{min\ 0}$ that is used to determine $CR_{max}$ as $$S_{TP-Tmin\ 0} = [((S_{TP}/n_P)^2 + (S_{Tmin\ 0}/n_0)^2)]^{0.5}, \quad (15.3)$$

where $S_{CRmax} = S_{TP-Tmin\ 0}/(t_P - t_0)$; $S_{TP}$ is the precision or bias of the sensor system used to measure bottom thickness for a single measurement at time, $t_P$; $S_{Tmin\ 0}$ is the precision or bias sensor system used to measure bottom thickness for a single measurement at time, $t_P$; it is assumed that there is no error in measuring time, $t_P$ or $t_0$; $n_P$ is typically determined by one measurement made during the previous out-of-service API 653 internal inspection; and $n_0$ is specified in this method as 8 to 10 in-service measurements at a location.

Eq. (15.3) can be used to determine the precision or the bias of the sensor system used to measure bottom thickness and corrosion rate. The combined error is determined from Eq. (15.4).

$$S_{Total} = [(S_{Precision})^2 + (S_{Bias})^2]^{0.5}, \quad (15.4)$$

where $S_{Precision}$ and $S_{Bias}$ are each defined by Eq. (15.3) and $S_{TP}$ and $S_{Tmin\ 0}$ are provided by the manufacturer when the bottom thickness sensor is purchased or from the annual calibration of the sensor.

The precision and bias were specified so that the precision and bias of the bottom thickness sensor is sufficient so that a three standard deviation error in the bottom thickness measurements would not be large enough to offset the margin of safety provided by $T_{MAT}$. Thus, $S_{Precision}$ and $S_{Bias}$ need to be sufficiently small so that $S_{Total}$ satisfies Eq. (15.5).

$$T_{MRT} = T_{MAT} - (3*[S_{Total}]) > 0.0 \quad (15.5)$$

As an illustration, $T_{MRT}$ equals 0.0050 in. for the minimum number of measurements required by this method, i.e., when $T_{MAT} = 0.050$ in., $n_P = 1$, $n_0 = 8$, $S_{Precision} = 0.010$ in., and $S_{Bias} = 0.010$ in. Thus, Eq. (15.5) is always satisfied provided that $T_{MAT} \geq 0.050$ in., $n_P \geq 1$, $S_{Precision} \leq 0.010$ in., and $S_{Bias} \leq 0.010$ in., $n_P \geq 1$ and that $n_0 \geq 8$. This precision and bias is very conservative, because as described below, in most instances, standard industry practice uses bottom thickness sensors with a precision and bias of 0.005 in. or less.

This method recognizes that it would have been more direct to establish the precision and bias on TNI itself, either as an absolute error on TNI or as a percentage error on TNI. This is not practical, however, and was not used to define these quantities, because the error in TNI is largest when the corrosion rates are the smallest and provides the least risk to tank bottom failure. To illustrate this point, a set of calculations was performed with $T_{MAT} = 0.05$ in., with $n_0 = 8$ thickness measurements made at $t_0$, and one thickness measurement made at $t_P$ using a sensor with a precision and bias of 0.01 in., respectively, where the one standard deviation error in TNI, $SD_{TNI}$, is given by Eq. (15.6). Assuming the bottom thickness measurement, $T_P$ was 0.25 in. at $t_P$, and $T_{min\ 0}$ at $t_0$ was determined for two different estimated bottom thicknesses (0.23 in. and 0.17 in.) at $t_0$. This results in corrosion rates of 2 mpy and 8 mpy, respectively. For a corrosion rate of 2.0 mpy, TNI=90 years with errors of $SD_{TNI}=5.09$ years and 5.7% for a $CR_{max}$. For a corrosion rate of 8 mpy, TNI=15 years with errors of $SD_{TNI}=0.485$ years, and 3.2% for a $CR_{max}$. Clearly, while the error is largest for the smaller corrosion rate (i.e. 5.09 years versus 0.49 years or 5.7% versus 3.2%), the risk of tank bottom failure is definitely less for the smaller corrosion rate, because the TNI=90 years for the smaller corrosion rate is so much greater than the TNI=15 years for the higher corrosion rate.

$$\begin{aligned}\text{One SD Error TNI in years} = SD_{TNI} = \\ TNI[\{(S_{Tmin\ 0-TMAT}/n_0)^2/(T_0-T_{MAT})\} + \\ \{((S_{TP}/n_P)^2 + (S_{Tmin\ 0}/n_0)^2)/(CR_{max} = \\ [(T_P-T_{min\ 0})/(t_P-t_0)])\}]^{0.5}\end{aligned} \quad (15.6)$$

It should be noted that the precision and bias for the measurement sensor or sensor systems used to measure the thickness and corrosion rate determined in an out-of-service API internal inspection is not specified in API 653. Instead, Appendix G in API 653 specifies in detail the criteria for how the tank bottom measurements should be made during an out-of-service API 653 internal inspection.

Historically, the commonly accepted industry practice for the measurement of the bottom thickness measurements made by tank owners/operators, or their contractors, requires the use of measurement sensors with a precision and bias of 0.010 in., or better. In general, the bottom thickness measurements made as part of an out-of-service API 653 internal inspection are made with an ultrasonic thickness (UT) sensing or measurement sensor and a pitting caliper. The UT sensors used typically have a precision and bias of 0.005 in. and sometimes as low as 0.002 in.; the resolution for these measurements is usually 0.001 in. to 0.002 in. The pitting calipers used typically have a precision and bias of 0.005 in. Thickness sensor measurement errors of 0.010, 0.005, and 0.002 in. result in relative thickness errors of 4.0, 2.0, and 0.8%, respectively, for a typical tank bottom that has a thickness of 0.25 in.

16 Keywords

The following keywords are applicable to this method: Aboveground Storage Tank (AST), Bulk Underground Storage Tank (bulk UST), Internal Inspection Interval, Tank Assessment Method, Tank Assessment Management, Tank Asset Management, Internal Inspection of a Tank, Risk Based Inspection, RBI, API 653 Internal Inspection, Tank Bottom, Tank Floor, Tank Bottom Thickness, Tank Bottom Corrosion Rate, Tank Survival Distribution, Tank Failure Distribution, Tank Life Expectancy, and Equivalent Risk.

What is claimed:

1. A method for determining the time to the next out-of-service internal inspection of a storage tank, TNI, from the time of application of this method, comprising the steps of:
   (a) performing and passing a leak detection integrity test;
   (b) measuring the thickness of the tank bottom in at least one location of the tank;
   (c) generating a survival probability distribution of the tank bottom for the tank of interest;
   (d) generating a Bayesian update of said survival probability distribution for said tank of interest; and
   (e) calculating TNI using said survival probability distribution and said Bayesian update of said survival probability distribution.

2. The method of claim 1, wherein said method is reapplied to determine an updated TNI.

3. The method of claim 1, wherein said method is used to re-assess the condition of said tank bottom at periodic intervals within the internal inspection interval.

4. The method of claim 1, wherein said method is performed to address the 10-year re-assessment for risk based inspection (RBI) methods of internal tank inspection in API 653.

5. The method of claim 1, wherein said survival probability distribution is generated for a set of tanks that also includes said tank of interest.

6. The method of claim 1, wherein said survival probability distribution is generated for a set of tanks with similar characteristics as said tank of interest.

7. The method of claim 1, wherein said survival probability distribution is generated for the same corrosion conditions as said tank of interest.

8. The method of claim 1, wherein said survival probability distribution is generated for the same operational conditions as said tank of interest.

9. The method of claim 1, wherein said survival probability distribution is generated for the same corrosion and operational conditions as said tank of interest.

10. The method of claim 1, wherein said survival probability distribution is generated for a set of tanks that also includes the corrosion conditions as said tank of interest.

11. The method of claim 1, wherein said survival probability distribution is generated for a set of tanks that also includes the operational conditions as said tank of interest.

12. The method of claim 1, wherein said survival probability distribution is generated for a set of tanks that also includes the corrosion and operational conditions as said tank of interest.

13. The method of claim 1, wherein said Bayesian update of said survival probability distribution is generated by calculation using said survival probability distribution.

14. The method of claim 13, wherein said calculation includes integrating the survival probability distribution from the survival probability at said time of application of said method and normalizing or dividing by said survival probability at said time of application of said method.

15. The method of claim 1, wherein said Bayesian update of said survival probability distribution is generated for the same conditions as used to generate said survival probability distribution.

16. The method of claim 1, wherein said Bayesian update of said survival probability distribution is generated using the same information or data used to generate said survival probability distribution.

17. The method of claim 1, wherein said survival probability distribution is generated from a corrosion rate probability distribution.

* * * * *